US009983670B2

(12) United States Patent
Coleman et al.

(10) Patent No.: US 9,983,670 B2
(45) Date of Patent: May 29, 2018

(54) SYSTEMS AND METHODS FOR COLLECTING, ANALYZING, AND SHARING BIO-SIGNAL AND NON-BIO-SIGNAL DATA

(71) Applicant: INTERAXON INC., Toronto, Ontario (CA)

(72) Inventors: Trevor Ce Coleman, Toronto (CA); Christopher Allen Aimone, Toronto (CA); Ariel Stephanie Garten, Toronto (CA); Locillo (Lou) Giuseppe Pino, Cambridge (CA); Paul Harrison Baranowski, Toronto (CA); Raul Rajiv Rupsingh, Brampton (CA); Kapil Jay Mishra Vidyarthi, Toronto (CA)

(73) Assignee: INTERAXON INC., Toronto (CA)

( * ) Notice: Subject to any disclaimer, the term of this patent is extended or adjusted under 35 U.S.C. 154(b) by 0 days. days.

(21) Appl. No.: 14/115,781

(22) PCT Filed: Sep. 16, 2013

(86) PCT No.: PCT/CA2013/000785
§ 371 (c)(1),
(2) Date: Nov. 5, 2013

(87) PCT Pub. No.: WO2014/040175
PCT Pub. Date: Mar. 20, 2014

(65) Prior Publication Data
US 2015/0199010 A1    Jul. 16, 2015

Related U.S. Application Data

(60) Provisional application No. 61/701,176, filed on Sep. 14, 2012, provisional application No. 61/701,002, filed on Sep. 14, 2012.

(51) Int. Cl.
*A61B 5/0482*    (2006.01)
*A61B 5/0484*    (2006.01)
(Continued)

(52) U.S. Cl.
CPC ............ *G06F 3/015* (2013.01); *A61B 5/0006* (2013.01); *A61B 5/0022* (2013.01);
(Continued)

(58) Field of Classification Search
USPC ........................................................ 705/2–4
See application file for complete search history.

(56) References Cited

U.S. PATENT DOCUMENTS 3,863,625 A * 2/1975 Viglione .............. A61B 5/4094
                                                                600/545
6,904,408 B1 * 6/2005 McCarthy ............ A61B 5/6815
                                                                705/2

(Continued)

FOREIGN PATENT DOCUMENTS

| CA | 2548290 A1 | 6/2005 |
| EP | 1815784 A1 | 8/2007 |
| WO | 2010071604 A1 | 6/2010 |

OTHER PUBLICATIONS

WIPO, International Search Report dated Dec. 4, 2013, issued in corresponding International Patent Application No. PCT/CA2013/000785.

(Continued)

*Primary Examiner* — Mark Holcomb
(74) *Attorney, Agent, or Firm* — Norton Rose Fulbright Canada LLP

(57) ABSTRACT

A computer network implemented system for improving the operation of one or more biofeedback computer systems is provided. The system includes an intelligent bio-signal processing system that is operable to: capture bio-signal data and in addition optionally non-bio-signal data; and analyze the bio-signal data and non-bio-signal data, if any, so as to: extract one or more features related to at least one individual interacting with the biofeedback computer system; classify the individual based on the features by establishing one or (Continued)

more brain wave interaction profiles for the individual for improving the interaction of the individual with the one or more biofeedback computer systems, and initiate the storage of the brain waive interaction profiles to a database; and access one or more machine learning components or processes for further improving the interaction of the individual with the one or more biofeedback computer systems by updating automatically the brain wave interaction profiles based on detecting one or more defined interactions between the individual and the one or more of the biofeedback computer systems. A number of additional system and computer implemented method features are also provided.

44 Claims, 19 Drawing Sheets

(51) Int. Cl.
G06F 3/01 (2006.01)
A61B 5/0476 (2006.01)
G06F 17/30 (2006.01)
H04L 12/16 (2006.01)
A61B 5/00 (2006.01)
H04L 29/06 (2006.01)

(52) U.S. Cl.
CPC .......... *A61B 5/0024* (2013.01); *A61B 5/0476* (2013.01); *A61B 5/486* (2013.01); *G06F 17/30* (2013.01); *H04L 12/16* (2013.01); *H04L 67/42* (2013.01)

(56) References Cited

U.S. PATENT DOCUMENTS

| | | | | |
|---|---|---|---|---|
| 8,041,801 | B2* | 10/2011 | Nakamura | G06F 17/30867 340/321 |
| 2004/0077967 | A1* | 4/2004 | Jordan | A61B 5/04012 600/544 |
| 2007/0173733 | A1* | 7/2007 | Le | G06F 19/363 600/544 |
| 2009/0220429 | A1* | 9/2009 | Johnsen | A61B 5/0484 424/9.3 |
| 2010/0168533 | A1* | 7/2010 | Johnsen | G06F 19/345 600/301 |
| 2011/0313308 | A1 | 12/2011 | Zavoronkovs et al. | |
| 2012/0007737 | A1 | 1/2012 | Kangas et al. | |
| 2012/0049998 | A1* | 3/2012 | Lim | H04M 1/72569 340/1.1 |
| 2012/0090003 | A1* | 4/2012 | Dove | G06F 3/015 725/38 |
| 2012/0143568 | A1* | 6/2012 | Kagan | A61N 1/36082 702/189 |
| 2013/0314243 | A1* | 11/2013 | Le | A61B 5/0002 340/870.01 |

OTHER PUBLICATIONS

European Patent Office, Extended European Search Report for EP Application No. 13836691.9 dated Apr. 29, 2016.
European Patent Office, Office Action for EP Application No. 13836691.9 dated May 17, 2016.
EPO, Office Action for EP Application No. 13836691.9 dated Dec. 14, 2016.

* cited by examiner

SECOND ORDER PATTERN DETECTION: UNSUPERVISED — 11000A

| CANDIDATE | $o_x$ | $e_x$ | $d_x$ | PATTERN? |
|---|---|---|---|---|
| A=Ab, B=Ab | 24 | 27 | -1.20 | NO |
| A=Pr, B=Ab | 27 | 24 | 1.18 | NO |
| A=Ab, B=Pr | 30 | 27 | 1.20 | NO |
| A=Pr, B=Pr | 21 | 24 | -1.18 | NO |
| A=Ab, C=N | 27 | 25.9 | 0.44 | NO |
| A=Pr, C=N | 22 | 23.1 | -0.44 | NO |
| A=Ab, C=E | 27 | 28.1 | -0.44 | NO |
| A=Pr, C=E | 26 | 24.9 | 0.44 | NO |
| B=Ab, C=N | 26 | 24.5 | 0.59 | NO |
| B=Pr, C=N | 23 | 24.5 | -0.59 | NO |
| B=Ab, C=E | 25 | 26.5 | -0.59 | NO |
| B=Pr, C=E | 28 | 26.5 | 0.59 | NO |

FIG. 11A

THIRD ORDER PATTERN DETECTION: UNSUPERVISED — 11000B

| CANDIDATE | $o_x$ | $e_x$ | $d_x$ | PATTERN |
|---|---|---|---|---|
| A=Ab, B=Ab, C=N | 23 | 13 | 5.58 | YES |
| A=Pr, B=Pr, C=N | 19 | 11.5 | 4.28 | YES |
| A=Pr, B=Ab, C=E | 24 | 12.5 | 6.46 | YES |
| A=Ab, B=Pr, C=E | 26 | 14 | 6.64 | YES |

FIG. 11B $$p(C|F_1,\ldots,F_n) = \frac{1}{Z} p(C) \prod_{i=1}^{n} p(F_i|C)$$

FIG. 14

PROBABILITIES FOR FEATURE BINS EEG CHANNEL 1 -9000 TIME SLICES PER SESSION

| BIN | # OCCURRENCES IN BUSY MIND | P (BIN/BUSY MIND) | # OCCURRENCES IN QUIET MIND | P (BIN/QUIET MIND) |
|---|---|---|---|---|
| 1 | 45 | 0.005 | 233 | 0.03 |
| 2 | 2106 | 0.234 | 647 | 0.07 |
| 3 | 1503 | 0.167 | 948 | 0.11 |
| 4 | 846 | 0.094 | 1050 | 0.12 |
| 5 | 333 | 0.037 | 1323 | 0.15 |
| 6 | 747 | 0.083 | 2308 | 0.26 |
| 7 | 585 | 0.065 | 599 | 0.07 |
| 8 | 693 | 0.077 | 887 | 0.10 |
| 9 | 1107 | 0.123 | 932 | 0.10 |
| 10 | 1035 | 0.115 | 73 | 0.01 |

FIG. 15

SYSTEMS AND METHODS FOR COLLECTING, ANALYZING, AND SHARING BIO-SIGNAL AND NON-BIO-SIGNAL DATA

CROSS REFERENCE TO RELATED APPLICATIONS

This application claims all benefit, including priority, of U.S. Provisional Patent Application Ser. No. 61/701,002, filed Sep. 14, 2012, entitled REAL TIME SYSTEM AND METHODS FOR CLASSIFICATION OF MENTAL STATES USING EEG, and U.S. Provisional Patent Application Ser. No. 61/701,176, filed Sep. 14, 2012, entitled SYSTEM AND METHODS FOR COLLECTING, ANALYZING, AND SHARING BIO-SIGNAL AND NON-BIO-SIGNAL DATA, the entire contents of each of which is incorporated herein by this reference.

FIELD OF THE INVENTION

The present invention relates to bio-signal collection methods, and systems that utilize bio-signal data.

BACKGROUND OF THE INVENTION

Bio-signals are signals that are generated by biological beings that can be measured and monitored. Electroencephalographs, galvanometers, and electrocardiographs are examples of devices that are used to measure and monitor bio-signals generated by humans.

A human brain generates bio-signals such as electrical patterns known, which may be measured/monitored using an electroencephalogram ("EEG"). These electrical patterns, or brainwaves, are measurable by devices such as and EEG. Typically, an EEG will measure brainwaves in an analog form. Then, these brainwaves may be analyzed either in their original analog form or in a digital form after an analog to digital conversion.

Measuring and analyzing bio-signals such as brainwave patterns can have a variety of practical applications. For example, brain computer interfaces ("BCI") have been developed that allow users to control devices and computers using brainwave signals.

Training is often required before people are capable of performing tasks using a BCI. This training generally requires the user to learn how to exert a measure of control over their brainwaves. However existing training methods for enabling users to learn sufficient control over their brainwaves to enable use of BC's are generally difficult to learn.

SUMMARY OF THE INVENTION

In one aspect of the invention, an improved training method is provided for enabling users to learn how to control their brainwaves so as to enable the use of BCIs. A training method is provided that decreases the learning curve for using a BCI. The system may identify characteristics of a user's brain state to determine the user's cognitive or emotional state regardless of the user's ability to control a BCI.

In another aspect of the invention, an improved BCI system is provided. First, a novel and innovative BCI system is provided that obtains and analyzes bio-signal data, and also systematically and selectively obtains non-bio-signal data, and analyzes the bio-signal data so as to improve the analysis of bio-signal data. Certain relationships between bio-signal data and non-bio-signal were known, however, the inventor has conceived of a system that may support a range of different applications that relying on a BCI, and enables the collection of useful bio-signal data and also non-bio-signal data in a way that supports real time or near real time analysis of both data sets, so as to support for example accurate and responsive performance of the applications that utilize the BCI.

Also, non-bio-signal data may not be considered when analyzing bio-signal data such as EEG data. However, environmental factors may influence bio-signals. For example, ambient temperature may affect a person's heart rate. Similarly, high stress situations may affect a person's brain wave patterns.

Once, the data is collected for the user or the plurality of users, in accordance with another aspect of the invention, a computer system is provided that processes and analyzes the aggregated data. The aggregated data may be shared (for example with other network-connected devices that are authorized to connect to the computer system of the present invention). In another aspect, the results of the analysis and processing of the aggregated data may be shared.

In another aspect, sharing may involve providing direct access to the individual data or results or the aggregated data or results; or it may mean providing access to the data, results, or both through an application programming interface (API), or other known means.

Therefore, systems and methods are provided for collecting, analyzing, interpreting, and sharing bio-signal and non-bio-signal data. Aspects and embodiments of these systems and methods may use analysis algorithms, e.g. machine learning algorithms, to analyze the aggregated data for the user or the plurality of users. It is predicted that the systems and methods may be improved as the amount of aggregated data increases, whether it is more data for the user, more data for the plurality of users, or both.

Other aspects and embodiments of these systems and methods may collect, analyze and associate particular bio-signal and non-bio-signal data with specific mental states for both individuals and groups. The collected data, analyzed data or functionality of the systems and methods may be shared with others, e.g. third party applications, other users, etc.

In an embodiment, one or more client devices are connected to internal sensors, external sensors, wearable sensors, and user effectors to collect bio-signal and non-bio-signal data, and these devices are linked to a server. A skilled person would understand the server may be local, remote, cloud based or software as a service platform (SAAS). Connections between the client device or devices, internal sensors, external sensors, user effectors, and the server may be encrypted. The collected data may be processed and analyzed on the client device or devices, on the server, or both. Collected and analyzed data may be used to build a user profile that is specific to a user. The user profile data may be analyzed, e.g. by machine learning algorithms, either individually or in the aggregate to function as a BCI, or to improve the algorithms used in the analysis. The data, analyzed results, and functionality associated with the system can be shared with third party applications and other organizations through an API.

In another aspect, systems and methods for bio-signal and non-bio-signal data collection and adaptive signal processing are provided. The systems and methods may be used with mobile biofeedback applications.

In accordance with an aspect of the present invention, there is provided a system comprising: at least one client computing device; at least one bio-signal sensor at and in communication with the at least one client computing device; and at least one computer server in communication with the at least one computing device over a communications network; the at least one client computing device configured to: receive time-coded bio-signal data of a user from the at least one bio-signal sensor; transmit the time-coded bio-signal data and acquired time-coded feature event data to the at least one computer server; receive from the at least one computer server a user-response classification of at least part of the time-coded bio-signal data based on an identified pattern of correspondence between the at least part of the time-coded bio-signal data and at least part of the time-coded feature event data at least one respective time code; in accordance with a received input confirming the user-response classification, update a bio-signal interaction profile at the at least one client computing device with the user-response classification, the at least part of the time-coded bio-signal data, and the at least part of the time-coded feature event data at the at least one respective time code.

A method, performed by at least one client computing device in communication with at least one bio-signal sensor at the at least one client computing device, the at least one client computing device in communication with at least one computer server over a communications network, the method comprising: receiving time-coded bio-signal data of a user from the at least one bio-signal sensor; transmitting the time-coded bio-signal data and acquired time-coded feature event data to the at least one computer server; receiving from the at least one computer server a user-response classification of at least part of the time-coded bio-signal data based on an identified pattern of correspondence between the at least part of the time-coded bio-signal data and at least part of the time-coded feature event data at least one respective time code; in accordance with a received input confirming the user-response classification, updating a bio-signal interaction profile at the at least one client computing device with the user-response classification, the at least part of the time-coded bio-signal data, and the at least part of the time-coded feature event data at the at least one respective time code.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

Embodiments will now be described, by way of example only, with reference to the attached figures, wherein:

FIGS. 11A and 11B illustrate tables of data used during an example of meaningful patterns discovery in accordance with the present invention;

FIG. 14 shows the Naïve Bayes formula used in accordance with an aspect of the invention;

FIG. 15 illustrates an example count and corresponding probability for use in an example of the present invention;

Figure 1:
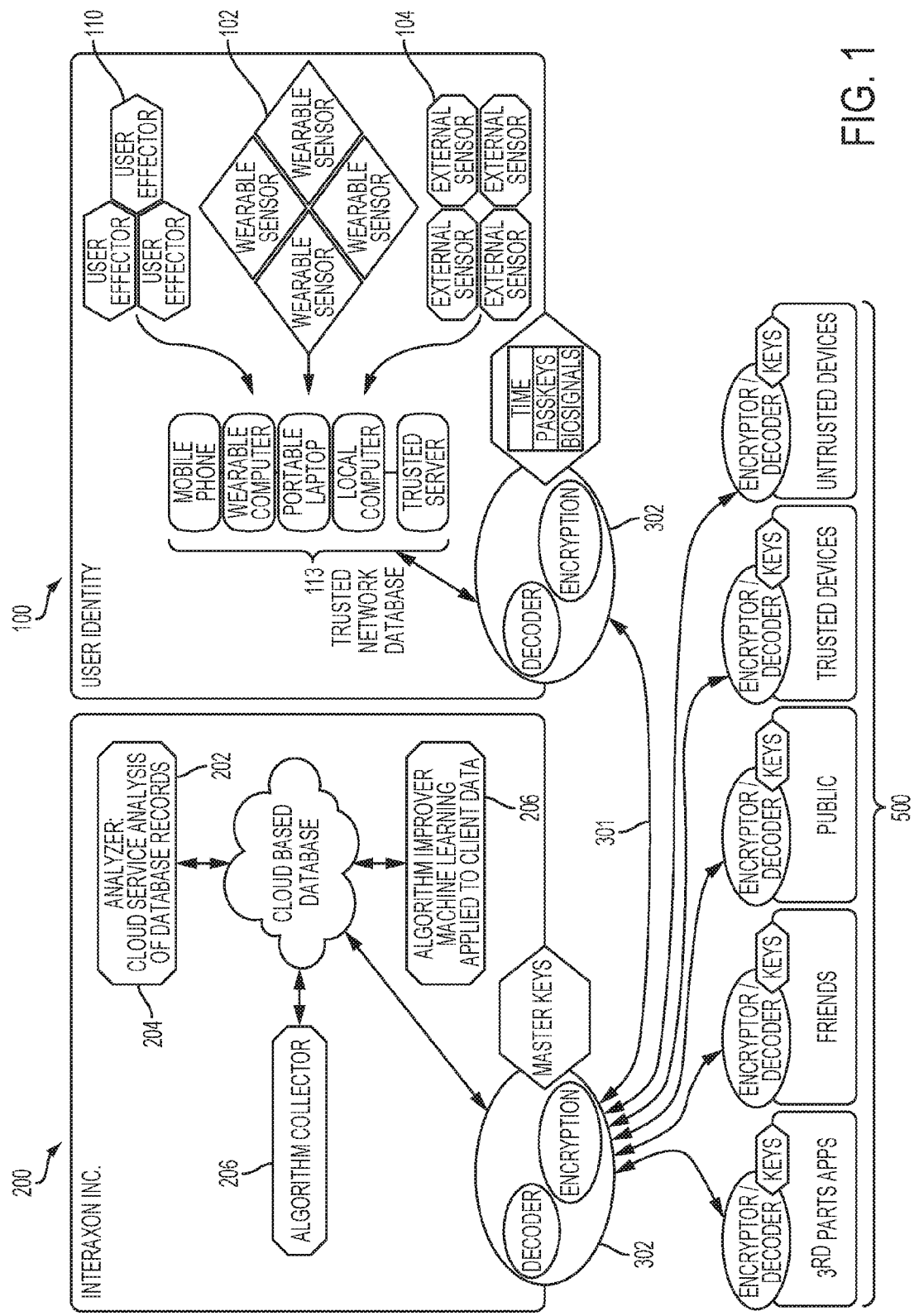
FIG. 1 illustrates an embodiment of the platform, including a possible cloud service model, and a local trusted network of client devices.

In the drawings, embodiments of the invention are illustrated by way of example. It is to be expressly understood that the description and drawings are only for the purpose of illustration and as an aid to understanding, and are not intended as a definition of the limits of the invention.

DETAILED DESCRIPTION

The present invention relates generally to computer systems and computer implemented methods for collecting bio-signal and non-bio-signal data, applying data processing to the collected data, and using the collected and processed data in biofeedback systems. More specifically, the invention provides mechanisms for improving the performance of biofeedback systems based on a novel and innovative (A) computer system and database architecture for collecting and processing bio-signal data and non-bio-signal data, (B) specific computer system features and functions, and computer implemented techniques for utilizing bio-signal data and non-bio-signal data to improve the performance of biofeedback systems.

As further explained below, the present invention provides a computer system and a series of computer implemented methods that promote the adoption of biofeedback systems and improve their functionality for users, in novel and innovative ways.

Individuals may differ from one another in the respective brainwave patterns exhibited, and therefore the manner in which each individual interacts with a BCI may also vary. Learning how best to interact with a BCI can be challenging and frustrating for individuals, and may affect adoption of biofeedback systems, or may cause users to begin using such systems, but not use them as much as they would if training on the systems were improved. Discoveries in accordance with aspects of the present invention is that an individual may be characterized as having particular features or attributes to the way in which the individual interacts with a BCI; that a feature extractor may be used to streamline the process of determining the parameters of how a particular individual may interact with a BCI (and optionally classifying individuals based on these features); and also that machine learning systems and methods may be utilized in order to improve the efficiency of feature extraction and classification. Further details and embodiments for implementing these aspects of the invention are described below.

An embodiment of a system for bio-signal and non-bio-signal data collection and analysis is provided comprising at least one client device for collecting data, at least one computer server for communicating with the client device to process and analyze the collected data together with the at least one client device, and share the collected and/or analyzed data with other client devices Referring to FIG. 1, in an embodiment of the system there is shown a trusted network of local client devices 113 and a software as a service (SAAS) platform 200 operating at one or more computer servers. The trusted network of local devices may comprise, without limitation, one or more of the following, in various combinations: a mobile phone, wearable computer, laptop, local computer, or trusted server.

As shown in FIG. 1, the trusted network of local client devices 113 and the SAAS platform 200 may communicate via a network connection 301, for example, a wired or wireless internet connection. Furthermore, the devices in the trusted network may be configured to communicate with each other. Systems and methods for local networking between devices are known and non-limiting examples of such methods are wired, wireless, local peer-to-peer, and BLUETOOTH networking.

Figure 2:
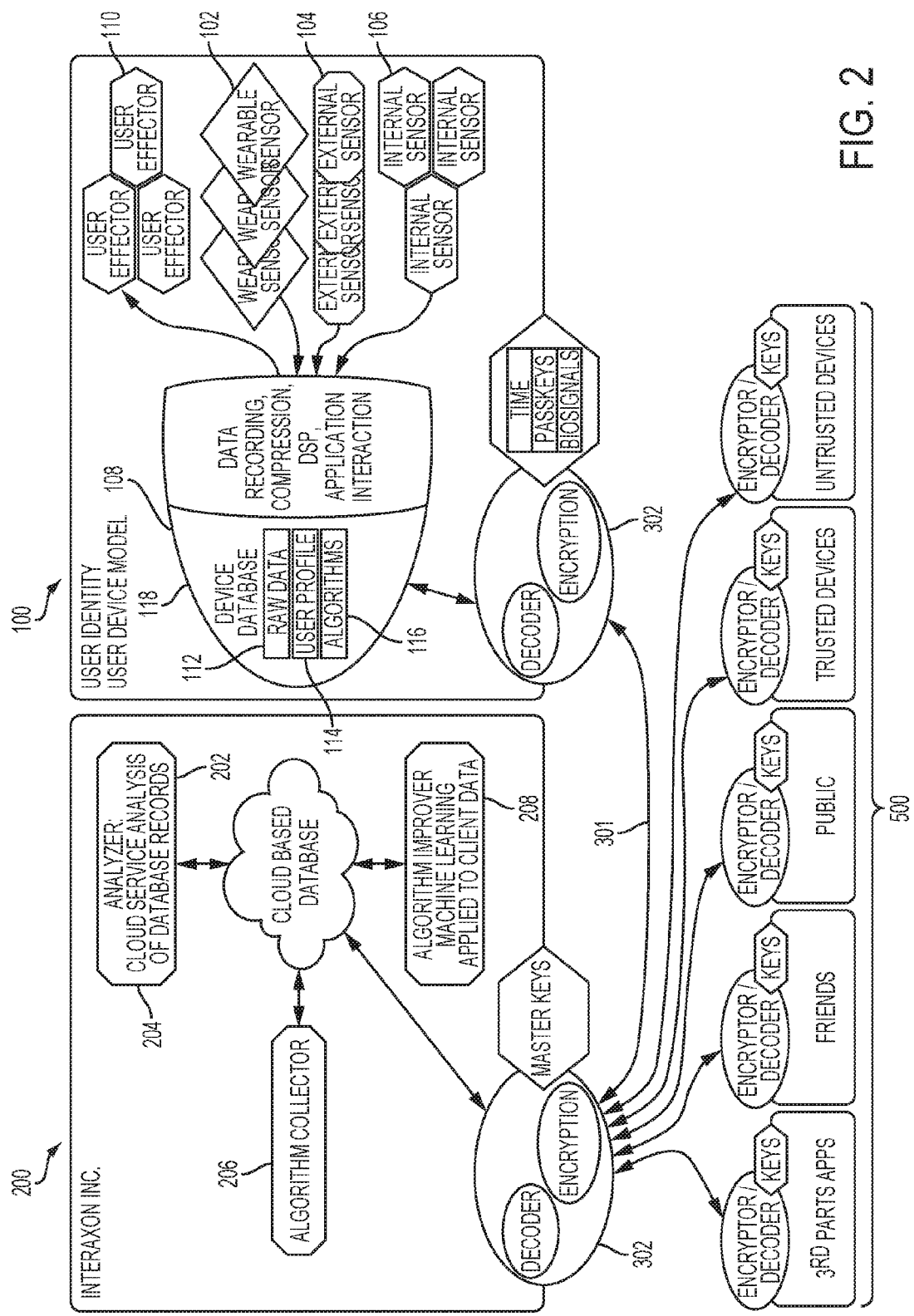
FIG. 2 illustrates an embodiment of the platform that includes a cloud service model for a user associated with a single client device.

Referring to FIG. 2, an embodiment of the system is shown with a single client device 100 and a software as a service (SAAS) platform 200. The client device 100 may be, for example and without limitation, a smartphone, cell phone, or other computing device having one or more sensors. The client device 100 may communicate with the SAAS platform 200 through a network connection 301, for example, a wired or wireless internet connection.

The start and endpoints of the above described connections 302 may be configured to encrypt and decrypt data transmissions using known encryption techniques. Non-limiting examples of such techniques can include MD5 or SHA encoding. Additionally, protocols such as secure HTTP (HTTPS) can be used to encrypt the transmission medium.

As shown in FIGS. 1 and 2, internal sensors 106, external sensors 104, wearable sensors 102, and user effectors 110 may be operatively connected to the trusted network of local devices 113 (FIG. 1) or the client device 108 (FIG. 2). A skilled person would understand that the internal sensors 104, external sensors 106, wearable sensors 102 and user effectors 110 may be operatively connected to one or more of the devices in the trusted local network of devices or client device. Furthermore, a skilled person would understand that not all of the internal sensors 106, external sensors 104, wearable sensors 102, and user effectors 110 may be necessary to perform the methods described herein.

Sensors for collecting bio-signal data include, for example, electroencephalogram sensors, galvanometer sensors, or electrocardiograph sensors. For example, a wearable sensor 102 for collecting biological data, such as a commercially available consumer grade EEG headset with one or more electrodes for collecting brainwaves from the user. A skilled person would understand that an EEG using fewer electrodes would make the wearable sensor 102 more affordable to produce, although an EEG with more electrodes would comparatively collect more data, or collect data more accurately.

The one or more internal sensors 106, external sensors 104, or wearable sensors 102 may collect bio-signal or non-bio-signal data other than EEG data. For example, bio-signal data may include heart rate or blood pressure, while non-bio-signal data may include time GPS location, barometric pressure, acceleration forces, ambient light, sound, and other data. Bio-signal and non-bio-signal data can be captured by the internal sensors 106, external sensors 104, or both.

The distinction between internal and external sensors refers to whether the sensor is contained within the client device (mobile computing device) 108. For example, a smart phone may have a plurality of built-in internal sensors 106 for collecting non-bio-signal data. External sensors 104, such as wireless headsets or other types of sensors, may complement or replace the available internal sensors 106. The external sensors 104 may be connected to the client device or devices of the trusted local network 113 or mobile computing device 108 by wired or wireless connection, such as, for example, USB or BLUETOOTH connections. Other ways to connect external sensors to the client device or devices in a trusted local network 113 or mobile computing devices 108 are possible.

User effectors 110 are for providing feedback to the user. A "user effector" may be many manner of device or mechanism for having an effect on a user or triggering a user, for example to act on a message. For example, user effector 110 could be a vibration, sound, visual indication on a display or some other way of having an effect on the user. A user effector could be internal or external to the client device, as was described above for internal sensors. Furthermore, the user effector 110 may be connected to the client device in a manner similar to external sensors, as described above.

User effectors 110 can be used, for example, to provide real-time feedback on characteristics related to the user's current mental state for example. These user effectors may also be used to assist a user in achieving a particular mental state, such as, for example, a meditative state. The user effector 110 may be implemented for example using a graphical user interface designed to enable a user to interact with a meditation training application in an effective manner.

In order to process and analyze collected bio-signal and non-bio-signal data, methods and means for processing and analyzing the collected data are required. Processing collected data can be performed by hardware, software, or some combination of the two. A skilled person would understand that the processing and analysis of data can be performed on a client device, a local server, a remotely located server, a cloud-based server, a SAAS platform, or some combination thereof. A cloud-based platform implementation have provide one or more advantages including: openness, flexibility, and extendibility; manageable centrally; reliability; scalability; being optimized for computing resources; having an ability to aggregate information across a number of users; and ability to connect across a number of users and find matching sub-groups of interest.

The processing and analyzing of collected data may be implemented in computer software or hardware at the at least one client device and at least one computer server. For simplicity, this combination of hardware and software may be referred to as the processing and analyzing system platform (or "system platform"). Wherever reference is made to the term "cloud" or "cloud server", this is intended to refer to the at least one computer server of the system platform. While embodiments and implementations of the present invention may be discussed in particular non-limiting examples with respect to use of the cloud to implement aspects of the system platform, a local server, a single remote server, a SAAS platform, or any other computing device may be used instead of the cloud.

Each time analysis or processing of user bio-signal data (such as brainwave data) is performed, an instance of aspects of the system platform may be may be generated by the system platform, initiated at either the client device or the cloud, in order to analyze the user's private bio-signal data using particular analysis or processing parameters applied during the analysis or processing. For simplicity, such an instance may be referred to as the system platform "pipeline". Each instance of the pipeline may have an associated pipeline identifier ("ID"). Each pipeline may be associated with a particular activity type, user, bio-signal type of a particular user, application, or any other system platform-related data. Each pipeline may maintain particular pipeline parameters determined to analyze the user's bio-signal data in a particular way, consistent either with previous analysis of the particular user's bio-signal data, consistent with previous analysis of one or more other user's bio-signal data, or consistent with updated data at the cloud server derived from new or updated scientific research pertaining to the analysis of bio-signal data. Pipelines and/or pipeline parameters may be saved for future use at the client computing device or at the cloud.

The system platform may preprocess the raw collected biological and non-biological data 112. This can involve, as non-limiting examples, noise filtering and interpolating gaps in signals, and/or any other solution for handling issues related to signal collection and transmission.

The system platform may then use the preprocessed data to extract features from the signal. For example, this may be done by projecting the EEG signal into a lower dimensioned feature space. This projection may aid in the classification of the collected data, for example, by increasing the separability of classes.

The system platform may then classify the extracted features of the data. This classification may provide an indication of the mental state of the user, such as a meditative state. Various algorithms 116 can be used to classify the features determined in previous stages. For example, a minimum mean distance classifier or a K nearest neighbours classifier may be employed to analyze the data.

Feature extraction and classification may be performed by machine learning systems of the system platform. In particular, supervised machine learning systems and methods may be employed to improve the accuracy of the steps of feature extraction and classification.

Representative Embodiment of System—MED-CASP

In one implementation of the invention a Multi-modal EEG Data-Collection and Adaptive Signal Processing System (MED-CASP System) for enabling single or multi-user mobile brainwave applications may be provided.

At the core of the application there is an implementation of the system platform, a cross platform mobile EEG platform specifically for enabling BCI applications. This system platform may be implemented is a hardware and software solution that is comprised of an EEG headset, a client side application and a cloud service component. The client side application may be operating on a mobile or desktop computing device.

A particular system implementation may include a range of different features and functions, for example an EEG headset may be designed to target the meditation (such as health and wellness, or human-performance) market segment, and may be designed to be usable with other BCI applications. Non-limiting features of this headset may include: an unobtrusive soft-band headset that can be confidently worn in public; and differentiation from prior art consumer EEG solutions through the use of 3, or 4, or more electrodes (rather than one). This advancement may enable: estimation of hemispheric asymmetries and thus facilitate measurements of emotional valence (e.g. positive vs. negative emotions); and better signal-t-noise ratio (SNR) for global measurements and thus improved access to high-beta and gamma bands, fast oscillation EEG signals, which may be particularly important for analyzing cognitive tasks such as memory, learning, and perception. It has also been found that gamma bands are an important neural correlate of mediation expertise.

In the same or another non-limiting exemplary implementation, possible MED-CASP system features may include: uploading brainwaves and associated sensor and application state data to the cloud from mobile application; downloading brainwave & associated data from the cloud; real-time brain-state classification to enable BCI in games or other applications; transmitting real-time brain-state data to other users when playing a game to enable multi-user games; sharing brainwave data with other users to enable asynchronous comparisons of results; sharing brainwave data to other organizations or third party applications and systems; and support of cloud based user profiles for storing personal information, settings and pipeline parameters that have been tuned to optimize a specific user's experience. In this way, usage of the system platform can be device independent.

Each person's brainwaves are different, therefore requiring slightly different tunings for each user. Each person's brain may also learn over time, requiring the system platform to change algorithm parameters over time in order to continue to analyze the person's brainwaves. New parameters may be calculated based on collected data, and may form part of a user's dynamic profile (which may be called bio-signal interaction profile). This profile may be stored in the cloud, allowing each user to maintain a single profile across multiple computing devices. Other features of the same or another non-limiting exemplary implementation may include: improving algorithms through machine learning applied to collected data either on-board the client device or on the server; saving EEG data along with application state to allow a machine learning algorithm to optimize the methods that transform the user's brainwaves into usable control signals; sharing brainwave data with other applications on mobile device through a cloud services web interface; sharing brainwave data with other applications running on client devices or other devices in the trusted network to provide for the user's brainwave data to control or effect other devices; integration of data from other devices and synchronization of events with brainwave data aid in context aware analysis as well as storage and future analysis; performing time locked stimulation and analysis to support stimulus entrainment event-related potential ("ERP") analysis; and data prioritization that maximizes the amount of useful information obtainable from an incomplete data download (i.e. data is transmitted in order of information salience). The core functionality of the MED-CASP system may be wrapped as an externally-usable library and API so that another developer may use the platform's features in the developer's application(s). The library may be a static library and API for Unity3D, iOS, Android, OSX, Windows, or any other operating system platform. The system platform may also be configured to use a pre-compiled algorithm supplied by a third party within the library, including the ability for a third party developer using the library, to use the developer's own algorithms with the library. The system platform may also support headsets from a variety of vendors; personal data security through encryption; and sharing of un-curated data (optionally using time-limited and fidelity limited access) though the sharing of encryption keys.

Various implementations of the system platform are possible. In particular, various different applications may be developed that utilize the system platform and enable different types of biofeedback systems. Non-limiting examples of such applications are provided herein.

Mobile Device Based Application—Processing at Mobile Device

A data flow for a meditation session with one user in accordance with an exemplary, non-limiting implementation of the present invention is described. A user may execute an application (or "app") on the mobile device (or client computing device). The application may update a display on the mobile device to prompt for input of a user identifier ("ID") and password. Upon receiving the user ID and password, this information may be sent to the cloud server together with an application ID associated with the application executing on the user's mobile device, for processing by security software or hardware (the "security engine") at the cloud server. If the user ID is associated with the password then the security engine sends a message back to the mobile device to display or provide access to at least a part of the user's user profile. The message may further include data for display at the mobile device, including all or a subset of the data stored in the user's profile at or accessible to the cloud server. If the cloud server has computed any new or updated pipeline parameters per activity type since a prior login, these parameters may be sent to the application on the mobile device. The new or updated pipeline parameters may be based on previous calibration exercises and/or data mining and/or new scientific evidence resulting in a change in how the cloud server associates brain wave data with particular parameters. The cloud server may further transmit status of the user's online friends, messages from friends, messages from cloud administrators, or other data to the application on the mobile device.

The mobile device determines if an EEG headband is connected to the mobile device. If no EEG headband is found, instructions on how to connect the headband are displayed on the mobile device display.

Upon connecting an EEG headband with the mobile device, for example via bluetooth or other near field communication protocols, the EEG headband streams EEG data to the mobile device. The mobile device transmits the EEG data to the cloud when the EEG data is received at the mobile device. If the mobile device or the cloud server detects that the EEG headband is not presently being worn by the user, then the user may be either prompted to wear the EEG headband, or the user may be prompted to input other information including, for example, the user's intended use of the device. Some applications at the mobile device may opt to not send data to the cloud when the headset is not being worn.

The user may select a specific activity type (e.g. meditation exercise) from a screen displayed by the application. The app assigns a session ID which may be uniquely derived based on calendar data and time.

Parameters of a meditation algorithm used in the meditation exercise may be calibrated in a variety of ways. In one non-limiting example, the user is guided through a busy mind exercise such as word association or an exercise designed to evoke self-referential thinking. Next, the user may be asked to quiet the user's mind and focus on the user's breath or to complete a body scan. The app may receive a pipeline ID plus associated parameters sent by the cloud when the app is first initialized to process the EEG data. The meditation app may then be ready to use by the user. The mobile device may transmit the following data or information to the cloud server: app ID associated with this application; session ID; user ID; activity type (e.g. calibration-busy mind); and app data including signal type (e.g. EEG), timestamps per EEG sample, timestamps associated with start and stop of activity, and raw EEG data per channel. Other additional sensor data may be sent structured same way as EEG signal type.

The app may apply the pipeline parameters to process the EEG data in the device and it is used to provide feedback to the user through visual screen graphics, audio or tactile feedback. The start and stop time stamps of a session along with the EEG is sent to the User's Profiles with the APP ID, and session ID of the Activity Type. Time stamps associated with the start and end times or significant events such as event related potentials are send to the Cloud. These timestamps are used by the Cloud delineate the different parts of an Activity Type and are stored in the user's profile in the cloud where each time stamp beginning and end is labelled with the type of event it is associated with (e.g. start of Activity, End of Activity, Event Related Potential stimulus, etc.).

Any signal processed data such as EEG band power calculated by the APP is sent to the Cloud per Activity Type. The pipeline in the app uses the prediction model defined by that pipeline ID to calculate a score or feedback. The user receives feedback for each part of the user's session that is computed from the user's EEG signal. These computed results can be either aggregated across parts of the entire session or across the entire session. These results are stored under a session ID in the user profile associated with the app ID. If the cloud altered the user's parameters for a specific pipeline ID then they are stored in the user's profile in the cloud and are transmitted to the app upon next start-up of the app. Computed results can also have time stamps associated with them and the name of the parameter being computed (e.g. score is 192 at time 1:10). Results presented to the user are stored in the user's profile associated with the app ID, activity type, and session ID. The results may be filtered by the system platform to retain salient elements of an activity. The feedback may also include instructions sent to the user from the cloud to the device so that the user may be guided to improve the user's subsequent sessions. This feedback can be kept up to date in the cloud as bio-signal analysis evidence grows and changes from literature and or from patterns observed of the user.

Optionally, EEG data not related to a specific app activity type may be transmitted to the cloud by the application on the mobile device. It may be valuable to transmit EEG data to the cloud even if a user is not engaged in a specific exercise. If an EEG signal is being received by the device from a headset and if the EEG signal quality exceeds a minimum threshold while being worn by the user and if the user's privacy settings allow then EEG data streams are transmitted to the cloud using an activity type such as "No Prescribed Activity".

The app may provide for switching between available pipelines by receiving instructions from the cloud identifying a pipeline ID and associated pipeline parameters. The cloud server may analyze each activity type and determine which pipeline to choose for this user. The pipeline chosen may also depend on other information gathered from user's profile such as age and or as a direct response to survey questions or if a user suffers from a particular disorder. Other information that is used to fine-tune the algorithm pipeline is a history of the sessions of the user, including number of sessions, total number of session hours, time of day of session, session scores and results. Machine learning may be used to determine patterns across a user's sessions to change and adapt a particular user's pipeline. The cloud server transmits the pipeline ID to the device along with the learned parameters. In addition, the specific parameters of the pipeline can be determined within the device if disconnected from the cloud. If this is a first time user of the app then a default pipeline may be chosen for the user. The parameters for the pipeline or pipeline ID plus parameters may be sent to the user device. Again, the default pipeline parameters may be fine-tuned based on demographics or survey responses. The user can be part of an evaluation to select among a number of different algorithm pipelines. When a new pipeline is created for the user, the cloud may provide a new pipeline ID to be associated with the new pipeline at the cloud and at the client computing device.

Mobile Device Based Application—Processing at Cloud Server

Optionally, instead of the app applying the pipeline, the cloud may perform the pipeline processing. This may be achieved by selecting an option in the app for cloud-based pipeline processing. The cloud may store all of the information received from the mobile device in the user's profile in the cloud. The cloud may select the pipeline ID in accordance with the particular application. The cloud may maintain an association of one or more pipeline ID with particular applications or application types. In a typical pipeline the cloud server may apply Independent Components Analysis ("ICA") on the EEG signals to remove unwanted artifacts from the EEG signals. ICA may also be used to identify the source locations of EEG signals in the brain. ICA is computer resource-intensive and the cloud has significantly more computing power than a mobile device. The cloud calculates the parameters for this pipeline from the user profile that have been customized for this user and that have been adapted during any calibration of analysis of the user's particular bio-signal data. Any signal-processed data such as EEG band power calculated by the cloud is stored in the cloud per activity type. This information can also be sent to the mobile device app for storage in the mobile device user profile. The cloud may calculate feedback in real time using the pipeline defined by that pipeline ID. The cloud transmits feedback to the mobile device app. The feedback can also include instructions sent to the user from the cloud to the device so the user can be guided to improve a subsequent session.

The mobile app provides feedback to the user through visual screen graphics, audio or tactile feedback. The user receives feedback for each part of the user's session that is computed from the user's EEG signal. These computed results can be either aggregated across parts or across the entire session. These are stored under a session ID in the user profile associated with the app ID. If the cloud altered the user's parameters for a specific pipeline then the parameters are stored in the local user profile at the mobile device. Computed results can also have time stamps (or time codes) associated with them and the name of the parameter being computed (e.g. score is 192 at time 1:10). Results presented to the user are stored in the local user profile associated with the app ID, activity type, and session ID. The results may be filtered down to retain salient elements of an activity. The feedback can also include instructions sent to the user from the cloud to the device so the user can be guided to improve their subsequent sessions. This feedback can be kept up to date in the cloud as evidence grows and changes from literature and or from patterns observed of the user.

User Profile Data Structure

User profile data 114 may comprise, without limitation, raw collected data from the sensors, processed data, analyzed data, bio-signal data and non-bio-signal data, transformation matrices, algorithm parameters, and the data may be associated with time, and passkey or authentication data required to access the data or establish a connection between the client device and the SAAS platform 200.

Figure 6:
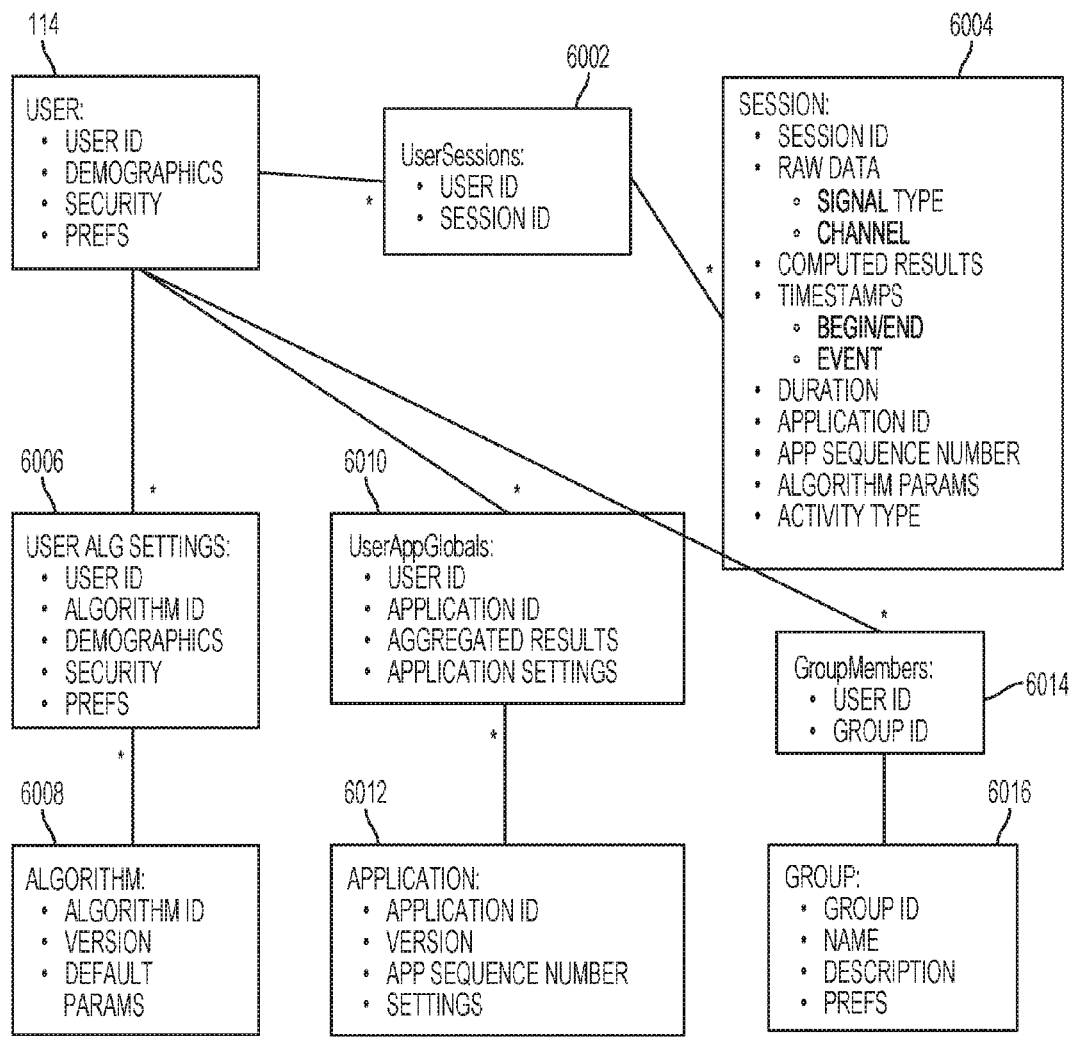
FIG. 6 illustrates an embodiment of a use profile data structure in accordance with the present invention.

An example of a possible user profile data structure 114 is shown in FIG. 6. The user profile data 114 may be described in a relational database structure, and may include the following data: user id; demographic data; security data; and preference data. The user profile data 114 may further link to or comprise any of the following data or data structures: user session data 6002 (including user id; session id); session data 6004 (including session id; raw data such as signal type and channel; computed results; timestamps (such as begin/end; and event); duration; application id; app sequence number; algorithm pipeline parameters; activity type); user algorithm pipeline settings 6006 (including user id; algorithm pipeline id; demographics; security; preferences); algorithm pipeline data 6008 (including algorithm pipeline id; version; default parameters); user app globals 6010 (including user id; application id; aggregated results; application settings); application data 6012 (including application id; version; app sequence number; settings); group members 6014 (including user id; group id); and group data 6016 (including group id; name; description; preferences).

The User ID 114 may be a unique number identifier that uniquely identifies a User Account. The demographics data may include gender, age, education, country, city, or other demographic data. The security data may include password and security questions. The preference data may include preferences for the display and User Interface, and other aspects of the application or system. The user profile data 114 may also include sharing preference data describing the policies of sharing data with others, and may be keyed to a separate table.

The User session data 6002 may include the user id and a session id uniquely identifying one session with an application.

The session data 6004 for each session id may be stored in a separate data structure. The raw data for a particular session may be a time-based (time-coded) series of biological data (bio-signal data) from one or more sensor types and the corresponding channels (e.g. EEG channel 2). The timestamps may be a time stamp (or time code) for each sample in the respective series for that session. The session data 6004 may also include time stamps of activity within a session describing the start and end time of an activity type within a session. The computed results may include scores or other results computed from the session data. The application ID may comprise a number that identifies a unique application (i.e. software program) that was used to create this session. The app sequence number may represent the sequence number that this app was used in a running total of session across all users maintained by the application. The pipeline parameters may include a pipeline ID which identifies the steps needed to process each different type of biological signal captured in the raw data. The activity type may describe each type of activity associated with the session. For example there may be a Calibration Activity Type within a Brain Fitness Activity Type.

The pipeline ID may include a user pipeline setting 1D of the algorithm pipeline settings may include a key to an entry in this table that defines an algorithm pipeline and its parameters to be used per application per user. The algorithm pipeline ID may further include an algorithm pipeline ID including an index or key to the algorithm pipeline table. The algorithm pipeline settings preferences may include algorithm pipeline parameters such that for each algorithm pipeline, a set of parameters may be used to specify the properties of each step in the pipeline (i.e. use a bandpass filter between 3 to 30 Hz).

The algorithm pipeline may include a name field including descriptive text of what the algorithm pipeline accomplishes, and may further include a steps field including descriptive text of the steps and their order applied of the pipeline. The version field may include a different number for each iteration of the pipeline. This version number can index old algorithm pipelines. The default parameters may define parameters for the algorithm pipeline when a person first starts using the algorithm pipeline.

The user app globals data 6010 may store any aggregated results or statistics across all sessions. The aggregated results may include total scores, badges, averages, total number of sessions, and other aggregated results. The application settings may include user-specific preferences for this application such as turn sound off, colour of display, and whether to store session data on the server. The set of algorithm pipelines may be customized per user per application.

The application data 6012 name may describe the application, and version may describe the version number of the application. The app sequence number may provide a total number of sessions run by this App for all users, and the settings may include global settings of the application for all users.

The group members 6014 may include a user ID which specifies a single user in the group specified by the group ID, and the group ID identifies a group of users.

The group data 6016 is identified by the group ID. The group data's respective name field provides text describing the group. The description field provides text describing the purpose and other details of the group. The preferences field may include whether the group is open or closed for other to join, and other preferences.

Encoding Methods

It may be beneficial to ensure time-locked fusion across sensors used in aspects of the present invention. Time stamps may be used for this purpose. Time stamps in the cloud could yield a reduction in compression or dimensionality by considering the joint space of many sensors. For example, encoding may be performed as a covariance matrix of a multitude of sensors and features. Time stamps may be assigned by the mobile device to brainwave data or any other measured or received data, and may be transmitted to the cloud server.

In the cloud algorithm pipeline, every stage may dump data into a high performance time indexed database Hypertable. Hypertable is an open source database system inspired by publications on the design of Google's BigTable. Data may be cached in random access memory ("RAM") (such as ring buffers) of the system platform or flash as arrays before being put into a database such that database read/write can be decoupled. This may allow each algorithm to grab the most recent and all the necessary history in order to work.

Data should be marked with the timestamp of when it happened as well as a timestamp of when it appeared or when it was ready. This allows for the creation and use of latency measures that are data dependent, and may be used to synchronize, calibrate, or relate clocks at the mobile device with clocks in the Cloud. As later information is calculated this can be inserted (for example, by time of occurrence) and be available for other processing.

A time stamp may also be used with a labeled epoch. The purpose of the epoch is to give a well-defined label to a section of data with sufficient length such that features of the epoch are discriminative. This may allow for efficient querying and retrieval of information. An alternative to epoch, may be a time series, with event markers in the data stream that assign labels to a range of times. Databases such as Hypertable may be used for querying time ranges and extracting records that can have label time span information stored within. Optionally, bracketing the windows may assist in finding the markers, in particular where a greater than zero time span is employed.

In a non-limiting example, row keys in a Hypertable may be sensor name, date, and time. To fetch data from a set of sensors for a range of time may be done as follows with the following query: SELECT*FROM SensorData WHERE ("sensorMUSE 2012-07-29 12:29:00"<=ROW<"sensorMUSE 2012-07-30 12:29:00" OR "sensorECG 2012-07-29 12:29:00"<=ROW<"sensorECG 2012-07-30 12:29:00").

Example Encoding of Brainwave Signals

In an exemplary, non-limiting implementation of the present invention, the mobile device may receive raw EEG data from the brainwave sensor (for example, the EEG headband) in real-time. Mobile devices, such as iOS-based devices may exhibit data bandwidth limitations. Some mobile devices may be limited to receive bluetooth data at 6 Kbit/s per second to 10 Kbit/s. A golem coding compressing method may be employed to improve the reliability of such data transmissions to the mobile device, and to achieve 256 Hz sampling rates. Ideally a slightly higher sampling rate would be desired as artifacts such as electromyography ("EMG") muscle noise generates significant power up to about 150 Hz (which would mean that a sampling rate of greater than 300 Hz would be needed to fully capture the signal). With 256 Hz sampling rate, the effective pass band goes up to about 120 Hz, which allows the presence of EMG signals to be discriminated within the EEG. Headsets that utilize a low sampling rate such the emotiv epoc (125 Hz) cause the EMG artifacts to masquerade as EEG, due to the limited passband, and make it hard to detect whether what is being measured is actually EEG or artifact.

A concern of having a reduced sampling rate is that the possibility of achieving a spike filtering method based on the specific pattern produced by motor unit activations in the frontalis muscles would become impossible, however at 256 Hz, the EMG spike profile still appears to be well-defined in a raw EEG time-series. With 4 channels of sampling at 256 Hz, artifact filtering methods such as spatial filtering determined through ICA or subspace reconstruction methods, are able to yield much better results than frequency based filtering, which is all that is currently available for single channel data.

The sampling rate is limited by the maximum bandwidth of the bluetooth channel. Should the bluetooth bandwidth of mobile devices increase, then it may be possible to achieve similar sampling performance to what is achieved on a desktop personal computer ("PC"). On a PC much higher sampling rates are possible, such as, for example a sampling rate of approximately 500 Hz. The higher sampling rates allow for improved performance.

Ten bits of precision per sample may be used to transmit a high quality EEG signal. The measurement noise floor may be designed to be equivalent to the least significant bit of the 10 bit Analog to Digital Conversion. The iOS platform has sufficient bandwidth at 256 Hz to transmit at 10 bits per sample ensuring high quality EEG signals.

The iOS compression method also reduces the precision of large signal swings, however, these are only produced when there is a problem with how the headset is being worn (such as being off the head, or having individual electrodes making poor contact). These signals may be primarily used to indicate to the user that the headset is producing poor EEG measurements. In testing, no loss in performance is created from this loss in fidelity.

Another effect of the low iOS bluetooth bandwidth is that the accelerometer data must be sent out at much lower rates than with PC use. This may limit some future methods that try to characterize complex movement of the head at the same time as brain-state classification. However for basic gestures, such as tapping, the accelerometer has onboard processing that eliminates the need for streaming the inertial data, and the data needed for cognitive training related measures such as posture tracking or breath/body entrainment, fits, along with simultaneous EEG, within the iOS bandwidth limitations.

EEG Headset Data Compression Technique

The compression will be broken down into two steps. In the first step, a differencing method may be used to reduce the numerical size of the data. The differencing method may comprise an initial data value in the packet being sent without compression. The subsequent value may then be different from its immediate predecessor. For example, dataset [20, 18, 11, 16, 16, 10, 4, 15] translates to [20, 2, 7, −5, 0, 6, 6, −11].

In the second step, the difference data is then sent using a special dynamic size. A median for the differences will be found and then the difference data will be broken into three chunks. The chunks will be the quotient, remainder and sign of each difference point.

The first chunk will be the quotient of a division from the absolute median converted to unary code. Using the above example, the absolute median difference is 6. For the purposes of the compression all differences will be taken its positive form. For example, [2, 7, −5, 0, 6, 6, −11] will have quotients of [0, 1, 0, 0, 1, 1, 1].

Unary Code is a simple bit representation of the number with 1's indicating it's size. Unary Code of 5 is 111110, 1 is 10, 0 is 0.

The second chunk is the remainder from the division of the difference by the median. This is also a dynamically sized value using Truncated Binary Encoding. Again using the sample above we have another set of data with varying remainders. For example, [2, 8, −6, 0, 6, 6, −11] will have remainders of [2, 1, 5, 0, 0, 0, 5].

Truncated Binary Encoding allows some remainders to be expressed with 1 less bit than the larger remainder values.

Using an example of a median of 6, following ceiling of log 2(6) we know a bit number of 3 is required to represent 0-5. 3 bits have 8 states, therefore 8-6 is 2 free unused states in 3 bits. This means we can represent the number 0 and 1 with 1 less bit than 2, 3, 4 and 5. We do this by converting 0 and 1 to simply 00 and 01 respectively. However bits 2, 3, 4 and 5 are translated up by the free state amount of 2. Therefore, 2 is 4, which is 100 and so on. For example, 0:00; 1:01; 2:100; 3:101; 4:110; and 5:111. Note that starting with 1 indicates that the value is not 0 or 1 ensuring all 3 bits included.

To indicate how this might work for various other examples of 11, 23 and 9 follow.

For the 11 example: 0:000; 1:001; 2:010; 3:011; 4:100; 5:1010; 6:1011; 7:1100; 8:1101; 9:1110; and 10:1111.

For the 9 example: 0:000; 1:001; 2:010; 3:011; 4:100; 5:101; 6:110; 7:1110; and 8:1111.

For the 23 example: 0:0000; 1:0001; 2:0010; 3:0011; 4:0100; 5:0101; 6:0110; 7:0111; 8:1000; 9:10010; 10:10011; 11:10100; 12:10101; 13:10110; 14:10111; 15:11000; 16:11101; 17:11110; 18:11011; 19:11100; 20:11101; 21:11110; and 22:11111.

As shown the values of reduced size vary based on the individual median. The median is chosen over the mean to implement the maximum number results expressed as 0 in Truncated binary as well as only 1 in Unary, in the above 3 examples the value would be 10000, 100000 and 10000 respectively. The final chunk is simply the value sign. If the difference is negative the bit is 0 and if it is positive the bit is 1. The entire sample will then be a Unary Code, followed by a Truncating Binary Code concluded with a sign bit. Each data set can vary in size as necessary for transmission as well as compression.

As a countermeasure to large quotients from unexpected outliers a simple dynamic encoding called Elias encoding is used. A Unary of 15 indicates a value larger than 14 quotient. This is followed by Elias encoding of the number, which is done through 0's leading to the binary number indicating it's size (i.e. 5 in Elias would be 00101, 85 would be 0000001010101).

The whole sample of 85 would be 111111111111110000001010101 instead of 85 1's.

The packet design structure may include a sync byte (0xFF 7002); counter 7004 and type (1 byte); 1 byte per median (4 bytes); length (2 bytes); checksum (1 byte); and sample difference data, 6 samples at a time, each channel after the previous (size varies). In general, each packet may include a 9 byte header followed by a variable size of the data set of 24 samples, 6 samples from 4 channels. The Median may allow the other side to interpret the results.

As a final measure of data transmission size a method is used to avoid sending data with large variances in the signal. If the median of the differences between the data neighbours exceeds 30, all differences are sent as a 0 difference. This makes the transmitted signal a set of 0 differences resulting in a flat line where bad data is present. Optionally, a full absolute packet may be sent following the first good data packet to realign the absolute values for the individual channels.

Figure 7:
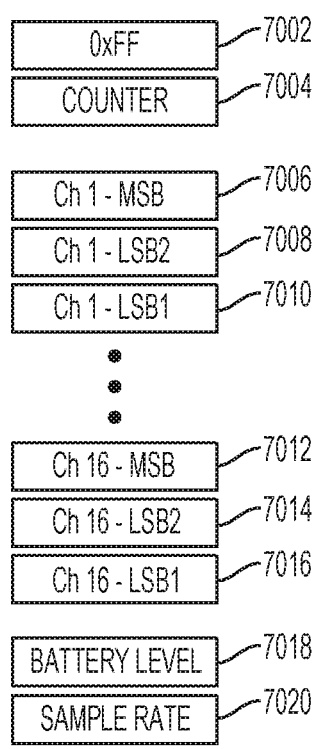
FIG. 7 illustrates an embodiment of a sensor data packet in accordance with the present invention.

The sensor device (EEG headband) may use a standard Bluetooth RFCOMM (serial port protocol) channel to transmit the raw EEG signals. The data may be continuously transmitted as soon as a Bluetooth connection is established with a host. The system outputs data at a sample rate 7020 of 125, 250 or 500 Hz. Each sample may contain 52 byte worth of data that includes a header, 16 EEG channels and a tail. FIG. 7 shows a representation of a sample packet structure as transmitted from the sensor device.

The packet starts with the byte '0xFF' 7002 for synchronization. No other byte in the packet can have the value 0xFF 7002 by design. The second byte is a counter 7004 that increments from 0 to 0x8F.

Each EEG channel is a 24-bit sample that is broken up into 3 8-byte chunks with the most significant bit ("MSB") first (e.g. 7006, 7012), the middle least significant bits ("LSB"s) (e.g. 7008, 7014) and the smallest LSBs (e.g. 7010,7016). The 24-bit 2's complement value can be reconstructed as follows:

The 24-bit sample can be converted to raw EEG (in volts) by: $EEG = sample/2^{24}$.

The second to last byte is a 7-bit value representing the battery level 7018.

The final byte indicates the current sampling rate: 0-500 Hz, 1-250 Hz and 2-125 Hz.

Definition of System Platform Pipeline

The processing, analysis, and classification of brainwave data may be performed in real-time. That is, data may be processed, analyzed, and categorized as it is received from the sensors. Optionally, the results of the analysis may be used to provide feedback to the user through the user effector 110. For example, analyzed data from one or more sensors might be analyzed to determine that a user is outside of a desired mental state, and the system platform can use the user effector to assist the user in achieving the desired mental state. The processing, analysis and categorization of sensor signals is done by a system platform pipeline.

The data may be stored or otherwise associated with a user profile 114. This user profile 114 may be stored, for example, on one or more client devices in the trusted network 113, on a single client device 108, on a local server, on a cloud-based server, on a SAAS platform 200, or some combination thereof. Multiple user profiles may be stored in a respective data store, regardless of whether the data store is on a client device, a local server, a cloud-based server, a SAAS platform 200 or some combination thereof.

The pipeline may exist in the mobile device and in the cloud. At the mobile device, the pipeline may be tuned for the mobile device's computational resources and application needs. The sensor hardware may perform sampling; time stamping; and encoding of data for wireless transmission including pre-filtering (such as anti-aliasing, noise shaping, etc.) and compression methodologies, to minimize the information loss at different levels of bluetooth bandwidth. The mobile device, which is the recipient of sensor data, may perform noise identification (such as spatial filtering and classification to determine ideal denoising practices); denoising (such as linear subspace methods, wavelets); spatial filtering, determined using techniques such principal components analysis, blind source separation (such as ICA), maximum noise fraction ("MNF"), common spatial patterns; band pass filtering; and adaptive algorithms in the time domain or feature domain (such as adaptive whitening).

At the cloud, more advanced feature methods may be performed that may be too computationally intensive or complex for performance on a mobile device. For example, empirical mode decomposition ("EMD"), ensemble mode decomposition ("EEMD"), or scattering wavelet transform (see Stephane Mallat, "Group Invariant Scattering", 15 Apr. 2012, web: http://arxiv.org/pdf/1101.2286.pdf, the entirety of which is incorporated by reference). These advanced methods can yield highly discriminative features that can yield much better machine learning performance through greater separability, and reduced search spaces through filtering or built in invariances (such as in the scattering network transform). Resulting discovered patterns can then be discovered in the data using simpler methods once we know what we are looking for. A secondary process may be included in the pipeline to transition from discovered patterns to more computationally efficient but adequately performing alternative analytical methods.

A pipeline in accordance with the present invention may specify the components and the order in which a biological signal is processed, analyzed and interpreted. There are four major categories of components in the pipeline: signal processing, feature extraction, feature selection and prediction models.

Client side processing of the data may be tuned to conserve on compute operations due to the battery and other resource limitations of mobile devices. Offline cloud methods may run many different pipelines and select a highest performing configuration (in terms of classification performance) and provide pipeline parameters to the client. Pipeline selection utilizes feature selection methods such as stepwise regression or mRMR, or wrapper methods that estimate a classifier based on selected features are part of the feature selection methods.

Determination of correct data labelling may be a critical part of estimating the optimal pipeline. The cloud methods are constructed to utilize map-reduce to parallelize estimators and estimate the most likely result based on all methods. Best estimates of class labels are fed back through system to denoise data (such as trim outliers, etc., for methods that are prone). MapReduce operations may be used to distribute signal across feature methods, and features across classifier methods.

Constraints relating to the real-time computational resources are introduced into the feature selection process to ensure that the resulting real-time estimators are runnable on the target platform. Parameters will be platform dependant. For example, an application running on an iphone3 will have a different constraints than and iphone4 which will have different characteristics than a desktop computer.

Pre-Processing or Signal Processing

The system platform may preprocess the raw collected biological and non-biological data 112. This can involve, as non-limiting examples, interpolating gaps in signals, noise identification, noise filtering, spatial filtering, band-pass filtering. Other solutions may be employed for handling issues related to signal collection and transmission.

Signal processing is a broad area that refers to mathematical methods of extracting or transforming signals. The goal is to pre-process the signal to remove unwanted noise and artifacts or to focus on a narrow frequency bands of interest.

Signal processing may include: filters (frequency response characteristics) (may include: low pass; high pass; and bandpass); order of filters; artifact detection method (common spatial patterns, Threshold (e.g. log bandpower, signal power), high frequency EMG with spatial patterns, off); artifact removal method (ICA, repair bursts, ignore sections with artifacts); resample rate; EEG channels to use; electrode referencing scheme (average reference, specific electrode, linked mastoids); data cleaning (remove flatlines, remove broken channels, remove spikes or bursts); baseline removal (off or on); and window definition (size and increment).

Feature Extraction

The pipeline may use the preprocessed data to extract features from the signal. For example, this may be done be done through linear projection (such as Short-time Fourier transform, "STFT") of the EEG signal or non-linear functions (such as fractal dimension) of the EEG data. The resulting feature space may have greater or lesser dimensions than the original data. This projection may aid in the classification of the collected data, for example, by increasing the separability of classes.

Examples feature methods used by the system (operating on original signal or features of the signal) may include: short time fourier transform; wavelet; AR model coefficients (auto regressive model of the signal); Non-linear complexity features such as fractal dimensions (Hilbert transform); ensemble empirical mode decomposition; signal derivatives; and regularized covariance matrix estimation (such as ledoit wolfe estimator).

Feature extraction is also a form of signal processing, however the goal may be to extract features that are useful for machine learning to build prediction models.

Frequency domain signal processing may include: fast fourier transform ("FFT"), wavelet or Hilbert; kernel definition (Hamming window, wavelet type); power spectrum; power per EEG band; power variance per EEG band; peak frequency within a particular band; and phase differences across electrodes within EEG frequency bands.

Time domain signal processing may include: window sub-segments; voltage or signal power thresholds; and quantization or discretization thresholds to encode continuous feature value to discrete value.

Transforming data to extract features may be accomplished at least by using principal components analysis, linear discriminant analysis, eigen decomposition, and/or whitening transformations.

Feature Selection (Feature Adaptation)

An observed problem with BCI technology is that methods that are derived from training data tend to be inconsistent in their performance and often get worse as the user uses them. A primary case of this is the covariant shift in the features with respect to the user response classes. Three main strategies are used in the system to reduce this effect: (1) server side algorithm improvement methods are run to update the client's algorithm pipeline and parameters per-session or as needed; (2) online covariance matrix estimation and subsequent whitening using this estimated covariance method (covariance matrix estimation is regularized to improve on stability); and (3) online detrending of features using fitted models such as low dimensional polynomial.

Prediction Methods

Parameters for prediction methods may be developed by machine learning in the client or in the server. Machine learning done in the cloud can send parameters to the prediction model in the client. Parameters discovered in the client can be sent to the cloud to be stored in the user profile there. The pipeline may then classify the extracted features of the data. This classification may provide an indication of the mental state of the user (e.g. a meditative state). Various algorithms 116 can be used to classify the features determined in previous stages. For example, a minimum mean distance classifier or a K nearest neighbours classifier may be employed to analyze the data.

Prediction methods may provide for: estimation of hemispheric asymmetries and thus facilitate measurements of emotional valence (positive vs. negative emotions); better SNR for global measurements and thus better access to high-beta and gamma bands (fast oscillation EEG signals), which is particularly important for analyzing cognitive tasks such as memory, learning, and perception (it has also been found the gamma is an important neural correlate of mediation expertise); noise reduction; integration of data from other devices and synchronization of events with brainwave data to aid in context aware analysis as well as storage and future analysis; time locked stimulation and analysis to support stimulus entrainment ERP analysis; and data prioritizer that maximizes the amount of useful information obtainable with an incomplete data download (i.e. data is transmitted in order of information salience).

These prediction models are developed using machine learning methods, of which learning types may include: linear discriminant analysis; support vector machine; decision tree; K nearest neighbour; pattern discovery; Bayesian networks; and artificial neural networks.

Client-Side Rules Engine

The client computing device may implement part of the pipeline through a client-side rules engine, which may be provided in computer hardware or computer software. The rules engine may: choose configurations of the pipeline; manage adaptation of particular elements (e.g. feature bands, reward levels, etc.); manage the user profile; manage or provide context switching; manage or provide context estimation; determine what data is to be transmitted or saved; determine which devices or users any bio-signal or non-bio-signal data may be provided to; determine what results are presented to the user; control the data that is provided for analysis by the pipeline; decide on context based on a classifier (such as a decision tree where context and confidence in class is used to decide which rules to use); control what sensors to use; determine a learning goal; and determine what pipeline to use. The rules engine may be configured to know what sensors or other resources are available, a context estimate, and application needs.

Figure 8:
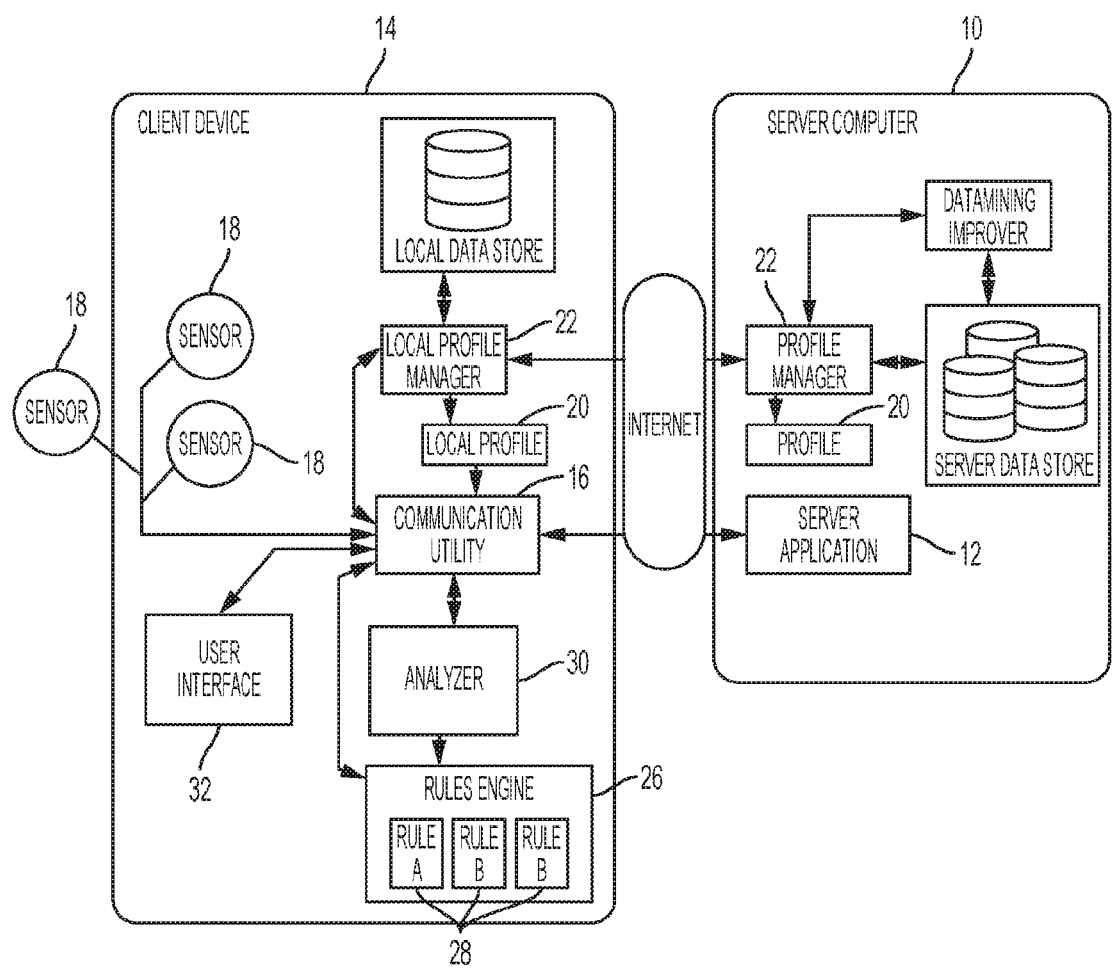
FIG. 8 illustrates an embodiment of the platform in accordance with the present invention.

A client-side rules engine 26 may be provided in the mobile application, as shown in FIG. 8 in accordance with a non-limiting exemplary implementation of the present invention. Rules are loaded to the app from the cloud (server computer 10). The rules engine 26 may choose which pipeline that the analyzer 30 will apply to which sensors 18 of a specific user. The rules engine 26 may provide rules 28 that use the context of the user (i.e. emotional state, global positioning system ("GPS") coordinates, time of day, open apps on the device, prior goals that the user has stated) to determine how to analyze the sensor data (i.e. which algorithm pipeline to apply to which sensor). The rules engine 26 may also have rules 28 to determine which results are displayed and or stored locally on the client 14 and which are stored in the server 10.

Rules engine inputs may include: local user profile; and local app information (such as status (ON or OFF) identifier, parameters). Rules engine outputs may include: pipeline ID; which user data to send to user actuators; which data to save locally; and which data to transmit to the cloud.

The app may include a communication utility 16 which is a switch that routes which sensor data is sent to the analyzer for analysis by the pipeline. It also switches which subset of the processed data is sent to the user interface. Communication utility 16 inputs may include: encoded sensor data, local profile manager, local profile ID, pipeline ID.

Local profile manager 22 may manage the user's profile at the mobile client device 14.

There may be an interface from the rules engine 26 to each app operating on the mobile device 14. The rules engine 26 may be an app that runs across all other apps that helps the user reach some goals.

In a non-limiting exemplary implementation, rules engine 26 may be used in an audio environment manager. The rules engine 26 may assist in choosing music based on the user's mood, or determine a user goal based on what is the person doing (i.e. exercising, working). If exercising the goal may be to boost energy. If working the goal may be to cultivate a state of stable high attention.

If the user receives a phone call then the rules engine may switch the music off or modulate music lower volume of change the frequency response of the music. If the user receives a phone call then the rules engine 26 may switch the music off or modulate music to a lower volume of change the frequency response of the music, to reduce stress to the user. If the phone call is a conference call, the user is wearing earbuds, and a microphone array is present in the room, based on the attention that the user is placing on another participant in the room a beam former chooses which audio components to enhance and which to suppress in order to maximize the quality of audio received from the person or device in the room that the user is paying attention to. This is useful in an environment where multiple conversations are taking place and the user has difficulty sorting out the noise from the signal he/she wants to hear.

The client side rules engine may choose which workflow to apply based on the conditions that exist when an app is executing. A pipeline may be selected that the analyzer will apply to sensor data of a specific user. The conditions of a rule can include the context of the user (such as brainstate, activity, prior goals that the user has stated, GPS coordinates, time of day, open apps on the device) to determine how to analyze the sensor data (such as which algorithm pipeline to apply to which sensor), and to determine which results to display and/or store locally on the client and which are stored in the server.

The client side rules engine provides overall management of a person's experience and what is learned about them by specifying workflows. The following example data provides an example of rules in the rules engine that specify which work flow to use depending on the context that the user is faced. For example, a Condition might be "Activity Type=Working Alone on a Project" and the corresponding Workflow might be "1, Enhance Mental State A (e.g. creativity, attention)". For the condition "Activity Type=Interacting with Son", the corresponding workflow might be "2. Enhance Mental State B (e.g. empathy, attention)". For the condition "Activity Type=Interacting with Person That is Angry", the corresponding workflow might be "3. Enhance Mental State C (e.g. mindfulness, stress relief)"

These examples show that the user has different desirable mental states that she wants to achieve depending on their context (i.e. condition). When a condition is true, the workflow associated with the condition is executed. In these examples, activity type is a field in the user's profile that has a series of timestamps associated with that activity type. The workflow #1 includes real-time elements that specify which pipeline to use, which information to feedback to the user. In addition workflow #1, specifies a machine learning approach. It states the method as to whether supervised learning or unsupervised learning is to be applied. If supervised learning then workflow #1 also specifies the method used to label sections of biological signals and the pipeline(s) needed to extract features, the metric to determine performance and any measures or signals not to consider in the machine learning workflow.

An example non-limiting message flow involving the client side rules engine will now be described. First, the user's calendar indicates that the user has scheduled time to work alone on a project. When the scheduled time occurs, the calendar on the User's mobile device asks for confirmation that this task is still occurring. Second, the User responds Yes. The User connects the user's EEG headset to the Mobile Device via Bluetooth. Third, the Mobile Device populates the Local User Profile "Activity Type" for each timestamp associated with this task as "Working Alone on a Project". The Rules Engine is looked up and there is an entry in the Condition part of the Rules Engine corresponding to "Working Alone on a Project". The Rules Engine executes Workflow #1. Fourth, Workflow #1 launches an APP on the Mobile Device that gives feedback to the User when they are in a mental state that maximizes creativity. The APP loads the algorithm pipeline associated with enhanced creativity. While working the User experiences a creative breakthrough and taps a button in the APP to indicate this. The APP loads the User profile Activity Type with "Creative Breakthrough" at the timestamp when the User tapped that associated button. The APP transmits contents of the Local User profile to the User's Cloud Based User Profile.

Pipeline Analysis Improvement

In one implementation, the system platform implements a series of different pipelines, and the system platform is configured to operate adaptively based on individual attributes of users by (A) identifying an individual user and their intended use of the system (e.g. identifying the specific application linked to the system that the individual intends to use), (B) accessing the user's profile, (C) accessing rules for selecting one or more pipelines in order to improve operation of the system based on the profile (for example based on one or more criteria such as responsiveness, accuracy in determining a physical or emotional state of an individual user, etc.), and (D) applying the selected pipelines to operation of the system platform for the user. A skilled reader will understand that the one or more pipelines that will provide effective use of the system by an individual user may vary over time (for example as a user improves their ability to interact with a meditation training application that utilizes the system of the present invention). Also, different applications may be linked to the client computing device, and the user may begin using different applications at different times, and data sets may be acquired over time.

One contribution of the invention, is a system platform architecture design that expands the ability to extract training data across a range of different applications that are linked to the system, and analyze the training data and immediately improve the operation of the system for a particular user based on the resulting analysis data, again across a range of different applications linked to the system. This minimizes the efforts, number of steps, and time required to train different applications to function based on relevant features or attributes associated with an individual user, and also enables the system to correctly adapt to changes in these features or attributes over time. These contributions provide an effective solution to obstacles in adoption of applications by users. Prior art systems do not provide a mechanism to leverage understanding of an individual, developed through their use of one application, to other applications linked to a BCI system. This limits the ability of prior art systems to interact with users in a seemingly "intuitive" manner, and requires users to in effect duplicate system training efforts. The present system platform on the other hand, through at least the rules engine, reflects understanding which may evolve over time of the relationships of training data for one application and the relationships of training data for another application. This enables the adoption of applications, and the completion of the training phase for particular applications, to be streamlined. User adoption and user engagement may also be improved.

Customization of Pipelines on Per-User Basis

Another method of learning models that can be used by algorithms to drive applications is to customize the algorithms on a user by user basis. There are two categories of customizing algorithms per user. One category of customization is done with active engagement of the user and the other does not need active engagement of the user.

Cloud based extensible user profiles for personal information may be provided. Settings and pipeline parameters that are continuously or periodically tuned (through the use of the application) to be improved or optimized for the specific user may be provided. Hardware setups and application-specific parameters may be provided. Relevant training data may also be provided. This will allow application usage to be device independent, and allow for back compatibility as the application is improved.

The present invention may provide for customization of pipelines with the user's active engagement. EEG data is acquired and stored in the cloud whenever an application is used. Each session of an application has statistics, results and or scores associated with each session. A milestone achieved by the user can be defined in a number of different ways such as number of sessions completed, exceeding a score consistently or number of hours in total across all sessions or the user is struggling to reach a milestone. After a milestone is reached, an opportunity to customize their algorithm is offered to the user. If the user accepts then two (or more) new pipeline variants are generated. The variants can be based on new models of new features (such as new frequency bands) that are correlated to scores. The user then repeats 3 brief exercises (e.g. 2 min.) where each exercise uses the 2 new pipelines plus the old pipeline. The user rates each session and the best performing pipeline as per user preference is kept. The user is asked to rate which pipeline worked best. No final score may be presented to the user however a running line of the user's score is presented while the exercise is underway. Objective scores are calculated and compared to the user's subjective experience. This is repeated for each new pipeline and existing pipeline. The pipeline preferred by the user is then kept.

A different option of pipeline evaluation by active user engagement asks the user to try different strategies to get a high score per exercise. The different strategies can include loving-kindness meditation, breath anchor, counting breaths, body-scan, listening to guided exercises, listening to different types of music, CBT exercises, etc.

The user is asked to rate what strategies worked best. These results are kept in the user profile as features to be used in subsequent algorithm improvement data mining operations as well as provide relevant data for population demographics related to brain-type and learning strategies within the particular applications context. Other users benefit by receiving more appropriate suggestions to improve their own performance based on this statistical data.

The present invention may provide for customization of pipelines without the user's active engagement. With this method of evaluating new pipelines, variations are applied to the pipeline to see if and how the user's performance changes. The pipeline is changed gradually over time. If the user consistently improves then the new pipeline is kept.

An example of personalized pipelines may include adaptive pipelines. Each user's brainwaves are different and therefore require different tunings for each user. A user's profile consists of brain signatures unique to each user that have been derived by the pipelines using real-time behavioural and environmental information captured simultaneously (and time locked) with EEG, as well as the user's classification of the user's current mood, emotion, opinion, etc., at the time the EEG data is acquired.

The combined data may be used in a semi-supervised machine learning process to discover unique brain signatures that enable interaction with applications. The user profile is dynamic and changes over time as more information is gathered and as the user's skill grows. Brain signatures captured in a user's profile can be reused in other applications. Also the use of other applications are additional opportunities for fine-tuning a user's profile. A user's profile is built so that the learning curve for interacting with a brainwave enabled application will be reduced. This will improve adoption and frequency of use of brainwave enabled applications.

The user profile may speed up the adaptation for an existing user when the user uses a new application, through the significant amount of prior knowledge of the user brain characteristics, or brain signature, have been collected through the use of other applications.

Machine learning is used to discover brain-signatures on a per person basis across a number of their sessions. Brain signatures will be discovered based on features extracted through analyzing EEG signals of a user participating in prescribed exercises plus the other data mentioned in the paragraph above. Brain signatures will get more and more refined as the number of sessions that a user participates increases. Brain signatures can be used to provide quantitative and or qualitative real-time or post-session feedback to a user in a number of ways such as a score of their skill level or as input to a game that increases a gaming parameter in proportion to the brain state at a given moment in time (e.g. speed of a race car). It may also be possible to provide advanced users with feedback on their brain-signatures and how they relate to the scores they receive.

Before customization on a per user basis can occur, generalized pipelines are built based on a large number of users. Machine Learning is applied to this data for the classification of brain states through the use of labeled data to train algorithms. Once this generalized pipeline is built it can be adapted to specific users and adapt as the user's skill improves. Brain training exercises based on evidence found in the literature and confirmed by testing with in-house experiments are used. User testing is conducted to gather labelled training data. With tight control of the experimental conditions, the system platform can map the basic sources of variation to determine the general signal characteristics of the target brain states of interest. This allows creation of models and general foundation algorithms that can seed and stabilize the user specific classification and adaptation methods. A growing collection of EEG data in user profiles from increasing number of apps and users stored in the Cloud will allow further enhancements to generalized pipelines.

Data that is gathered through app usage is combined with other sources of data (biological data and non-biological data such as: behavioural information, demographic information, answers to surveys or formal questionnaires other user entered text) and will be used to do cross-population studies for the refinement of generalized algorithms across a large number of users and may be fine-tuned to specific demographics or based on characterization of brain types using EEG signal analysis of users doing prescribed exercises (e.g. experienced meditator versus novice). Anticipated refinements would yield higher performance, quicker adaptation, and greater consistency across the user spectrum.

A non-limiting example method for the creation of an initial generalized pipeline is described. First, controlled experiments are conducted where test subjects are subjected to appropriate stimuli and goal oriented tasks, such that their bio-signal data can be labeled. Second, brain features are computed using pre-processing and feature extraction methods that have been successful in other applications. Third, machine learning methods are employed to discover a generalized predictive model.

Pipelines are intended to be used for real-time feedback. Another non-limiting exemplary method used is described as follows. First, controlled experiments are conducted where test subjects are subjected to appropriate stimuli and goal oriented tasks and sham feedback, such that their bio-signal data can be labeled. Second, brain features are computed using pre-processing and feature extraction methods that have been successful in other applications. Third, machine learning methods are employed to discover a generalized predictive model. Typically a number of different supervised learning methods to the data features (usually choosing the methods that produce the highest performance using cross validation). Fourth, apply the classification on-line, with the addition of similar on-line detection and removal of artifacts from the EEG. The system platform may then replace the sham feedback with feedback based on the classification and repeat the process.

A brain signature is a set of features that are collected, quantized and stored as a multidimensional histogram, and is part of the user's profile, that is used in conjunction with a set of algorithm pipeline parameters to classify the user's state (user response classification).

A covariance matrix of features is a special case of this histogram and is an embodiment of the brain signature. Typically the brain signature used in the client is a covariance matrix of the subset of features that are most salient given the computational resources of the client device that are available for feature extraction and classification.

For a new user a generic brain signature is used to initialize each user's profile and classification parameters. As an individual uses an application, their collected features are used to further populate the feature space, building on the generic algorithm and to allow for the optimization of their classification parameters.

Updates to user's brain signature can be applied both on the client device as well as on the serve. Updates on the client side are typically done on-line to optimize the real-time performance (e.g. to sustain or improve the performance across a session).

In one embodiment, the system platform may add a forgetting factor to the histogram accumulation process to allow for adaptation to the covariant shift that is experienced in the variables as the user learns. In most cases the system platform does not forget the histogram initialization, in order to stabilize the adaptation.

In another embodiment, all of the data that has been transformed into the histogram space, are stored individually as a multidimensional time series, and the covariant shift of these features are is estimated using a model predication, such as a low-dimensional polynomial model.

Collected user data is aggregated on the server such that a more comprehensive learning process may be applied such that the user's base model (base model is the feature axes of the histogram, or in the case of a covariance matrix brain signatures, the base model would be the set of features that the client pipeline estimates.) can be updated to improve the fit of the model to the user. These full data methods are run on the server because of their complexity and to add value to data uploads for the user. It also allows for interesting analytics to be provided back to the user through a web-portal.

Pipeline/Algorithm Improver Implementation

Figure 12:
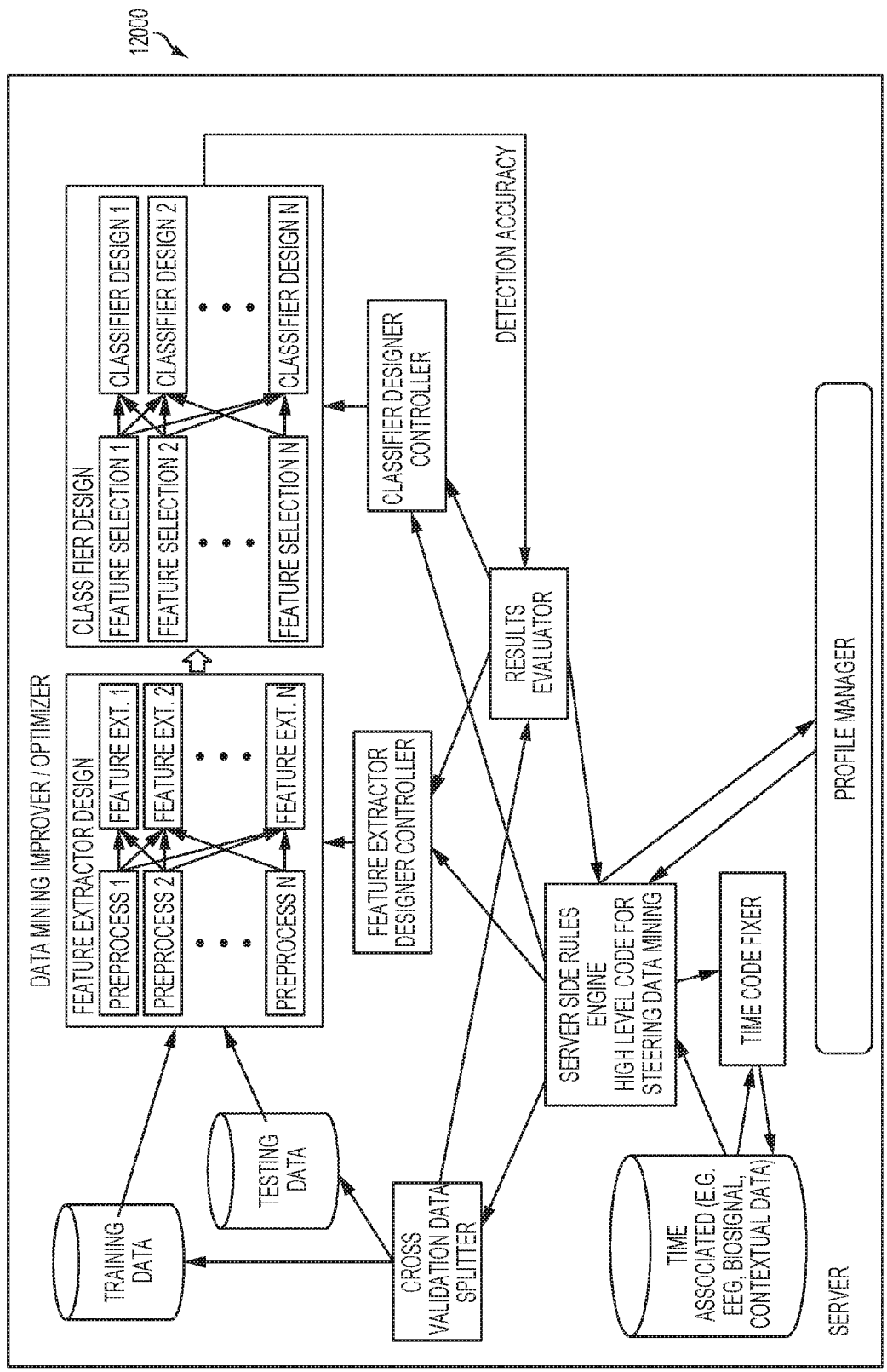
FIG. 12 illustrates a data mining improver and/or optimizer in accordance with the present invention.

FIG. 12 shows an example of a data mining improver/optimizer 12000 in accordance with the present invention. Client side processing of the data will often be tuned to conserve on compute operations due to the battery and other resource limitations of mobile devices. Offline cloud methods will run many different pipelines and select highest performing configuration (in terms of classification performance) and provide pipeline parameters to the client.

The cloud methods and data storage are optimized to utilize parallel computing methods such as map-reduce to parallelize pipeline development. E.g. Map operations distribute time contiguous raw data across workers; these raw segments can then be mapped across feature computation workers. The various feature types computer from the data is collated and redistributed to feature selection and classifier design (machine learning) processes.

Some important features of the non-limiting implementation may include: time code fixer; rules engine; feature extraction; feature selection; supervised machine learning; and parallel methods for cluster/grid computing for algorithm improver.

The TIME CODE FIXER/signal synchronizer method may evaluate the time offsets needed for synchronization of client devices with the rest of the platform and to correct for unknown time offsets and non-uniform sampling.

The RULES ENGINE may supervise (and provide an interface to) the operation of the data mining methods that are run on the user data.

The FEATURE EXTRACTION may include PREPROCESSING (multiple methods considered to find the most optimal combination); FEATURE EXTRACTORS (Employ more advanced feature methods that may be too complex for client device computation); and UNSUPERVISED MACHINE LEARNING (automatic data driven feature extraction, Pattern discovery, K-means clustering, Hierarchical Generative Models such as Convolutional Deep Belief Network).

The FEATURE SELECTION may include selection of feature subsets before machine learning to improve on convergence and reduce prediction error due to noise.

The SUPERVISED MACHINE LEARNING may provide for a determination of correct data labelling, which is a critical part of estimating the optimal pipeline. The multi-method approach that is used for pipeline improving can generate more accurate (less noisy class labels). Aggregate results (the most likely result based on all methods) are fed back into the Time-Series database in the form of class belief columns, best estimates of class labels fed back through system to denoise data (trim outliers etc. for methods that are prone). The supervised machine learning may also provide a method for converting computationally intensive feature methods to pipelines that can be executed on the client device. Once patterns are discovered, its typical that computationally efficient but adequately performing alternatives can be found. A primary benefit of the more advanced features is to make the machine learning problem more tractable.

The PARALLEL METHODS FOR CLUSTER/GRID COMPUTING FOR ALGORITHM IMPROVER may provide Methods for operating the pipeline/algorithm improver utilizing parallel computing methods to capitalize on cloud cluster/grid computing architecture.

The TIME CODE FIXER may correct time codes. Each computer or device in a network may have a time source that is not synchronized with the other components in the network. We want to timestamp every sample (e.g. EEG or ECG or camera or thermometer etc.), each signal can be thought of as a series of samples at a discrete point in time where each sample has a corresponding timestamp. The timestamps across all of these samples from different sensors need to be synchronized for us to derive correlated pattern information.

An exemplary non-limiting Message Flow for Timestamp is described, in the context of an Augmented Reality Example. It may be desirable to estimate the emotional state of the user but using an input from another system. For instance, User A is talking to user B, User B is using a video camera and is streaming the live feed to the internet. The video feed is available to user A through the system platform, where video analysis can be done by cluster or grid computer. User B is pointing the camera at user A, and thus the processed video contains features of facial expression of user A as well as features related to their body language. User A is using the cloud platform to estimate the user's bio state for the purpose of tracking the user's cognitive and affective state as a means of ameliorating the user's depressive symptoms. With the included access of video features, user A has access to better brain-state estimation using the joint signal space. Time stamping (in the same time base of user A) of the source video and of the derived features is important to be able to do the joint estimation. The system platform may consider the architecture and method so that the above is feasible in real-time or a near to real-time as possible. For example the video features may be available at a later time than the other features because of the requisite processing and possible internet delays. At the very least the system platform may have to wait for the video, or the system platform may need to be configured to estimate using what is had, and then improve the estimate when receiving the video. This may be similar to doing inertial tracking of video and then doing drift correct using image based tracking.

Time coding may present various problems. For example, specific sensors or pipelines (feature or classifier) may have uncertainty in when exactly things happen. The system platform needs a way of encoding uncertainty in time. Quantization of time may be performed with coarseness based on uncertainty. The uncertainty window/confidence interval may be in the time stamp record.

Different data sources may also have different times. The system platform may synchronize clocks by having components of the system platform send times back and forth until an adequate estimate of the network delay can be estimated and then the system platform can estimate the clock difference (for example, by NTP or computation the round-trip delay time and the offset). Given a history of clock offset measurements between two computers, the timestamp of a remotely collected sample can be remapped into the mutual time domain.

While the system platform may not have a way of keeping time, the system platform may perform synchronization later based on information in the signal (for example where there is EEG data of a user's blinking and video data of the user's face with blinking is also provided, the system platform may sync the video to the EEG data).

Non-uniform sampling, and missed samples may occur. Missed samples are fixed using packet numbers if they exist, otherwise advanced methods need to be used. In some cases, like where data has chunks missing, we may use computation of a simple time shift use Euclidean distance over the time series. This may be done by doing window based Euclidian distance minimization, using cross correlation. Subdivision methods may be used by the system platform to narrow into finer timescales.

In more difficult cases of non-uniform sampling, the system platform may use dynamic time warping (though other methods are possible). A dynamic time warping ("DTW") algorithm may calculate the distance between each associated pairs of two sequences in order to minimize the distance. To manipulate this algorithm, dynamic programming is applied to find the least expensive path through a cumulative distance matrix. For multi-dimensional data, the system platform may use multidimensional dynamic time warping ("MM-DTW"). This pipeline utilizes all dimensions to obtain the optimal path and aligns multiple signals simultaneously. After alignment, the regular similarity measurement can be used to these aligned signals (see Parinya Sanguansat, "Multiple Multidimensional Sequence Alignment Using Generalized Dynamic Time Warping", WSEAS TRANSACTIONS on MATHEMATICS, Issue 8, Volume 11, August 2012, web: http://www.wseas.org/multimedia/journals/mathematics/2012/55-273.pdf, the entirety of which is incorporated by reference).

Cloud Side Rules Engine

The cloud side rules engine is designed to: 1. to improve the pipelines used in specific applications for specific users; 2. to do cross populational data mining to improve general application performance and user experience across the entire user base and for new users; and 3. to do cross populational data mining for potential new application or to serve a research study (internal or third party, while maintaining user privacy).

The cloud side rules engine may comprise: high level code that supervises the operation of the data mining methods that are run on the user data; a database of rules that determine which Workflow to apply based on the conditions (e.g. where a rule has the following structure: IF condition=true then execute Workflow ID); and an API that allows human researchers to guide the data mining process. The cloud side rules engine communicates with the profile manager to update rules and pipeline configurations in client device applications.

Workflows in the cloud can apply machine learning methods that can learn new pipelines, change which pipelines to apply to specific contexts, learn new patterns, learn new patterns that can help a User achieve their goals. Rules that control machine learning choose workflows that apply different Machine Learning methods depending on the conditions faced by the user. A different machine learning workflow can be defined that chooses different classes to learn to classify and the specific feature extraction and feature selection methods to apply. When a machine learning workflow has discovered a new predictive model or classification pipeline, the rules engine can direct the updating of new pipelines the apps that can use the pipeline and the contexts that these pipeline contexts can apply.

Workflows that include machine learning and other statistical methods that determine if specific rules are effective and need to be updated as well as the updating process (example of process are, discrete changes—that may include user notifications, continuous adaptations like response speed, or A/B testing changes whereby variations to rules are tested with a user to see if the behaviour is desired. Variation technique may involve stochastic processes like genetic algorithms, or use statistical methods such as hidden markov models with baum-welch training.

The Following is an example of how the Cloud Based Rules Engine updates a pipeline based on a significant event "Creative Breakthrough" achieved by the user. For the condition "Activity Type=Working Alone on a Project", the corresponding workflow may be "4. Use unsupervised learning to find statistically significant patterns associated with time stamps of this User. Wait until end of this Activity Type or Creative Breakthrough to process". For the condition "Activity Type=Creative breakthrough", the corresponding workflow may be "5. Use supervised learning". For the condition "Activity Type=Statistically Significant Patterns Discovered", the corresponding workflow may be "6. Alert User that new patterns are available for review". For the condition "Activity Type=Better Prediction Model Discovered for Mental State=Creative", the corresponding workflow may be "7. Update all APPS using pipeline ID with new parameters of the Better Prediction Model, and transmit new parameters associated with pipeline ID User's Local Profile".

In this example, first, the Cloud User Profile may receive an updated User Profile from Mobile APP. The Rules Engine in the Cloud sees that Activity Type="Working Alone on A Project" and waits until end of this activity to start looking for patterns. Second, The Rules Engine in the Cloud sees that Activity Type="Creative Breakthrough" and searches all data associated with Activity Type of that User just prior to the Creative Breakthrough and use patterns learned from previous unsupervised and supervised sessions across all APPs as input to Supervised Learning. Supervised Learning done in the Cloud discovers a Prediction Model that has higher accuracy than the previous prediction model. The Rules Engine sets Field "Machine Learning Activity Type="Better Prediction Model Discovered". The Rules Engine starts a Workflow that updates the pipeline ID with the parameters learned. The Workflow updates the User's Profile with the new parameters in the Pipeline ID. Third, the Cloud transmits the new parameters of the Pipeline ID to all Mobile device APPs using that Pipeline. In the future, app IDs that are associated with this Pipeline ID will use the new parameters.

When the rules engine yields improved pipelines, these pipelines are made available to the client devices through providing the pipeline ID along with the associated parameters that the pipeline requires. All pipelines are available on the device and can be switched between pipeline ID by instruction by message from the Cloud with associated pipeline parameters. The Cloud Server analyzes each Activity Type and determines which pipeline to choose for this user or activity. The pipeline chosen may also depend on other information gathered from user's profile such as age and or as a direct response to survey questions or if a user suffers from a particular disorder. Other information that is used to fine-tune the pipeline is a history of the sessions of the user: number of sessions, total number of session hours, time of day of session, session scores and results. Machine learning is used to determine patterns across a user's sessions to change and adapt a user's pipeline. The Cloud Server transmits the pipeline ID to the device along with the learned parameters. In addition, the specific parameters of the pipeline can be determined within the device if disconnected from the Cloud. If this is a first time user of the an APP then a default pipeline is chosen for the user. Again, default pipelines may be fine-tuned based on demographic or survey responses. The user can be part of an evaluation to select among a number of different pipelines.

Feature Extractor Designer

The feature extractor designer is comprised of a set of pre-processing algorithms that are used to filter, normalize, or otherwise transform the raw time-series data into a related time-series that is more suitable for different types of feature extraction. The cloud based rules engine defines the learning problem and informs the Feature Extractor Designer of the prior knowledge of what combinations of Pre-Processing and Feature Extractors are to be considered. The populations of combinations are computed in parallel. Tunable parameters and alternative Pre-processing and Feature Extractor combinations are selected using uniform or stochastic sampling within a range, genetic algorithm or a gradient method depending on the particular pair of algorithms.

The server's pipeline improver houses an array of pre-processing methods which are available to the client device. blind source separation methods are considered pre-processing as the end up producing filters that can be applied to the multivariate time-series data, however they tend to be used slightly differently than on the client device due to the availability of data.

The Rules engine defines the learning problem and informs the Feature Extractor Designer of the prior knowledge of what Pre-Processing should be considered.

The server's pipeline improver houses an array of Feature Estimation methods which are a superset of the methods available for the client device.

More advanced feature methods are included that may be too complex for client device computation. These highly advanced methods can yield highly discriminative features that can yield much better machine learning performance through the creation of over complete features that can yield better separability, and reduced search spaces through filtering or built in invariances (such as translation invariance). Resulting discovered patterns can then be discovered in the data using simpler methods once we know what we are looking for. Two methods that are utilized include (not exhaustive): Emprical Mode Decomposition (EMD) or Ensemble EMD (EEMD) (see: Zhaohua Wu and Norden E. Huang "Ensemble Empirical Mode Decomposition: A Noise-Assisted Data Analysis Method", Advances in Adaptive Data Analysis, Vol. 1, No. 1 (2009) 1-41, web: http://perso.ens-lyon.fr/pierre.borgnat/MASTER2/EEMD.pdf, the entirety of which is incorporated by reference); and Scattering Wavelet transform (see Stephane Mallat, "Group Invariant Scattering", 15 Apr. 2012, web: http://arxiv.org/pdf/1101.2286.pdf, the entirety of which is incorporated by reference).

Unsupervised Machine Learning for Patterns of a Single User

The server may constantly be calculating correlations between different users or between different data for a particular user. A rules engine will determine what the server should work on so that the server's time is efficiently managed.

Automated searching for meaningful patterns or associations in data usually requires a human to create a statistical analysis plan with hypothesis and execute the analysis off-line in statistical software program. In accordance with an aspect of the present invention, this method automatically searches the data in the cloud platform or on a user's device for meaningful patterns without any prior hypotheses in mind. Biological and non-biological data can be searched to find meaningful patterns about a specific individuals or across population of individuals.

A meaningful pattern is a pattern identified in a user's bio-signal data that represents a user's response observed to particular events (which may be called "feature events"), particularly when that user's response is observed multiple times with respect to the repeated occurrence of those particular events. Searching for meaningful patterns may be used to predict whether a feature event belongs to one category or another. For example, a meaningful pattern may occur when the value of each feature event (A, B, C) occurs together more often than just random chance. The patterns may also reveal new insights into behaviour. "e.g. I am always anxious on Sunday evenings", or they may suggest whole new categories and cluster them together. A meaningful pattern can be used to (i) build prediction model (ii) to select features. Once a meaningful pattern has been discovered, the system platform may modify or create a pipeline to predict one of the feature event values from the other two. So if the system platform is provided with the values of A and B the system platform may be able to use the pipeline to determine the probability of the value of C. A meaningful pattern may be determined across individual users or across multiple or all users. Any time a meaningful pattern is determined for any user, any such pipeline developed may be available to other users or applied to bio-signal data of other users.

Feature event data (including identifications of feature events, and respective values) may be inputted manually by a respective user, or they may be sourced from elsewhere, such as from a calendar application or emails accessible from the client computing device pertaining to the user. For analysis purposes by the system platform, it may be significant that the feature events occur together usually in a point in time or occur together at a place. Therefore, the feature event data may be time-coded, optionally by the system platform, in order to reference against bio-signal and/or non-bio-signal data of the user with the same or similar time codes. A feature event is all of the variables that go into getting a single data point of multiple variables. Features can be derived from any measure or variable that is available to the system platform, such as time of day, EEG signal, heart rate, person's mood, age, gender, height, weight education, income, etc. The system platform may maintain a database store of all of the combination of feature events. When the system platform performs a prediction the system platform finds matching patterns and uses the highest order feature events first to do the classification.

The system platform typically may look for at least 10 data points for every feature and for every category. For example, if the system platform has three categories (e.g. drowsy, alert, agitated) and ten measurements per data point then the system platform may require at least 3*10*10 data points (i.e. 300 rows and 11 (10 measurements+Category) columns). The rules engine can enforce this kind of policy so that system platform only begins looking for a new pattern in feature event data when there is a particular amount of data to analyze above a particular data amount threshold.

Figure 10:
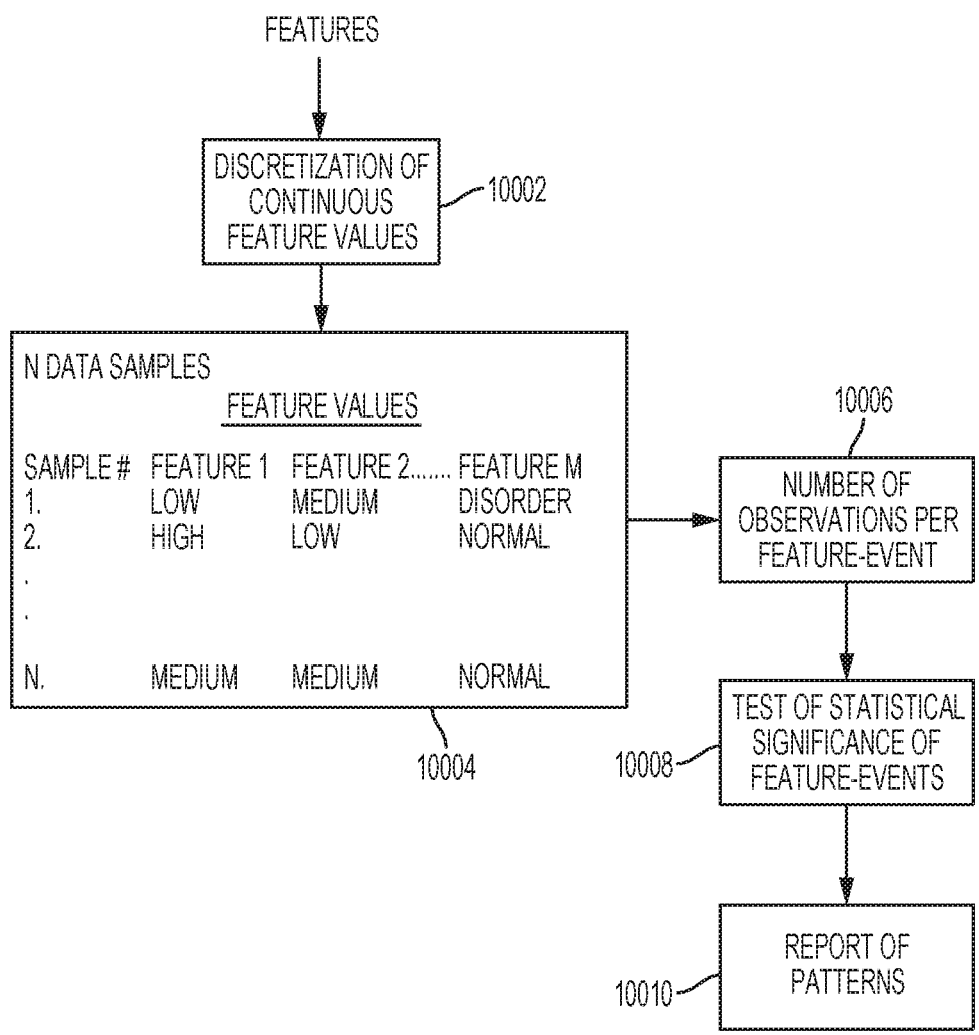
FIG. 10 illustrates an embodiment of a method for discovering meaningful patterns in brainwave data in accordance with the present invention.

A method for searching for meaningful patterns is shown in FIG. 10. A data set with features 10004 will be searched for patterns that may provide insights that are meaningful for individuals, or across populations or common for specific demographics or for people with the same disorder. These patterns may also be used as rules for classification. The Cloud platform has acquired data from a number of different applications that the user has used. Example, one application uses EEG recording of a single session. A session may consist of a number of parts or epochs. A session or epoch is described by a number of features. Features are calculated from biological and non-biological data. Feature values can be continuous variables 10002 (e.g. EEG alpha power), ordered (e.g. small, medium, big) or categorical (e.g. ADHD, Normal). Values of continuous variables 10002 are quantized (i.e. binned) into a set of discrete bins. There are situations where it would be valuable to consider other observations 10006 like nominal features such as gender or hair colour along with numerical values to build Predictive Models. Quantization allows nominal and continuous variables to be considered simultaneously. Each feature can take on a discrete value from an integer number of total values for that feature. A primary feature event occurs when a single feature takes on a discrete value. A kth order feature-event contains k primary feature-events. An example of a 4th order feature-event would be from a session where the person is 1) moderately relaxed 2) heart rate variability is low, 3) alpha power is high and 4) alpha variability is medium. The next step is to determine if the feature-event is a statistically significant pattern 10008. There are a number of statistical tests available to determine statistical significance such as Chi-square or adjusted residual. Tests of significance 10008 are two-tailed in that a significant pattern may occur if there are more than a random number of epochs or sessions with the same feature-event or less than a random number of epochs. Significant patterns can be used to predict a category. For instance a session that had low heart rate variability, high alpha power and medium alpha variability can predict that a person was moderately relaxed. The strength of a pattern is determined by the probability of its occurrence. These reports of patterns 10010 can be used for classification or prediction. Individuals can be alerted to the existence of significant patterns that may be informative for an individual to understand their patterns and help them reach their goals.

The system platform may determine which bin a time-coded portion of an EEG signal may be associated with by evaluating the value of median voltage of the EEG signal.

When the system platform is provided with an EEG signal that can be used for training or to learn a model, the system platform could process the signal to remove unwanted artifacts. The system platform may then take slices in time across the entire EEG signal (e.g. at every 10 ms). The system platform may calculate the median voltage within every slice across the entire EEG signal. The system platform may sort these values from low to high. For example, where there are 10,000 slices, the system platform may use 10 bins, looking at the ordered 10,000 values and dividing them into 10 parts. Then the boundary of the first bin may be determined by a voltage value of 1000 or less, while the second bin boundary may be determined by a voltage value in the range of 1001-2000, etc.

In a non-limiting exemplary implementation, discovering meaningful patterns may be performed as follows. Assume a user "Charlie" having two friends "Andrew" and "Bob". Charlie has a database of outings of himself and his friends including information regarding whether Andrew and Bob go out without Charlie, which has been reported to Charlie. The database has information about the outings such as venue, date, type of activity, whether the outing was enjoyable etc. Charlie wants to analyze the data to find patterns. To simplify the example, focus on two features: 1) whether or not a friend was present and 2) whether or not Charlie enjoyed the outing. There are six primary feature-events in this example: A=Present (Pr), or A=Absent (Ab); or B=Pr, or B=Ab; or C=Enjoyed(E), or C=Not enjoyed(N). An example of a second order feature-event in this example may be A=Pr, B=Ab. An example of a third order feature-event in this example may be A=Pr, B=Ab, C=E.

The table shown in FIG. 11A shows all permutations of second order feature-events 11000A of Andrew, Bob and Charlie that occurred over a total of 102 outings. The column ox is the observed number of these second order feature-events across all 102 outings. The column ex is the expected number based on assuming that the features are statistically independent. The column dx is adjusted residual a statistical test that determines if the observed number is statistically significant difference from the expected number. None of the second order candidate feature-events 11000A are statistically significant and therefore not considered patterns.

The table shown in FIG. 11B shows that four significant 3rd order feature events 11000B are statistically significant patterns. The first pattern reveals that if both Andrew and Bob are absent then Charlie does not enjoy the outing. The second pattern reveals that if both Andrew and Bob are present at an outing then Charlie does not enjoy the outing. The third pattern shows that if Andrew is present and Bob is not then Charlie enjoys the outing. The fourth pattern shows that if Andrew is absent and Bob is present then Charlie enjoys the outing. Therefore if one but not both of Andrew and Bob are present then Charlie enjoys the outing. This pattern helps Charlie plan future outings.

In this example, the expected numbers may be determined by assuming that there is no relationship between the features. So in the example, the system platform would determine the expected value by multiplying the probability of each event occurring on its own together and then multiply by the total of data point. Example P(A=Ab)*P(B=Ab)*P(C=No)*Total # Datapoints=13.

The above example shows the power of considering features simultaneously for discovering patterns. A search across two features revealed no patterns, however, searching across three features simultaneously revealed significant patterns.

Unsupervised Machine Learning for Patterns Across Multiple Users

After EEG raw data is transmitted to the Cloud, as described previously under the heading Mobile Device Based Application—Processing at Cloud Server, EEG data from a large number of users may be accumulated in the Cloud Server. EEG feature values plus other information stored in each User Profile is discretized. These discretized features are sent to the Machine Learning module for automated pattern searching. This may be an offboard server that may have dedicated specialized hardware to process this process intensive search.

All permutations of patterns up to a certain number of simultaneous features are searched for statistically significant patterns (i.e. go as high as fourth order feature-events).

A database of significant patterns (or user-response classifications) is accumulated in a pattern database in the Machine Learning module of the system platform. These patterns are shared with users that exhibit these patterns. A particular user may be asked if the shared pattern is of interest to that user. If the user responds yes, the Machine Learning module sends feature detection thresholds and prediction model to the user's mobile device. The mobile device processes EEG signal and provides predictions to the user. The user may respond to the predictions as to their accuracy or lack thereof. The revised user feedback may be used to update how segments of EEG or biological signal data is labelled, thereby updating and improving the information stored.

The search for meaningful patterns continues, and a second level of machine learning can be applied to the discovered patterns guided by human knowledge of by a second level of supervised learning across the discovered patterns.

Feature Selection

Feature selection involves searching for features that can provide meaningful information towards the prediction at hand. Sets of features can be selected that together contribute to improving prediction accuracy when testing against data. Another way of selecting features is to systematically search for features that have a statistically significant relationship with a dependent variable or category.

Feature selection algorithms may include: Stepwise Logistic regression; Stepwise Linear Regression; minimum redundancy maximum relevance (mRMR); and genetic algorithms.

Feature selection is typically done using a wrapper method where different permutations of feature selections are used to train a classifier such a support vector machine with a non-linear kernel. One embodiment may use a genetic algorithm to permute the features, and the resulting classification accuracy of the trained classifier is used to judge the fitness of each selection (fitness then being used as part of the selection process for future generations, as may be typical for genetic algorithms). Parallel forms of a genetic algorithm may also be used to distribute the computational load across a cluster or grid implementation of the system platform.

Constraints relating to the real-time computational resources are introduced into the feature selection process to ensure that the resulting real-time estimators are runnable on the target platform. Parameters may be platform dependent. For example, an application running on an iphone3 may have a different constraints than and iphone4 which will have different characteristics than a desktop computer.

Supervised Machine Learning

Figure 5:
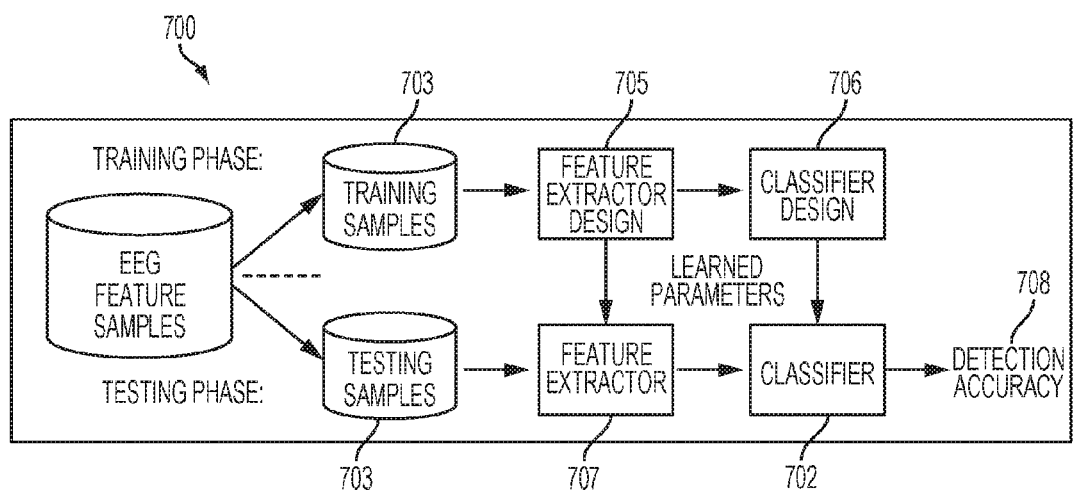
FIG. 5 illustrates an embodiment an analyzer using machine learning techniques in accordance with the present invention.

In the embodiment as shown in FIG. 5, the feature extractor and the classifier can be implemented in a supervised machine learning environment 700.

For example, training data 703 can be sent to the feature extractor 701 and classifier 702 for analysis, and the results of the analysis can be output to a supervisor for review (for example using a suitable graphical user interface such as a dashboard). In this example, a supervisor may be a feedback mechanism whereby a person can decide whether the analysis has correctly identified a feature associated with a particular pattern. In another aspect, the computer system may include a rules engine that includes a series of rules for guiding a supervisor in deciding whether the analysis has correctly identified a feature associated with a particular pattern, depending on a defined context, and optionally also depending on parameters associated with the bio-signal data and the non-bio-signal data. The rules engine may be linked to a suggestion engine that supports the display of one or more messages to the user to guide the profile development process, and/or system calibration processes.

The rules engine may allow the feature processor to know which dimensions to prioritize, and may reduce the amount of signal bandwidth that is necessary for transmitting. The feature space or dimensions may be dependent on the context. The rules engine may be considered to be a context based switcher, and as such may use the outputs of different estimators (i.e. is the user sitting in front of their computer; is the user working; what is the user hearing, etc.).

The context estimator can be considered to be part of the rules engine. It may run in closed loop fashion so that context is estimated with feedback. The context estimator may yield more accurate estimates that are created using better information or the results of certain algorithms that take time or additional information to run will need to be applied back in time. A timestamp may be used to mark the event of the new context estimate. Estimated quantities in the time series database (such as context or user's mental state) are included as rows while pipeline ID and configuration parameters are included in the columns. Estimated quantities can thus be traced back to their origin, and thus provides a means of determining if they could be updated because of a change in their data sources or algorithms. This could create feedback loops, and care must be taken to ensure stable operation. Stability of the estimation is monitored by and algorithm that operates on past classifications of the data which are accessed using the timestamp column of the data hypertable. A new row may be created with each modification to the context estimate marked with a timestamp corresponding the time that the new estimate was created. The context estimator may assess the importance of source data and also to estimate a confidence interval (i.e. value, uncertainty, and sensitivity to other inputs). The stability of recursive context estimation is sensitive because of how its effects propagate. To compliment recursive (sequential) estimation, concurrent (parallel) estimation using random sampling from prior distributions of context states may be used in order to yield stable and accurate estimates.

In another aspect of the present invention, the rules engine itself is linked to the machine learning systems and methods that are made part of the system of the present invention, so that the processes implemented by the rules engine (for example for enabling users to develop their profiles and enable calibration of the system based on training data 703) may be modified iteratively based on learning developed by the system by engaging with a plurality of users and optionally a plurality of groups of users that share attributes in the manner in which they interact with the system and/or particular applications linked to the system.

For example, a user of the client device may be asked whether a particular classification corresponds with a particular emotion or physical movement experienced at the time the bio-signal data and non-bio-signal data was collected. This may be useful where there is more than one pattern or correlation for a physical or emotional state. A skilled person would understand that other ways to supervise machine learning may be employed.

The results of the extraction and classification, after feedback from the supervisor, may then be used to improve the feature extractor 705 and classifier algorithms 706. These tests may be repeated in order to train the machine learning system such that, for example, by using one or more known statistical models for analyzing bio-signal and non-bio-signal data with greater accuracy 708 may be achieved. For example, a mixture of Gaussian distribution models may be used.

The bio-signal and non-bio-signal data, before or after processing and analysis, may then be associated with a particular user of the system, for example using a profile builder associated with the system. A profile builder may be linked to a database and may embody one or more processes for defining for each user a set of user profile data 114. This user profile data 114 may also include, for example, data from different biofeedback applications, data from different sensors, data from different client devices, and user demographic data. Bio-signal and non-bio-signal data may be different for different users. Thus, optionally, algorithms 116 used in the pre-processing, feature extraction, and classification of data may also be adjusted for each user, e.g. based on preferences or characteristics of the user.

Different profiles may exist for an individual user for example for different applications that link to the system of the present invention. User profiles may define different attributes in a number of different ways, and these attributes may be reflected in profiles in a number of different ways. For example, users of a particular application linked to the system (such as a meditation training application) may be classified based on a range of values associated with their experience of certain meditation induced states. A representative profile may therefore include an identifier that is associated with a state classification profile that best matches the individual user. This system may detect that over time the user's interactions with the application are changing (for example because the user's medication training efforts have been effective). This may be detected by the system, and the system may dynamically adjust the user's profile. Also, the machine learning system may detect and generate insights regarding improving the classification of individuals based on new understanding of interaction of users associated with particular attributes with selected functions of an application, and the creation and use of profiles by the system may be automatically adjusted based on these insights.

For example, in one implementation of the invention, an analytics engine may be used to analyze changes in user features or attributes, and automatically integrate such changes by updating the user's profile, so as to provide automated calibration of the operation of the system in interacting with users, on a user by user basis.

The present system may also utilize segmentation techniques to group users into user segments based on shared attributes, and reflect such user segments in management of user profiles.

There are many unknown associations of EEG signals that can be learned about humans. The system platform, and the cloud in particular may be configured to continuously, periodically, or in any other scheduled manner look for meaningful patterns or to update classification models. Two of the major challenges for classifying EEG signals is the difficulty in obtaining accurate labelled segments of EEG signals and the other challenge is to select features of the EEG signals that can provide meaningful information for the classification task at hand. This system platform uses non-EEG data to help label EEG data acquired from users undergoing a specific activity or exercise. Non-biological and other biological features across a number of users may be analyzed using pattern discovery, cluster analysis, or factor analysis along with dimension reduction methods such as Principle Components analysis to plot these features in reduced dimensions. Rules, thresholds or boundaries of these plotted reduced dimensionality of features are set and a label or score is established for each person or each session of interest that is related to a goal that the user is trying to achieve. This score can be thought of as the dependent variable (i.e. y-value in linear regression) that can be used for supervised learning of the EEG data. Features are extracted from the EEG signals with sessions labelled as per the score or region derived from other biological and non-biological data. The reduced dimension space allows searching for optimal classification accuracy easier by adjusting thresholds, relabeling sessions and re-calculating classification accuracy. The reduced dimension space also allows for more efficient searching to find better performing classification models. A superior classification model either has higher accuracy or requires lower number of features (which may mean more efficient processing) compared to other models. A number of iterations of a supervised learning method is used to build a new model for classifying EEG signals into categories or predicting scores meaningful for a particular goal. A model fit parameter is calculated and checked against previous iterations of model fit or against a model fit threshold. If the model has not converged then new thresholds or boundaries are chosen to establish scores of the non-EEG data, then a new model is learned using the new thresholds. If the model has converged either because model fit parameters have plateaued or exceeded a threshold then the model building iterations stop. A decision is made to keep the new model or abandon the new model because it has not exceeded the performance of the existing model.

Figure 9:
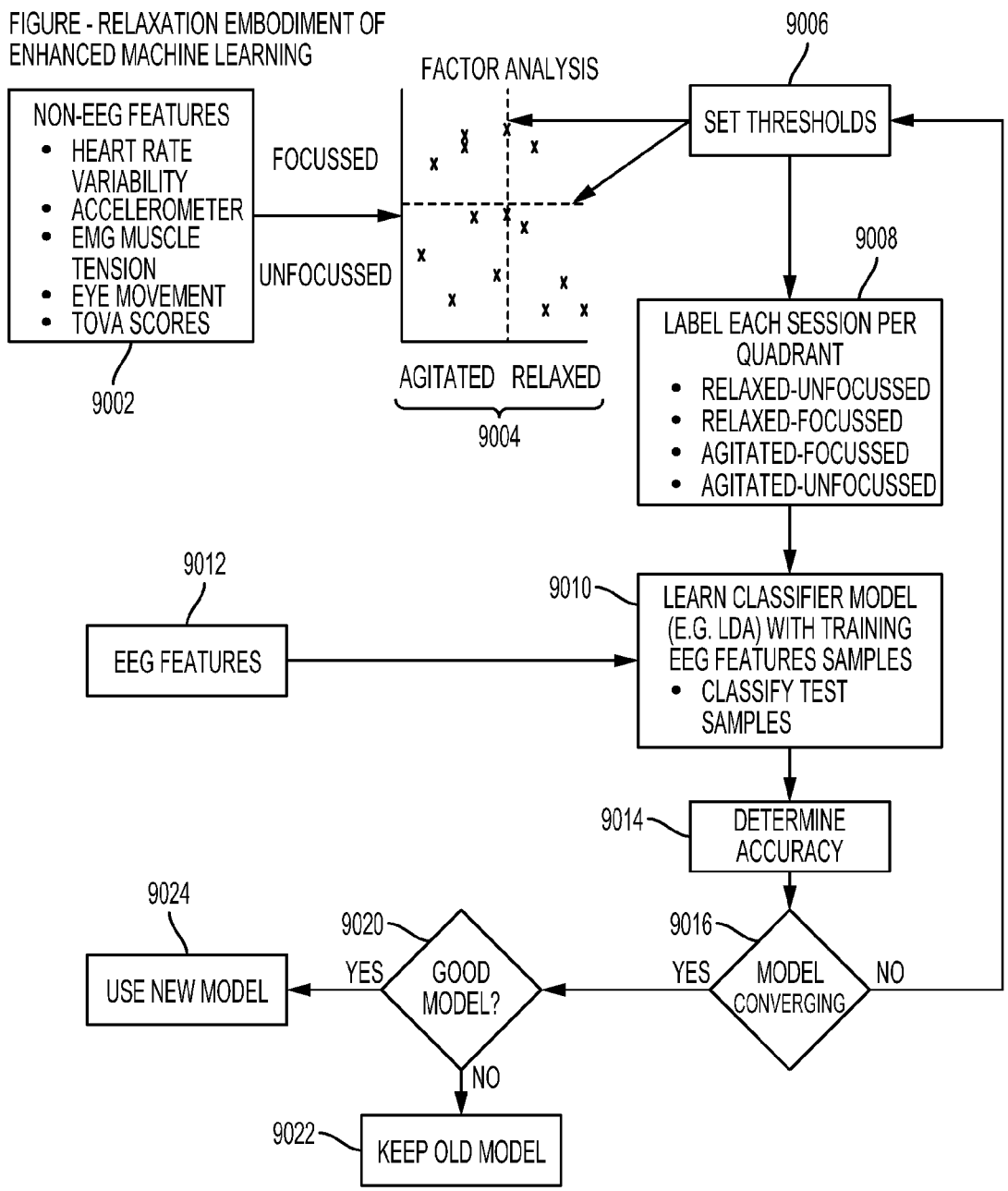
FIG. 9 illustrates an embodiment of a relaxation embodiment of enhanced machine learning in accordance with the present invention.

FIG. 9, shows a relaxation embodiment of enhanced machine learning showing how enhanced machine learning can be applied to the goal of helping a user reach a deep state of relaxation while remaining alert. The user may want to learn to achieve a deep state of relaxation while remaining awake and focused to help the user improve the user's performance for a number of activities that can benefit from a simultaneous state of relaxation and focus like golf or archery. Non-EEG biological data 9002 and non-biological data is gathered across a number of users trying to achieve a state of deep relaxation and focus while their EEG signals are being recorded. Biological features such as Heart Rate Variability, accelerometer readings of motion, level of muscle tension recorded by analyzing EMG signals of facial or body muscles as well as eye movement are recorded with timestamps that are synchronized to the EEG recording while users engage in relaxation/focus exercises. Measures of focus are obtained from the user such as subjective ratings of alertness from the user or from tests like Tests of Variables of Attention (TOVA). Factor analysis 9004 is used to reduce the dimensionality of the non-EEG features 9002 into two dimensional space as shown in FIG. 9. A higher number of dimensions is possible but requires an additional threshold per dimension. One dimension is associated with features that describe level of relaxation and the other dimension is associated with features of focus. A threshold is selected along each dimension and the two dimensional space is divided into four quadrants 9008: relaxed-focused, relaxed-unfocused, agitated-focused, and agitated-unfocused. Features extracted from segments of EEG data 9012 are labelled with one of these quadrant labels that occurred during the same time segment as the non-EEG data. A learning algorithm 9010 such as Linear Discriminant Analysis (LDA) is applied to the EEG feature data that is separated into training and test data. The accuracy of classifying the test samples is determined 9014. Another set of thresholds is set. Feature data is labelled into one of the quadrants 9008. An LDA model 9010 is learned and the model's accuracy to classify the test feature data is determined 9014. When the accuracy of the models converge 9016 and no additional improvement occurs, then the searching stops 9022. If the model has improved 9020 accuracy over older models then the new model may be used 9024 for training of relaxation and focus. This method can be adapted by using different EEG features 9012 for analysis. The resulting classification model can then rely solely on EEG signals without extracting the additional biological or non-biological data.

Another embodiment of the Enhanced Machine Learning method is to help find a state of flow for a user undergoing a training application by adjusting the level of challenge presented to the user. The user is asked to answer questions about the training activity such as the user's perceived level of skill, and how challenging was the training activity and emotion experienced during training (e.g. boredom, anxiety, state of flow etc.). Any grades related to training assignments or test scores are also included as features. These features are input to a dimension reduction algorithm and then two thresholds are selected 9006 where one dimension may be interpreted as the level of the user's skill while the other dimension is considered the level of challenge placed on the user. These are used to label the EEG data recorded during the training sessions as one of four possible labels: low-skill/low-challenge, low-skill/high-challenge, high-skill/low-challenge, and high-skill/high-challenge. Patterns of EEG features 9012 are discovered associated with each quadrant 9008. These learned patterns or rules can be used for future training sessions to automatically adjust the challenge level of the training depending on the EEG patterns exhibited by the user and help foster a state of flow that the user enjoys while learning.

The user's data can be processed and analyzed on the client device, or the data can be uploaded to a cloud database for processing and analysis.

There are classes of biological signals that do not require a high bandwidth of information to be transmitted since the biological signal processing is mature. For example, Heart Rate Variability is an important physiological measure that is related to emotional arousal, anxiety, time pressure strain and focussed attention. Heart Rate Variability only requires interbeat intervals to be analyzed which requires only bytes of data every second. In addition to EEG signals, muscle tension can be derived from EMG signals measured by forehead EEG electrodes. Analyzing and processing these signals in a mobile device or even desktop PC would tax the resources of the device. The following message flow describes how Machine Learning is spread across the device and the Cloud to take advantage of the larger processing capacity of servers in the Cloud offloading this kind of processing from the mobile device.

Message Flow for Supervised Machine Learning for Single Person Machine Learning

The present invention may allow collection of time synchronized biological data from a number of sensors within or attached to the device and apply machine learning to the multiple sources of data in the cloud. In addition, predictions learned in the Cloud can be sent back to the device so the user can enhance the Machine Learning algorithm, which may provide for the user to learn about himself or herself and enhance learning of prediction models. This message flow describes an application that uses Heart Rate Variability and facial muscle activity to determine the level of a person's emotional arousal continuously and use this information to label sections of EEG data. Machine Learning is applied to the EEG signal to create a model for predicting emotional arousal based on EEG signals alone.

After EEG raw data is transmitted to the Cloud, as described previously under the heading Mobile Device Based Application—Processing at Cloud Server, the user may set the User Profile to "Learn emotions from EEG". A photoplethysmography sensor is connected to the mobile device. Interbeat intervals or time stamps of R signals detected from the heart are transmitted to the cloud server User's Profile.

The Cloud server selects a pipeline appropriate to the task of learning emotions. Filters and artifact detection methods are set to separate out EMG data from EEG data. Features are extracted from the interbeat interval such as frequency information (power spectral density information) determined from the heart rate interbeat intervals. Features are also extracted from EMG such as spatial information, firing rate and signal intensity. Factor analysis is used to reduce the dimensionality of these features into a lower dimensional space. Data is collected for several seconds to a few minutes. The machine learning rules engine sets thresholds on the reduced dimension space. Based on these thresholds, an estimate of the person's emotional state is determined.

This emotional estimate is sent to the device, which may prompt the user to answer a question such as: "Based on muscle tension and heart rate, the cloud server estimates that you are under moderate stress. What is your emotional state?" The user may respond "Low, Medium or High Stress". The user's response is sent to the Cloud Machine Learning module.

The Machine Learning module of the system platform adjusts the thresholds based on the user's information. The user's heart rate and EMG features are used to determine if the user is under low, medium or high stress. This is used to label segments of EEG data. The machine learning module then uses these labels to extract features from the EEG signal and learn a model that can predict emotions directly from the EEG signal without processing additional data.

The steps of the machine learning module determining the emotional state, prompting the user to confirm, and adjusting the machine learning module thresholds may be repeated to refine the learned prediction model that includes the user in the loop to evaluate models learned by the Cloud Machine Learning.

The EEG based emotion prediction model (pipeline) is sent to the device.

Since the prediction model has less processing demands compared to learning, the device can start providing emotion predictions to the user.

Example Pipeline: Common Spatial Pattern (CSP) Pipeline

This is an example of using a pipeline to categorize whether a person has a busy mind or quiet mind, called a common spatial pattern ("CSP") pipeline. The CSP pipeline may have value as mindfulness based practice (i.e. quiet mind) and has peer reviewed evidence that supports health and psychological benefits to users that practice mindfulness.

This example shows a pipeline customized to a particular user. The same steps below can also be done across users for training pipeline parameters.

A User is asked to calibrate (i.e. train) the pipeline that will provide feedback when the user has a busy mind compared to quiet mind. A user wears an EEG headband that records 4 channels (left and right forehead, left and right mastoids) at 500 samples per second. The user undergoes two calibration sessions: (a) a 4 minute recording that asks the user to do mental math (e.g. count backwards by 7 from 383) to induce a busy mind; and (b) a 4 minute recording that uses progressive relaxation to have a quiet mind. Session (a) provides training (i.e. calibration) data for Category 1="Busy Mind". Session (b) provides training (i.e. calibration) for Category 2="Quiet Mind". The Mobile device sends the EEG data of both sessions to the cloud to learn a model.

The User is given instructions for the next part of the exercise while the Cloud learns the parameters of a pipeline with the following steps. The Cloud chooses the default parameters by information stored in the Cloud for busy mind and quiet mind algorithms. The Cloud separates the sessions into 3 minutes for training and 1 minute per testing the Prediction Model.

An infinite impulse response bandpass filter is applied. For example, a Butterworth Filter starts with the default settings of 1–2 Hz for the lower stopband, 2 to 28 Hz being the passband, and 28 to 32 Hz for the upper stopband. At the stopband frequencies of 1 and 32 Hz the signal is attenuated by −50 dB. The ripple of 0.5 dB above the average passband gain occurs at 2 and 28 Hz. The EEG signals are divided into epochs of 5 seconds long for the Busy Mind and Quiet Mind sessions. There are 36 epochs (3 min*60 sec/5 sec) per training session. Each training epoch has 2500 voltage samples (500 samples/sec*5 sec).

A matrix is built for Busy Mind "BM" that is 4 rows by 90,000 voltage samples. Each row is the voltage per EEG signal. Another matrix "QM" is built for Quiet Mind of the same size 4×90,000.

The covariance matrix is calculated for each category by COVBM=E[(BM−E[BM])*transpose((BM−E[BM]))] and COVQM=E[(QM−E[QM])*transpose((QM−E[QM]))].

An eigendecomposition is done to get the eigenvalue (D) and eigenvectors (V) by solving the following formulae: COVBM*V=D*(COVBM+COVQM)*V. V is a 4 by 4 matrix of transformation vectors. D is a diagonal matrix with 4 eigenvalues in the diagonal.

The features for each epoch t are calculated by taking the variance of signal per EEG electrode and multiply by V and take the log. So features(epoch time t)=log(var(EEGsignals(t))*V). This may provide four values per epoch time t per Category. FeatsBM stores the 4 features per epoch of Busy Mind and FeatsQM stores the 4 features of Quiet Mind. Another way to think of these features is that one epoch is a point plotted in four dimensional space where each axis is one feature.

In this case the system platform performs feature selection using Linear Discriminant Analysis ("LDA"). LDA weighs the contribution of each feature value that will maximize the distance of point in the BusyMind Category to Quiet Mind. LDA will plot points of each category along a one dimensional line (for two classes) that will be Gaussian since the voltage values of EEG are generally Gaussian calculated by weights=inv(FeatsBM+FeatsQM)*(mean(FeatsBM)−mean(FeatsQM)). Then the weighted or selected features will be calculated by yBM=transpose(weights)*FeatsBM and yQM=transpose(weights)*FeatsQM.

The 1 minute portion of the session that was withheld for testing is now divided into 5 second epochs and the parameters (IIR filter, V, LDA) determined above are applied to the BusyMind and QuietMind epochs. The signal of each EEG channel is IIR filtered using the same parameters. The features are calculated using V discovered in the training data FeatstestBM=log(var(EEGBMtestsignals(t))*V) and FeatstestQM=log(var(EEGQMtestsignals(t))*V). Then the weights discovered by LDA are applied to the test data by ytestBM=transpose(weights)*FeatstestBM and ytestQM=transpose(weights)*FeatstestQM. The distance of each feature in the test data is compared to the mean (FeatsBM) and mean (FeatsQM). The epoch is classified into the category where the selected features of that epoch are closest. The prediction model takes significantly less computing resources than training the prediction model.

The performance of this pipeline is determined by looking at the error rate of predictions of each epoch in the Test data into either Busy Mind or Quiet mind. We know the true Category since the User was asked to do an exercise that evoked a Busy Mind and then a Quiet Mind.

The parameters are varied and the above steps are repeated until the error rate converges. So the parameters that minimized error rate were discovered to be IIR filter bands 3 Hz, 6 Hz, 32 Hz and 36 Hz. Optimal Epoch length was 2 seconds. In addition to varying parameters, the Rules Engine may also specify variations in the steps taken. For instance, instead of an IIR filter use a Finite Impulse Response Filter, and or instead of CSP use Independent Components Analysis to extract features from the signal.

The user mobile device may be loaded with the new parameters for this pipeline. The user can enjoy new neurofeedback guided sessions i.e. feedback in real time as to the strength (i.e. distance of their calculated features to the training data they recorded during the calibration session).

Example: Quantization of Numerical Measurements Feature Extraction Method

There are situations where it would be valuable to consider other observations like nominal features such as gender or hair colour along with numerical values to build Predictive Models. The approach described below is to quantize the numerical values into discrete bins and then use Classifiers that operate on discrete values such as Naive Bayes, Decision Tree or Pattern Discovery.

The system platform receives an EEG signal that we can use to train or learn a model. The EEG signal is divided into epochs across the entire EEG signal at every 10 ms. Other time slices can be chosen. The system platform calculates the median voltage within every slice across the entire EEG signal. The system platform can also take the average or other statistics across the voltages in a time slice. The system platform sorts the median values from low to high. For example, assume a signal is provided that is 100 seconds long yielding 10,000 slices. The system platform may decide how many bins to use (such as #bins=5). The system platform may divide the ordered 10,000 values into 5 parts, divided into bins having boundaries every 2000 voltage value.

Figure 13:
FIG. 13 illustrates an example of bin boundaries used for quantization in accordance with the present invention.

The table of FIG. 13 shows an example of the bin boundaries 13000 used for quantization. These bin boundaries 13000 can be used to quantize other EEG signals. A EEG signal time slice with median value 5 will have bin value 3, and another time slice with a median voltage of −90.3 is in bin 1. Voltage values outside the lower boundary of bin 1 or upper boundary of bin 5 are tagged to have special treatment and may be ignored or treated as a gap in the signal that is filled by using interpolation.

Example: Pipeline Improver Using Naive Bayes Example

Naive Bayes has the advantage of being transparent in that other methods use complicated mathematical transformations that obscure what is happening to the signals and make it difficult to interpret what is happening. Naive Bayes can also be used with nominal variables combined with numerical variables. It can also calculate a probability for each prediction it makes so that we get a sense of the confidence it has in it predictions.

Assume training data comprises: twenty EEG signals of 3 minute recording for Category 1="Busy Mind" and a separate 3 minute recording of Category 2="Quiet Mind".

Assume test data comprises: twenty EEG signals of 1 minute recording for Category 1="Busy Mind" and a separate 1 minute recording of Category 2="Quiet Mind".

Therefore, pre-processing of training data may comprise: an infinite impulse response bandpass filter, such as Butterworth Filter, starts with the default settings of 1-2 Hz for the lower stopband, 2 to 28 Hz being the passband, and 28 to 32 Hz for the upper stopband. At the stopband frequencies of 1 and 32 Hz the signal is attenuated by −50 dB. The ripple of 0.5 dB above the average passband gain occurs at 2 and 28 Hz.

Feature Extraction of the Training Data may comprise the following steps. Each epoch is further divided into time slices of 20 ms in length. The median value of each time slice is calculated. Ten bins are chosen for quantization. The median values across both the Quiet Mind and Busy Mind training data are sorted in ascending order to find the ten bin boundaries as previously described.

Figure 14:
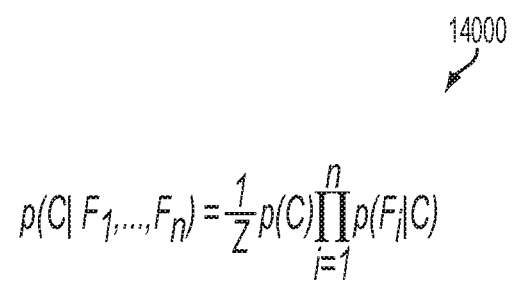

Feature Selection may comprise the following steps. An exhaustive search will be conducted across all permutations of the twenty features (i.e. each feature corresponds to the quantized voltage value of an EEG time slice per electrode). All permutations of single features, are considered, as are permutations of two features, then permutations of three features, and so on, until all twenty are considered. This is a very large search space that can benefit from parallel processing. Naive Bayes is the classifier that will be used. Naive Bayes calculates the probability that a set of features belongs to a category using the probability of each feature value occurring by counting the number of occurrences in the training data. The Naïve Bayes formula 14000 is shown in FIG. 14. In this example there are 9000 time slices in the Busy Mind and 9000 times slices in Quiet Mind training data per channel. The total number of occurrences in the training data are counted per bin per channel and then divided by the total number of time slices to determine the conditional probability of that feature bin given the session per EEG channel. The table of FIG. 15 shows an example count and corresponding conditional probability for 1 Channel 15000. A time slice that has feature bin=8 has a 0.077 probability of belonging to Busy Mind and 0.1 probability of belong to Quiet mind. The probabilities are calculated per channel in this way for the training data for all feature bins. An exhaustive search is conducted by the pipeline improver exhaustively searching across all feature permutations and keeping track of classification accuracy. The set of features with the highest classification accuracy are chosen to be used in the pipeline for this application. These new features are transmitted to the client device to update the user profile used by this application.

Parallel Methods for Cluster/Grid Computing for Pipeline Improver

The pipeline improvement Process is computationally intensive. The pipeline improver has been designed such that it can be largely parallelized so that it can make use of the computational scalability of cloud based cluster/grid computing architecture and databases such as Apache Hadoop that support MapReduce, or other parallelization schemes.

Parallel Preprocessing and Feature Extraction

Parallelization of these components involve creating a population of available pre-processors and a population of feature extractors as well as defining combinations of these components to be tested together. The rules engine defines the learning problem and informs the Feature Extractor Designer of the prior knowledge of what Pre-Processing and Feature extractors to select from and the ranges of tunable parameters for the selected methods.

Time contiguous data is extracted from a hypertable, and Preprocessing is mapped to be computed in parallel in a reduce operation. Preprocessed data segments can then be mapped across feature computation workers. The various feature types computer from the data is collated and redistributed to feature selection and classifier design (machine learning) processes.

Parallel Feature Selection and Supervised Machine Learning Classifier Training

Feature selection is typically done using a wrapper method where different permutations of feature selections are used to train a non-linear classifier (such as a support vector machine with a non-linear kernel). One embodiment uses a genetic algorithm to permute the features, and the resulting classification accuracy of the trained classifier is used to judge the fitness of each selection. Fitness is then being used as part of the selection process for future generations, as is typical for genetic algorithms. Parallel forms of a genetic algorithm are also used to distribute the computational load across a cluster or grid of the system platform. Constraints relating to the real-time computational resources are introduced into to the feature selection process to ensure that the resulting real-time estimators are runnable on the target platform. Parameters will be platform dependant (e.g. an application running on an iphone3 will have a different constraints than and iphone4 which will have different characteristics than a desktop computer).

Feature selection using a parallel genetic algorithm may be implemented on Apache Hadoop, or on other platforms, and may utilize user defined MAP, REDUCE, and PARTITIONER functions.

Genetic algorithms can be parallelize in different ways such as: (a) global single population master-slave GA; (b) single population fine-grained GA; and (c) multiple-deme GA ("island").

An exemplary non-limiting implementation off feature selection may comprise the following steps:

A: Initialize the population with random feature selection vectors.
  1. For mobile pipeline development, check that selected feature combinations are computationally feasible on the target device.
    1.1 For calculation speedup,
      use MapReduce to create the individuals; and
      utilize prior probabilities based on prior pipeline development.
B: MAP: For each feature selection vector.
  1. train a classifier (or set of classifiers to evaluate different types or parameter spaces) where training of different classifiers is done by a set of parallel worker functions, as they are independent (e.g. soft margin support vector machine (SVM) with Gaussian kernel);
  1.2 evaluate the fitness based on detection accuracy using cross validation;
  1.3 return (feature selection vector, fitness); and
  1.4 keep track of best (fittest) feature selection vector, returning best result when all individuals have been processed.
C: PARTITIONER: shuffle stage between map and reduce (randomly shuffle individuals across reducers).
D: REDUCE:
  collect small subgroups selection (e.g. Tournament selection):
    choose k (the tournament size) individuals from the population using random sequence from the Partitioner;
      choose the best individual from pool/tournament with probability p;
      choose the second best individual with probability p*(1-p); and
      choose the third best individual with probability p*((1-p)^2);
  collect a group of tournament winners and do crossover (E.g. with half uniform operator):
    select two sequential tournament winners, and evaluate each bit in the winners feature selection vector, and exchange with a probability of 0.5 (with 0.5 mixing ratio, the offspring has approximately half of the genes from first parent and the other half from second parent); and
    check to see if feature selection violates compute complexity limit for the client device.
  If complexity is okay, return the new feature selection vector into the new test population.
  If complexity is too large, redo crossover operation until a computationally feasible solutions is selected.
E: REPEAT STEPS: A→D UNTIL CONVERGENCE CRITERIA IS MET.

Figure 16:
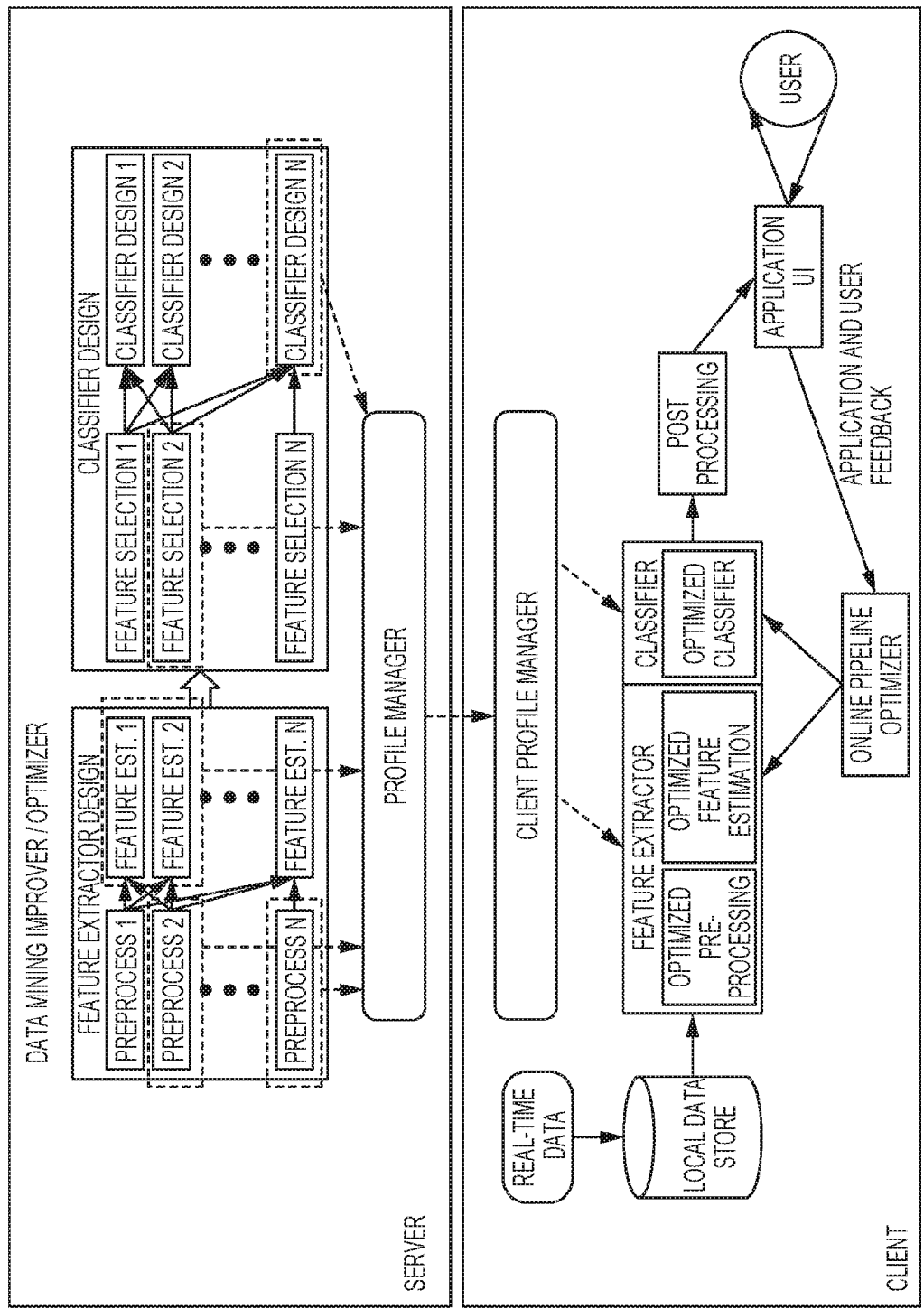
FIG. 16 illustrates how the client device may be updated in accordance with the present invention.

FIG. 16 shows how the client pipeline (e.g. 16002, 16004) may be updated.

Security/Privacy

In order to protect the user's privacy, a user may be required to grant access rights to certain data for certain applications. In an example embodiment, the client device 108 may allow a user to set privacy preferences 402 related to user profile data 114. These privacy preferences may then be used to control the data available to third party applications or the SAAS platform 302. In the case of availability to third party applications, the client device may have for example an access controller 404 configured to control user profile data 112 access based on privacy settings 402. A skilled person would understand that different techniques for controlling access to resources may likewise be employed. The privacy preferences 402 may provide for anonymization of the user profile data 114 when sharing the user profile data 114 with another user or system.

Personal data security may be provided through encryption. Sharing of un-curated data (giving people time-limited and fidelity limited access) though the sharing of encryption keys may be provided.

Privacy may be established between users that have a relationship; between users and researchers; and how this privacy is distributed in the devices and in the Cloud.

When sharing biosignal data with others, privacy measures are defined. Sharing will not share how these measures are derived from each person. For example, where there is a measurement of happiness/sadness, the score may be shared without absolute accuracy. Since sharing of how scores are computed is not done, there is less security risk of personal information.

The server which may be considered as trusted will be able to do more sophisticated correlational analysis of sensitive information, and will not require that the sensitive information is transferred to a untrusted party. The sophisticated methods of EEG and related analysis are sufficient to ensure that the system cannot be abused to retrieve sensitive information through the joint analysis of bogus data and sensitive user data that is under attack.

The timing features of the signal may be shared rather than the signal itself. This may be like doing phase correlation. The privacy measures provide that it cannot reconstructed but carries timing information. Methods of encryption can be used where the keys vary over time. The user's application may use user passkeys in an algorithm to produce pseudo random varying keys that will take time and date as inputs. This will allow the user to give a third party access only to a particular time range of data.

Encoding methods can also be used that cause separate encryption on multiple levels of fidelity. Partial keys may be given to access a particular level of fidelity for a time range, such that the user can finely control how much information is released.

Privacy methods may include: biosignal+other data captured (utilizing encryption and encoding to protect transmission between the sensor hardware and the platform); timestamping of data (relative to a global time); preprocessing (data may not be immediately transmitted to cloud); and obfuscating of user detail by enumerating locations but not providing a map (for faces; speaker identification; speech conservation; localizability geo location); and manipulating biosignal fidelity. Audio or video data may be transformed into intensity data or pre-filtering or compressed using a lossy method. Change detection may be employed. Features are transmitted back such that adequate data mining can be done, but full reconstruction of source data may be impossible. (e.g. does not constitute an audio recording, or video recording, and thus does not raise privacy concerns). The user could opt for full fidelity so that improved analysis can be done, like word association or speaker identification, to correlate with cognitive state changes. Change detection can be used for performing time-locked analysis of the data, such as ERP.

Other privacy methods may include: data is transmitted to the cloud database where personal data is encrypted; and data is accessed by another party only when allowed by the user's security rules.

A limited time range of access can give others limited access to data as determined by their relationship to the user but also to when the user is allowed access. For example, a user's personal trainer may be authorized by the user to receive full access to certain bio-signals when training, but not at other times. Time limitation can also help in privacy protection in the sharing of data that has had very little post processing. Time-limited and fidelity limited access may be enabled through the sharing of encryption keys. The encryption keys can vary over time. The user's application will use user passkeys in an algorithm to produce pseudo random varying keys that will take time and date as inputs. This will allow the user to give a third party access only to a particular time range of data. Encoding methods can also be used that cause separate encryption on multiple levels of fidelity. Partial keys may be given to access a particular level of fidelity for a time range such that the user can finely control how much information is released.

With regards to signal fidelity, the system platform may mask user-identifiable indicators, or use only class estimates. When sharing biosignal data with others, measures are defined, but the system platform may not share how these measures are derived from each person. For example, where there is a happiness measurement, the system platform may share the score but have no absolute accuracy. As there is no sharing of how the scores are computed, there is less of a security risk of sharing personal information. Use-only features such as event information may be shared instead of user-identifiable features. The system platform may only provide for sharing of timing features of the signal rather than the signal itself. This process of anonymization may be similar to a process of phase correlation. A recipient could not reconstruct the signal but the signal carries timing information. Examples of data that may be shared: audio features that mark when people start and stop talking; EEG features that mark when the user exhibits an ERP or ERN; and heart rate ("HR") features that mark significant increases or decreases in HR.

Physical and mental state classification and activity classification may be implemented by the system platform. A list of rules may be maintained identifying which users have access to what classes, and at what resolution. Security encompasses class specificity and temporal localizability.

There may be blurring of classes since some classes might be considered more private than others. Some activities may be considered by the user to be shareable, while others are not considered to be shareable (e.g. doctor visits or therapy sessions). A mental state estimate may be shareable but not the context. Instead of sharing a high granularity of affective state, the system platform may be configured to share that is negative or positive neutral energy. The shared measurement may be too heavily quantized to yield a definitive indication of happiness or sadness.

Temporal aspects of class estimates can be blurred (e.g. provide average mood for the last day rather than a minute by minute account). The user may allow detailed analysis to certain individuals, or perhaps to certain individuals when the user is located in close proximity to the certain individual.

Often the purpose of sharing data is to do correlational analysis or other data mining operation over an individual's (or group's) data with respect to another data set of interest. For example, if you wanted to find out how many people were happy all at the same time during the experience of listening to a specific song. The system platform which may be considered as trusted will be able to do more sophisticated correlational analysis of sensitive information and may not require that it is transferred to a untrusted party. The sophisticated methods of EEG and related analysis are sufficient to ensure that the system platform cannot be abused to retrieve sensitive information through the joint analysis of bogus data and sensitive user data that is under attack. For example, a song in question could be uploaded to the server. The system platform could discover what users have listened to the song, and a secondary operation could collate the responses and report back anonymous statistics that respect privacy settings of individual users.

Sensor Types

Many sensor types may be used to obtain data from the user or regarding other properties or events, including, but not necessarily limited to the following: 3 axis Accelerometers; Acoustic; Air velocity; Gas detectors; humidity sensors; weight scales; infrared camera; magnetic fields; pH level; Speed; atmospheric pressure; Blood glucose; Arterial blood pressure; Electrocardiography; Temperature; Respiratory rate; Pulse oximetry; environmental (e.g. thermometer); brain activity measurement devices (e.g. EEG for FNIRS); cardiovascular activity through ECG or pulse oxymetry; muscle activity using EMG; breath measurement using strain sensors; skin conductance; body motion using inertial sensors such as gyroscope and accelerometer; environmental sound (microphone); environmental visuals (video and images); media players; geographical based context; tasked based context; telephone calls; email reading and composition; and internet searching and reading.

Bio-signal data may include heart rate or blood pressure, while non-bio-signal data may include time, GPS location, barometric pressure, acceleration forces, ambient light, sound, and other data. Bio-signal and non-bio-signal data can be captured by the internal sensors 106, external sensors 104, or both.

Sharing Data

Figure 3:
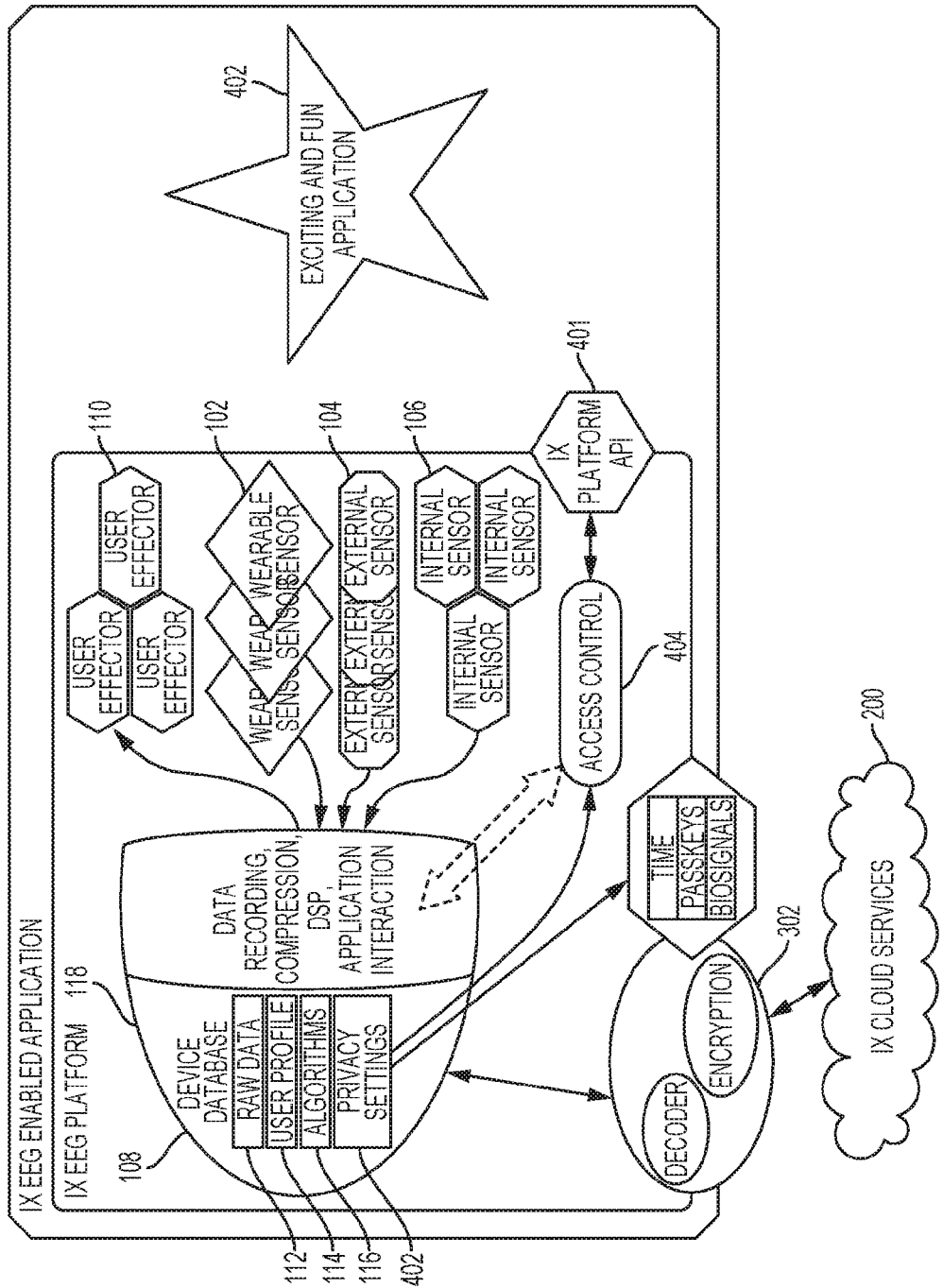
FIG. 3 illustrates an embodiment of a cloud service model in accordance with the invention, and further including integration with a third party application integration.

Referring now to FIG. 3, in a non-limiting exemplary embodiment, the client device or devices may have an interface for sharing, with third party applications 402, user profile data 114 or system functionality. This interface may include, for example, access to sensors and software used to process and analyze data. This interface, for example, could be an application programming interface (API) 401 that third party developers may use to access data and functionality associated with a client device. API 401 may provide access to the SAAS platform 200 through the client device API.

In order to protect the user's privacy, a user may be required to grant access rights to certain data for certain applications. In an example embodiment, the client device 108 may allow a user to set privacy preferences 402 related to user profile data 114. These privacy preferences may then be used to control the data available to third party applications or the SAAS platform 302. In the case of availability to third party applications, the client device may have an access controller 404 configured to control user profile data 112 access based on privacy settings 402. Other techniques for controlling access to resources may likewise be employed.

In another broad aspect, a method is provided for collecting bio-signal and non-bio-signal data from a user, processing the bio-signal and non-bio-signal data, analyzing the bio-signal and non-bio-signal data, and sharing the analyzed bio-signal and non-bio-signal data with third party applications, clients, and organizations.

Possible MED-CASP system features of the present invention include: Uploading brainwaves & associated sensor and application state data to cloud from mobile application; Downloading brainwave & associated data from cloud; Real-time brain-state classification to enable BCI in games or other applications; transmitting real-time brain-state data to other users when playing a game to enable multi-user games; Sharing brainwave data with other users to enable asynchronous comparisons of results; Sharing brainwave data to other organizations, third party applications, and systems; sharing brainwave data with other applications on mobile devices through a cloud services web interface; and Sharing brainwave data with other applications running on client devices or other devices in the trusted network such that brainwave data can control and/or affect other devices.

The system platform may provide the ability to use pre-compiled algorithms supplied by a third party within the system platform library, including the ability for a third party who is using the system platform library, to use the third party's own developed algorithms with the system platform library. The system platform may allow users to build and participate in communities of like-minded meditators, for example by enabling real time coaching from a remotely located meditation coach using the system of the present invention.

In one implementation, based on permission by a first user, a second user may be notified when the first user is using the meditation application, and may enable the second user to access a dashboard that enables in real time or near real time to track the progress of the first user. The system platform may enable the second user to provide encouraging guidance or messaging to the first user for example by providing a voice link or to enable the integration of messages from the second user into an interface presented by the client application of the first user.

The present system may include a social media layer that allows users to "friend" one another based on shared attributes such as similar interests, similar profiles (including for example similar pace or challenges in achieving meditative states for example or differences in profiles that suggest that a first user may be able to assist a second user in achieving defined objectives). The social media layer may enable a variety of social interactions between users, including for example support provided by one user to one or more other users in achieving goals of applications. Support may be expressed by sending supportive messages, encouraging digital media objects such as badges and so on. Various other implementations are possible.

The present invention may give feedback to the user. This may be accomplished using the latest research in the EEG/meditation field to provide to the user the most accurate measures known to facilitate the user's learning. A user may be assisted in meditation by allowing the user to observe the user's progress and provide motivational support for the user's meditation practice.

In one implementation, a user wears a brainwave headset that is connected to the user's mobile phone while the user's meditates. An application on the phone processes the brainwaves and provides feedback about the user's brain state using neurofeedback to help the user achieve deeply meditative states and to speed the user's learning of meditation states. On the mobile device, the user's data is recorded and will be used to generate a personal meditation history that shows the user's progress over time.

The present invention may provide for integration of pre-meditation and post-meditation collection of subjective experience factors (such as the user's mood and level of alertness to support more comprehensive results to the user and provide features to be used in the server side algorithm improvement engine). The user may therefore be able to track qualitative aspects of the user's practice and see trends that can improve motivation and speed. Survey answers also allow the meditation experience to be tailored to suit user preferences.

Program tools to download brainwave and associated data from the cloud may be used and conversion into MATLAB™ and PYTHON™ data formats may be provided.

Integrating audio feedback may allow the user to know when headset signal quality is poor, or when other program functionality is impaired.

Implementing a meditation timer with bell stimulus that can be time locked to EEG analysis may support stimulus entrainment ERP analysis.

Pod™ player integration (or integration with other wireless devices) may be provided, to synchronize music with EEG collection to support time locked stimulation and analysis relating to music. Synchronizing music in this way is related to measuring meditation performance as well as implementing a music recommendation system.

Incorporating an attentional blink cognitive test for meditation progress scoring may be provided.

Use of acoustic entrainment based meditation performance measures may be provided.

Multi-stable perception analysis, using visual illusions such as the Necker cube, Schroeder staircase and Rubin's vase, to measure EEG dynamics related to cognitive re-framing may be provided.

Other features may include: choose your own adventure-style decision tree for meditation education and presentation sequence, constructive feedback and encouragement; environmentizer for voice in guided meditation; Mr. Potato head-style body scans; Chest and head breath movement analysis; Hands fidget analysis; hands breath counting; phase locked loop rhythmic entrainment (i.e. rocking of body); rhythmic breath; rhythmic alpha and or theta; and Paired Synchronization meditation; and standing balance meditation and yogic poses before and during meditation.

An augmented reality meditation environment may be provided where visual world changes when in different phases of meditation.

SAAS

Any functions performed by the client device or devices could also be performed by the SAAS platform 200. Raw data collected from internal and external sensors may be sent directly to a SAAS platform for processing, analysis, and storage. However, bandwidth limitations, may require that at least some of the processing and analysis is performed on the client device(s) prior to transmission to the SAAS platform 200.

The SAAS platform 200 may also be used to perform computationally complicated or expensive tasks that may not be performed as efficiently or effectively on the client device or devices. Furthermore, the SAAS platform 200 may be used to store user data for many users. Since it can store data for many different users, the SAAS platform 200 may also analyze data associated with one or more users. This aggregate data analysis may be used, for example, to determine recurring patterns for various groups of users.

In an example embodiment, the SAAS platform 200 may comprise a cloud-based database 202, an analyzer 204, an algorithm collector 206, and an algorithm improver 208. The cloud based database may store all, or a subset, of the raw data 112 associated with a user profile 114. The database may also store user data that has been pre-processed or analyzed by the client device or devices. Alternatives to cloud-based databases could be used.

Similar to the client device or devices, the analyzer 204 in the SAAS platform 200 may be used to process and analyze raw data collected by internal and external sensors. Additionally, the analyzer 204 may be configured to utilize algorithms stored in the algorithm collector 206 to process and analyze both raw data and user profile data.

In addition to analyzing data associated with individual users, the analyzer may analyze aggregated data (data associated with one or more users). Aggregate data analysis, may provide insight into brainwave patterns for a particular population. An analysis over a set of users may indicate, that one or more patterns of features as extracted by the feature extractors discussed earlier are associated with a specific mental state for certain types of users.

In one example embodiment, the analyzer 204 may utilize a machine learning algorithm stored in the algorithm collector 206 to identify and, correlate patterns with specific types of users. These algorithms, for example, may identify patterns common to many users. More than one machine learning algorithm can be stored in the algorithm collector 206 and multiple algorithms may be supplied to the analyzer 204 depending on the circumstances. Another embodiment might allow third party applications or other parties to supply their own custom algorithms into the algorithm collector 206 so that the custom algorithm may be used by the analyzer 204.

The analysis results can be used by an algorithm improver 208 to improve the algorithm for future analysis. For example, analysis of the data may uncover different brainwave patterns for different classes of users that may correlate with specific physical or emotional states. These patterns can then be used to update the algorithms so that these patterns are used in the analysis of data collected in the future. There may be correlations found between specific groups of users with a specific set of characteristics. These correlations may be used to improve the performance of the analyzer 204, algorithm collector 206, or algorithm improver 208, or other aspects of the systems or methods.

Improving the algorithms may also comprise a feedback mechanism to allow users of the system to judge the correctness of the analysis. That is, a feedback process may be used to allow the user to evaluate or supervise the machine learning. This feedback mechanism, in an example embodiment, can be a part of the algorithm improver 208. For example, a user of the client device may be asked whether a particular analysis corresponds with a particular emotion or physical movement experienced at the time the bio-signal and non-bio-signal data was collected. This can be useful where there is more than one pattern for a known physical or emotional state. The feedback mechanism may allow supervisors to review the aggregate data analysis for correctness. The feedback mechanism may allow supervisors to tune the aggregate data analysis algorithm to identify and ignore aberrant data.

The algorithm improver 208 may be used to re-analyze the data. This re-analysis can both validate and improve the analysis algorithms. The algorithm improver 208 may first update the analysis algorithm in the algorithm collector 206. The data may then be re-analyzed by the analyzer 204 using the updated algorithm stored in the algorithm collector 206. Also, the algorithms 116 on the client device or devices may be updated over the connection 301 by the SAAS platform 200. The algorithms may be improved through machine learning applied to collected data either on-board the client device or on the server. EEG data may be saved along with application state to allow a machine learning algorithm to optimize the methods that transform the user's brainwaves into usable control signals.

In another embodiment, the SAAS platform comprises an interface for sharing stored and analyzed user data to other client devices, organizations, or third party applications. As can been seen in FIGS. 1 and 2 for example, examples of other client devices, organizations, or third party applications 500 can include untrusted devices, the public, friends, trusted devices and third party applications. These devices, organizations, and applications can connect to the system via wired or wireless connections 301, for example over the internet. Furthermore, these connections may also be encrypted 302 using similar systems and methods described above.

Figure 4:
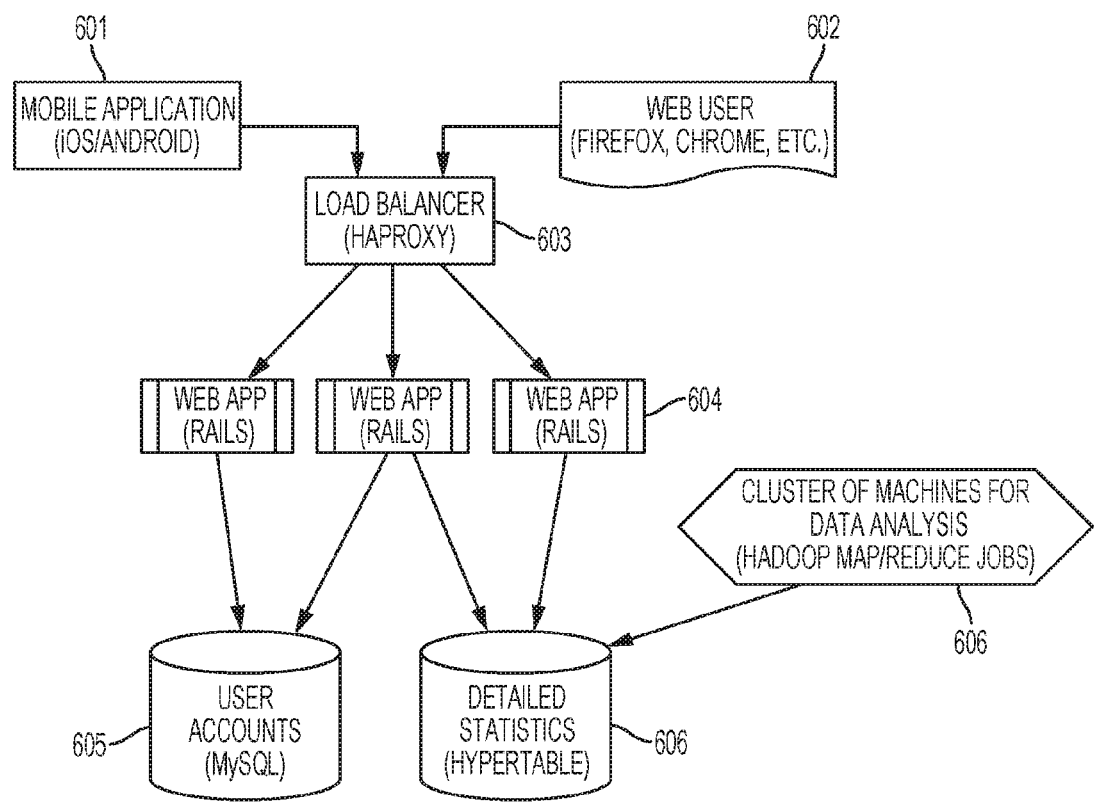
FIG. 4 illustrates an embodiment of the architecture of a cloud service platform in accordance with the present invention.

FIG. 4 shows an example embodiment of how the SAAS platform 200 might be implemented. In FIG. 4, the mobile application 601 and web user 602 may represent the client devices, organizations, or third party applications 500 as discussed above. In this example, requests from these applications would first go to a load balancer 603, an example of which would be an HAProxy™. The proxy, based on the load of particular web servers would then route requests to one of at least one web application servers 604. These web application servers may be standalone servers, or these web application servers might also be virtualized servers running on hosting infrastructure such as Amazon's EC2™ platform or using VMWARE™ technology. These web applications may also be implemented using a variety of development languages or platforms. In one example of the implementation of the present invention, the web application may be implemented using Ruby on Rails™. These web applications may store user data for example in a mySQL database 605. These web applications may also store data or detailed statistics on other storage systems, e.g. Hadoop. In this example, data analysis of large sets of data may be performed by a cluster of machines configured to communicate with the data store of the web application.

Figure 18:
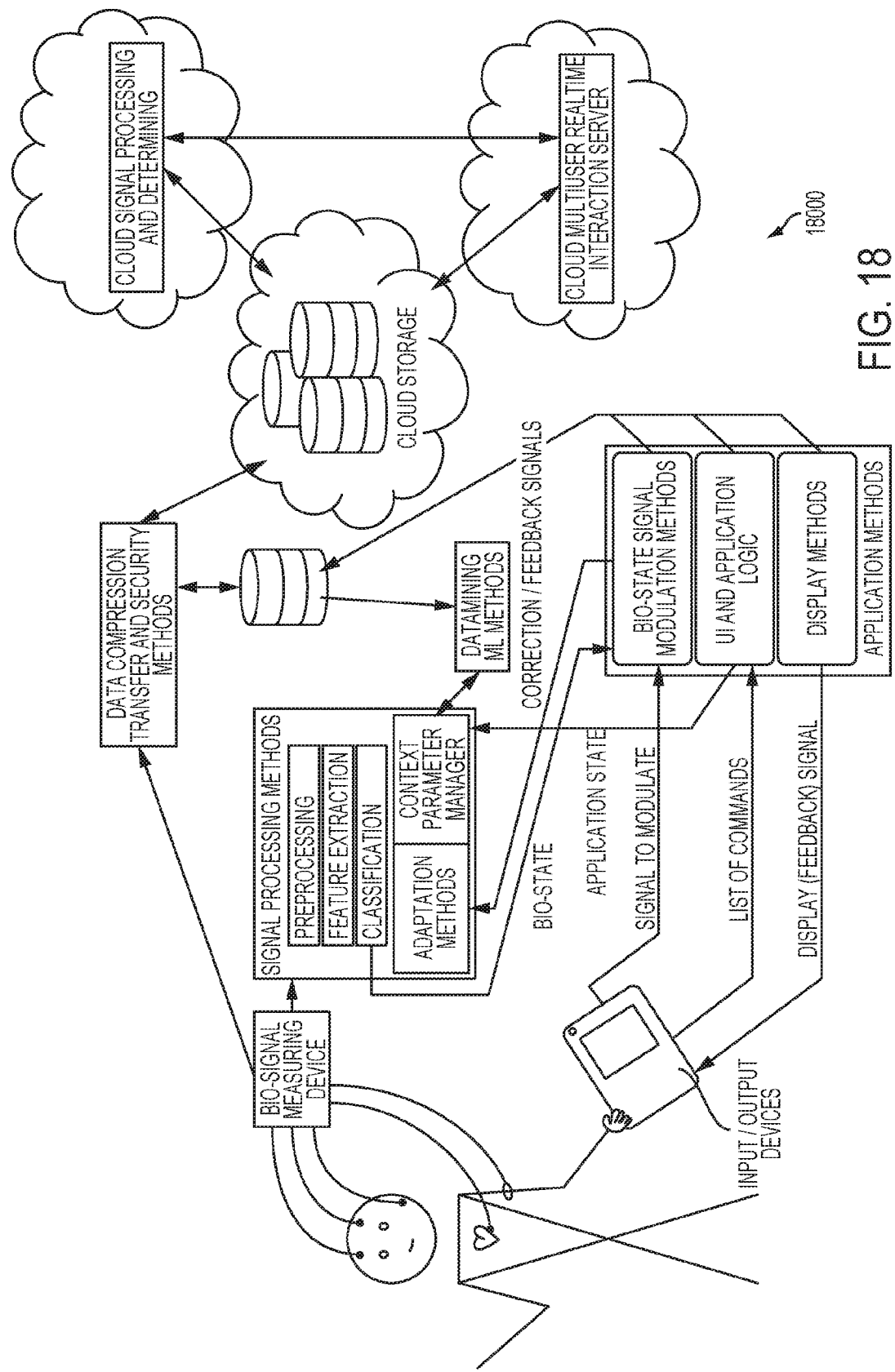
FIG. 18 illustrates an embodiment of the platform of the present invention.
Figure 19:
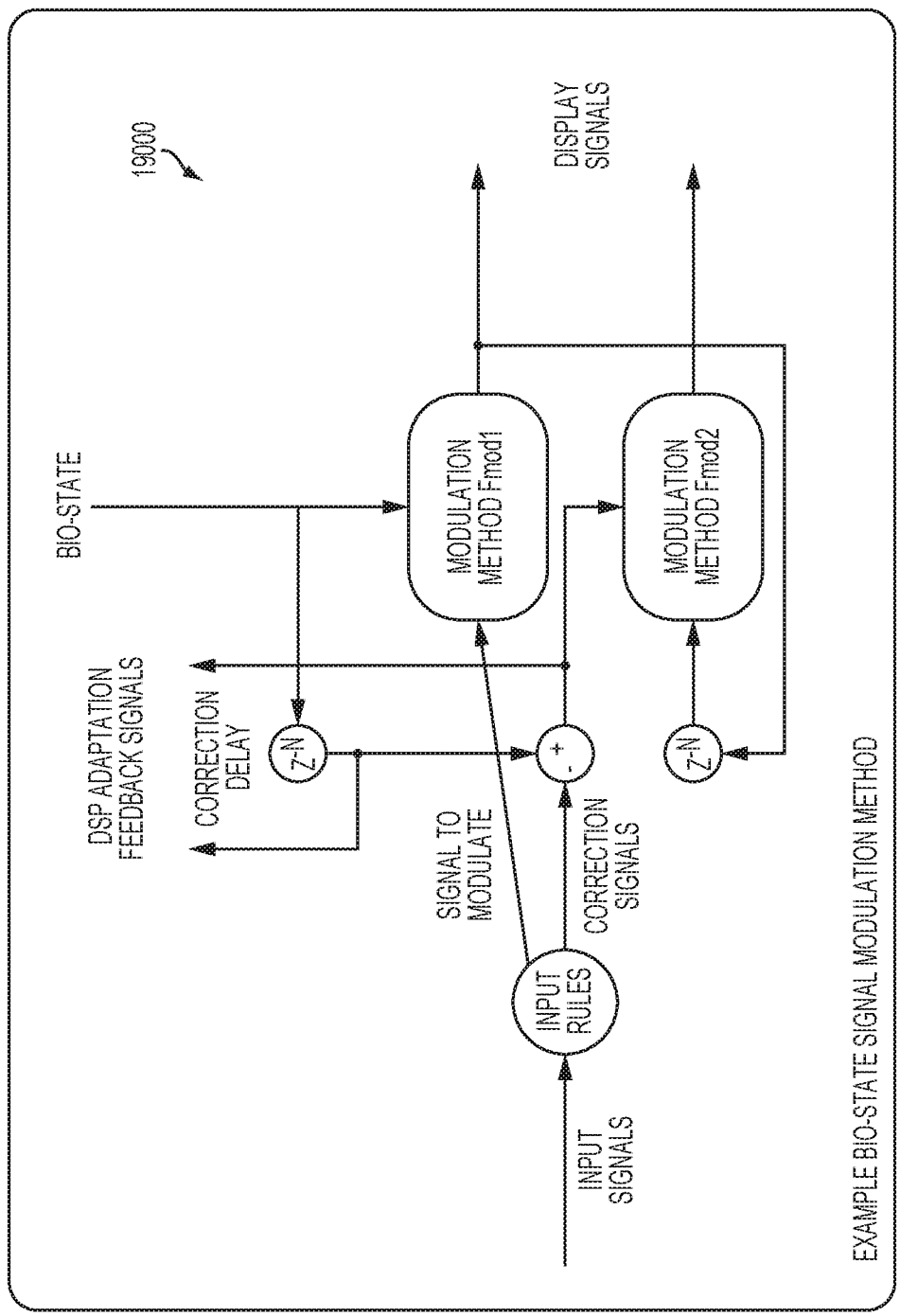
FIG. 19 illustrates an embodiment of a bio-signal state modulation component of the embodiment of FIG. 18.

In accordance with aspects of the present invention, an implementation of the system platform (e.g. 18000, 19000) is shown in FIGS. 18 and 19.

Other example aspects and embodiments of the systems and methods of the present invention are described below.

Meditation Application

According to an embodiment, systems and methods for a meditation biofeedback application are provided. The embodiment comprises a mobile meditation solution including an EEG headset bundled with an application that measures a user's brainwaves while the user meditates and tracks the user's progress over time. The product may be configured to be functional out of the box and deliver particular benefits (reduced stress, improved mood, increased effectiveness in the workplace, etc.). The application may be implemented to a range of different platforms such as iOS™ and Android™, and may help a user to learn to meditate. The application may allow a user to observe the user's progress and provide motivational support for the user's meditation practice. The application may allow a user to build and participate in communities of like-minded meditators, for example by enabling real time coaching from a remotely located meditation coach using the system of the present invention. The application may use updated research in the EEG/meditation field to provide the user the most up to date measures known to facilitate the user's learning In one implementation, based on permission by a first user, a second user may be notified when the first user is using the meditation application, and may enable the second user to access a dashboard that enables in real time or near real time to track the progress of the first user. The system may enable the second user to provide encouraging guidance or messaging to the first user for example by providing a voice link or to enable the integration of messages from the second user into an interface presented by the client application of the first user.

In one implementation, a user wears a brainwave headset that is connected to the user's mobile phone while the user meditates. An application on the phone processes the brainwaves and gives the user feedback about the user's brain state using neurofeedback to help the user achieve deeply meditative states and to speed the user's learning of meditation states. On the mobile device, the user's data is recorded and will be used to generate a personal meditation history that shows the user's progress over time.

The user's data can be processed and analyzed on the client device, or the data can be uploaded to a cloud database for processing and analysis. For example, the user's data is uploaded to a cloud database where machine learning algorithms can process the data and thereby customize the brainwave processing algorithms to better fit the user's brainwaves. The adaptations are then offered back to the user through the user's online profile, to enhance the user's experience.

Implementations of the application of the present invention may include one or more features, including live group guided meditation, where the instructor receives real-time information about the brain states of the subjects. Subjects may also be able to receive updates from each other including real-time brain state and other relevant measurements such as breath phase.

Another feature may be integration of pre- and post-meditation collection of subjective experience factors, such as the user's mood and level of alertness to support more comprehensive results to the user and provide features to be used in the server side algorithm improvement engine. This may allow the user to track qualitative aspects of the user's practice and see trends that can improve motivation and speed progress. Survey answers also allow the meditation experience to be tailored to suit user preferences. The present system includes a social media layer that allows users to "friend" one another based on shared attributes such as similar interests or similar profiles, including for example similar pace or challenges in achieving meditative states for example or differences in profiles that suggest that a first user may be able to assist a second user in achieving defined objectives. The social media layer may enable a variety of social interactions between users, including for example support provided by one user to one or more other users in achieving goals of applications. Support may be expressed for example by sending supportive messages, encouraging digital media objects such as badges and so on. Various other implementations are possible.

Another feature may be cloud based extensible user profiles for personal information; settings and algorithm parameters that are continuously tuned (through the use of the application) to be improved or optimized for the specific user; hardware setups and application specific parameters; ad relevant training data. This may allow application usage to be device independent, and allow for back compatibility as the application is improved.

Other features may include: augmented reality meditation environment where visual world changes when in different phases of meditation; program tools to download brainwave and associated data from the cloud and convert into MATLAB™ and PYTHON™ data formats may be provided; integrated audio feedback to allow the user to know when headset signal quality is poor, or when other program functionality is impaired; meditation timer with bell stimulus that can be time locked to EEG analysis to support stimulus entrainment ERP analysis; IPod™ player integration (or integration with other wireless devices), to synchronize music with EEG collection to support time locked stimulation and analysis relating to music (this may be related to measuring meditation performance as well as a music recommendation system); an attentional blink cognitive test for meditation progress scoring; use of acoustic entrainment based meditation performance measures; multistable perception analysis, using visual illusions such as the Necker cube, Schroeder staircase and Rubin's vase, to measure EEG dynamics related to cognitive re-framing; choose your own adventure style decision tree for meditation education and presentation sequence, constructive feedback and encouragement; environmentizer for voice in guided meditation; Mr. Potato head body scans; Chest and head breath movement analysis; hands fidget analysis, hands breath counting; phase locked loop rhythmic entrainment, such as rocking of body, rhythmic breath, rhythmic alpha and or theta, and/or Paired Synchronization meditation; and standing balance meditation and yogic poses before and during meditation.

Compare-Your-Brainwaves

In one possible extension of the present invention, each user wears a brainwave headset connected computing device. A sample of each user's brainwaves is taken, while resting or while performing a certain activity. These brainwaves are then uploaded to the cloud where a cloud implemented resource implements one or more processing algorithms for rating the brainwave samples according to several criteria. The results of this analysis may be compared with that of other users, either friends from a social network for example, random users from the public or celebrities, who collected their brainwave data in a similar test. The comparison data is then sent back to the client application on the mobile device, where users can see how similar they are to one another. Music experience vectors ("MEV") can be stored in the cloud that list the music and the brainwave analysis results that lead to the music rating.

In another possible related implementation, music recommendation engine based on brainwaves may be provided. In this case time-locked brainwaves may be recorded as a user listens to a particular piece of music. This brain state data is reduced to a lower dimensional MEV that encodes time locked attentional entrainment. In one aspect, the music recommendation engine may compare the user's MEV with MEVs of other users listening to the same song to identify other users that have high MEV correlation. Because of the time-locking between the MEV and the piece of music that was listened to, users that have highly correlated MEVs are likely to respond to similar parts of the song in question, and are thus likely to experience other songs similarly as well. This music recommendation engine can then create a set of recommended songs that are new to the user that are liked by other users with similar MEVs, or it may suggest a social connection with other users of similar taste. The recommendation could incorporate many MEVs in its user matching processes.

Quantified Self Integration

The present system may be integrated with other "quantified self" products such as the Jawbone UP, Fitbit, BodyMedia, heart-rate monitors and the like. For example, data from these third party systems may be obtained and synchronized with data created by the present system, for example its MED-CASP system implementation as described. In one implementation, the system of the present invention may transform ambiguous intangible brainwave data to clear tangible information which is then processed and transformed into info-graphics and self-metrics serving as a tool to measure and increase an individual's human capital. The system would be designed for use in everyday life, recording a user's brain-state over the course of an entire workday. At the end of the day, the user would download that day's data into a computer, which would analyze it and compare it with previous data looking for patterns. The computer would prompt the user to enter details about the day's activities, and then correlate them with the user's brain states.

Epilepsy Monitor that Lets Your Doctor See Raw Data

In another possible implementation of the present invention, an improved epilepsy monitor system may be provided. In this aspect, an epileptic patient wears an EEG headset that records the patient's brainwaves throughout the day and streams the brainwaves to a client application on a mobile device. In the event of a seizure, the application may notify automatically the patient's doctor, contact emergency services via Internet connection, and/or provide context information such as GPS and auditory environment, and brainwave history pre and seizure as well as real-time EEG data.

EEG+Augmented Reality

Use of visual feedback for neurofeedback may be desirable however it is not necessarily compatible with real world applications since the user is typically using the user's vision to achieve a primary task and having to look at a screen disrupts this. Augmented reality ("AR") generally refers to technologies where the users field of view ("FOV") is augmented, or otherwise changed, by computer graphics. AR would allow a user to receive biofeedback naturally, in a way that that can be integrated into many different experience and applications. In one implementation, an augmented reality system may be provided that includes or links to the system platform of the present invention. The augment reality system may include a wearable display (often called a heads up display). Possible features of an augmented reality system based on the present invention may include: identification of brain states, specific to the AR context, that utilize context information from the inertial tracking and the computer vision processing done within the partner companies' aspect of the application. This may include, for instance, the identification of P300 waveforms time locked to visual events in the AR field of view.

A system platform employing ERP or other brainwave features may be able to determine if there are visual events in the users FOV that are significant. A surprising or significant occurrence may be observed, including, for example, seeing a car that the user likes, or witnessing a threatening event that could cause the computer system to go into quiet mode and allow the user to concentrate more on the user's environment rather than the computer world. The system platform may be configured to record the faces of other people that the user recognizes or wants to remember. The system platform could maintain a database for a new individual that the person has met, or will meet. The system platform may take pictures or start recording video if the visual information is salient or interesting to the user.

Many applications can also be built that leverage the features of the technology directly. For example, an application may be built that allows a user to see another person's brain state rendered in real time emo-graphics (i.e. perhaps around the other person's head or body) to enhance social interactions over lower than real life bandwidth channels, or to enhance interactions between strangers or between people who speak different languages.

For example, when the user looks at a person with whom the user is conversing, people who are upset could have storm clouds rendered above their heads, or people who are happy could have sunshine streaming from them. People who are thinking could have the gears turning rendered above them with computer graphics. People who are relating socially to others in their proximity could show lines of interaction between themselves and the people with whom they are relating as lines of coherence between people. It would be useful for some interactions to show the coherence between the users brainwaves and another, both the people who the user is communicating with or perhaps even those with whom they are relating but without direct verbal contact. Accordingly, such an implementation may help users to synchronize which may ultimately affect the quality of communication and the feeling of connectedness between people.

EEG Capture System for Visual Salience Monitoring for Video Summarizing, or Image/Video Tagging.

In another possible implementation, photos or videos that are captured by an operator using a MED-CASP system may be tagged with brain state for searching and annotating by/with affective state. Videos may be auto summarized at different scales based on TF analysis, visual or auditory ERPs or other EEG processing technique.

For example, output of a digital camera or video camera may be tagged with brain state information. Augmented reality devices that incorporate a camera (like Google Glass) may be configured to record video (of what the user sees) along with brain state information, or, for example, "find me all the videos I took where I was really happy, or in Flow". Tagged video may be searched for highlights of the user's day where "highlight" is determined through affective/cognitive state as determined using brainwaves and other biometric information. The system platform or connected AR device may display the times in the day where the user was distressed, and may therefore allow the user to start to understand the user's emotional triggers and relationships.

Software Development Kit (SDK)

A software development kit may be provided which allows third parties to develop applications using the system platform product. The SDK may provide third parties: to access the raw brainwave data; plug in new algorithms for DSP processing; plug in new algorithms for the interpretation of the DSP data; and display monitoring data as to the current state of the headset, FFT algorithms, DSP algorithms, and application-level algorithm data.

Team Based Applications

In a non-limiting exemplary implementation of the present invention, information about teams and results can be stored in the User's Profile. A team (group of users with a headset device) can be formed around a common goal or principles. Teams could, for example, participate in contests, collect awards, and participate in simultaneous live events where groups compete or collaborate with each other. For example, in one application, a team may collectively collect points toward a goal. Teams have common properties such as a team name, description, list of team members, apps they participate in, individual rankings for each app, and overall team standing versus other teams. A facility may be provided for individuals to search for teams and for teams to advertise themselves. A single team may participate in multiple applications. An application may be participating simultaneously or asynchronously while being either disconnected from the Internet or connected through the respective team member's mobile device. A disconnected app could be operating on a local wired or wireless network. A team member can view the collective data for a team as well as view information about other participants.

Shared Experiences LED by a Facilitator

Sessions and results can be stored in the user's profile. Participants join a "room" which connect participants together. One of those participants is a facilitator or "group leader" (GL) who guides the group on a shared experience. To aid the group leader in his/her task, a dashboard is displayed on the GL's device which allows the monitoring and/or communication with each participant. The group leader can send messages to the participants (such as text, voice, headset data) either publicly or privately. The GL can create or delete rooms, allow participants into the room, or remove them from the room, or set rules for the room. Room rules may include: anyone can join; need a security token to join; whether the session is being recorded; allow/deny user-to-user communication; allow/deny public broadcasts messages from participants; allow/deny participants to see identifying information about other participants; and provide one or more participants with permissions to manage the room and/or other participants. The group leader can be connected to more than one room at a time. Each participant may be able to monitor and/or communicate with the group leader. A participant can be connected to more than one room at a time. A participant's client computing device: may upload live brainwave data or previously recorded brainwave data; may choose to expose identifying information to other participants; and may send private or broadcast messages to other participants. This functionality may be implemented using a server over the Internet, or other communications network, as a relay device, or the application could be run disconnected from the Internet over a local wired or wireless network. The server may be used as an additional source of processing power to aid in the group experience, such as generating additional display data.

Sleep Monitoring and Aid Device

In another possible implementation, the system platform of the present invention may be adapted to provide an overall solution that adapts sleep algorithms to particular users. The system platform may offer unique functions, which may include: environmental control of music or lights (e.g. dimming the lights or turn off the lights while when the user falls asleep); working with a meditation trainer application as part of the sleep therapy; real-time sleep competitions with friends to incentivize users who typically stay awake late at night to go to sleep earlier; use the collected EEG data to create artistic representations of the user's unconscious hours; and provide specialized algorithms to facilitate dream states and lucid dreaming. Sleep results and analysis can be stored in the user's profile Social Applications The system platform may provide for the ability to share a neurofeedback visual and auditory experience with others. This could be done synchronously in realtime in a one to one fashion or in a broadcast fashion (one to many) or it could also be done in a multiway fashion (sending to many and receiving from many in a group). This could also be done asynchronously, where the user can send or others can browse and choose to view someone else's shared experience stored in the cloud. There are multiple network configurations for this type of social engagement between users, and it could occur via direct peer to peer connection, via local network or via the system cloud infrastructure.

The general architecture for this backend model may be similar to a publisher subscriber design where each node in the network (an individual user) is both a publisher of content as well as a subscriber to other users or the cloud.

White Labeled Platform as a Service

A backend of the system platform may be designed in a modular fashion such that each module has configuration and meta parameters such as versioning so that it can be partitioned and subselected for release to a client as an individual platform. Meta parameters such as sharing or SDK level may allow to selectively share particular features and identified algorithms with particular partners or retain them internally. This has implications for a tiered SDK as well as tiered cloud server API.

Experiment, Research and Scientific Study Tool

Results learned in studies can be used to update a user's profile based on the information in the user's profile. For example, the user's profile may be updated to state that, based on the user's brainwaves and other information the user is at a higher risk for developing disease X.

The cloud may support conducting medical, anthropological or social studies with the data contained in the cloud. The system platform may be used to design a study protocol and select study parameters. The study protocol and its parameters can include the definition of the population to be studied (e.g. ADHD diagnosis compared to normal), and the type of study to be conducted (e.g. randomized clinical trial (RCT), prospective or retrospective longitudinal cohort studies, cross sectional studies, pilot studies or other observational or clinical type of studies). A software based controller in the cloud can then execute operations for querying and selecting users, in a randomized fashion to belong to different study arms (e.g. sham versus neurofeedback). If the study is prospective or a comparison type study (e.g. RCT of different algorithms or treatment effects) then instructions may be given to users specific to each arm of the study for them to follow. The controller can then provide alerts to users to ensure that they are complying with the study protocol. Then the controller can gather the data relevant to the study, anonymize any identifiers and build a data set that can be analyzed offline by a human analyst or automatically online by study software built-in the Cloud platform.

The backend cloud system may be designed to serve as an external and internal research tool. For internal research the cloud system will serve as a driver for A/B testing with subsets of the user population for algorithm or application or user experience experiments. This testing infrastructure may also be useful for external clients or researchers looking to run targeted experiments on specific cohorts within the general population, such as a focused attention test for ADHD patients in a given age range vs. a similarly aged control group. An example of this type of configuration is shown below in Figure Group Experiments.

Affect Sensitive Cell Phones

In another possible example of use of the present invention, a mobile phone may be modified, and integrated with the MED-CASP system implementation of the present invention in order to (A) selects ring-tones and (B) scale ring volumes to match the user's emotional state and level of distraction. This would enable the system platform of the present invention to behave like a private secretary who is tuned into the user's mood. The user profile can provide information to drive mood enabled apps.

Distraction Monitor

In another possible implementation of the present invention, the computer system of the present invention may be configured to act as a distraction monitor. This may be used for example to improve the social aspects of telecommunication, or to communicate the cognitive state and level of distraction of the person that the user is talking with. For instance, this would allow for cognitive state feedback of a cell phone user that is driving. The system would be able to inform the other user of the relative balance of attention between the conversation and external factors where the parties to the conversation are remotely located. This type of information would normally be visibly communicated between conversation participants located at the same location.

Affect Controlled Music Player

In another possible implementation, EEG based affect measurements may be linked with music libraries, and these measurements may be tagged for mood transition probabilities of specific music. One implementation of a computer system configured using the present invention may enable a user to choose a target brain state or mood, and the computer system may automatically generate a playlist of songs associated with that brain state to facilitate a brain state transition or state reinforcement.

Radio DJ Feedback Machine

In another possible implementation of the present invention, computer systems may be provided that enable improvements to interactions with an audience. For example EEG based audience music feedback may be used by a particular implementation of the present invention for content control and selection. A listener a radio station (online or broadcast) may be listening using a mobile device enabled with functionality of the present invention, such as the MED-CASP implementation described previously. Processed brain-state data may be sent to the cloud from the mobile device, where it is shared with the DJ on the radio station. The DJ may be able to view all of the data from these users and to understand how the users are responding to his or her musical selections. From there, the DJ can adjust future selections or share that information with the audience.

Cloud-Based Movie Experience

In another related example, an entertainment system may be configured to (A) obtain statement of mind or mood information from an audience, and (B) adapt entertainment content (for example story ending) based on this information in order to achieve maximum effect.

Student Attention Monitor

In another possible implementation of the present invention an education monitoring system may be provided where students in a classroom are each wearing a brainwave headset which is monitoring their state of attention. The teacher is able to access their brainwave data from a dashboard at the front of the classroom, and can use it to monitor whether students are concentrating on their work or not.

Guidance, Feedback and Teaching of Users

In accordance with a non-limiting implementation of the present invention, the user may choose a goal that the user wishes to reach by providing an indication of the goal to the system platform. A guidance system component of the system platform in the cloud may then select a teaching program that is customized to the user's specific level for the goal in mind. The guidance system may conduct a survey to help the user clarify the user's goals and then choose an EEG acquisition protocol to help characterize a patient. A decision tree is consulted that maps the user's current state with respect to the goal and then recommends a learning program for the user. The learning program can include elements of neurofeedback plus other exercises for the user to complete. The guidance system can track a user's progress and provide encouragement, advice or alter the teaching program as required. The system uses EEG and other biological data to understand the user's emotional state and adjust the challenge of the learning paradigm according to the user's skill level. For example, high challenge and low skill may lead to anxiety which decreases a person's productivity and reduces the person's ability to learn. On the other hand, low challenge and high skill level lead to boredom which usually means a person becomes disinterested in continuing with the pursuit. A state of flow may be achieved where the challenge placed on a person is matched to the person's skill level providing for the person to be productive with seemingly little effort and negative emotion attached to the effort. The guidance system may determine a user's emotion and then adjust the challenge placed on a person so that the person is operating in a state of flow.

Monitoring Fatigue/Sleep in a Fleet of Truck Drivers

In this possible computer system implementation, truck drivers wear headsets that record their level of fatigue. The data from these headsets is sent through the cloud to the dispatch where dispatchers can monitor each driver and make sure that they are still able to drive safely.

Quality Assurance in a Factory

In this possible computer system implementation, workers in a factory wear headsets that measure their level of attention while performing sensitive work or potentially dangerous work. If a worker's focus drops while working on a particular piece of equipment for example, that equipment can then be marked to receive extra-attention in the quality-assurance process because of the increased likelihood of error.

Collective Brainwave Control

In other possible computer system implementations of the present invention, brainwaves may be obtained for a group of game players, and these may be processed to enable collective control such as in a cooperative multiplayer game. This type of interaction would be well suited to compassion training.

Brainwave Controlled Acoustic Attention Beam Forming.

In another possible computer system implementation the MED-CASP system implementation for example may incorporate a microphone array that enables thought assisted beam-forming to allow a user to enhance a user's ability to lock into directional sound in a noisy setting. The algorithm may for example associate dynamic changes in brain state with the persons desire to "tune in" to different aspects of the soundscape.

Brainwave Focus Disruptor/Encourager.

In another possible implementation of the present invention, the system platform may be configured to enable improved cognitive skills training for example using cognitive performance training, attention mastering and distraction avoidance. The system platform may be configured to affect the informatic channel between the user and their environment, to either help the user focus the user's awareness or to break free from something that is commanding the user's attention in a detrimental way. This includes for instance an EEG based information filter for web browsing or other computer use. For instance the system platform could help to make distracting advertisements or messaging disappear when the user is trying to work and are having trouble concentrating. Detection for such distractions or interruptions may be performed through theta band phase locking for visual and auditory stimulus. The system platform may also detect fatigue related zoning and break the user from mind traps such as video games and web surfing. These concepts can be ultimately applied to the augmented or mediated reality applications where the audio visual signals are first intercepted by a computer system before the user receives them and allows for intelligent intervention that can help a user filter out distracting information from the user's environment, so that the user can be less confused or overloaded.

Medical Applications

EEG signals along with other biological and non-biological data can be used to diagnose medical and or psychological disorders. Rules used for diagnosing can be learned from the data stored in the system platform. These rules can also be obtained from clinical practice guidelines or other evidence based medical literature.

ADHD—Diagnosis

Analysis of EEG signals can be used to classify a person as exhibiting attention deficit hyperactivity disorder ("ADHD") or not. A user may undergo a prescribed set of exercises while the user's EEG signals are recorded. The system platform may takes raw EEG signals from multiple channels across the scalp and remove unwanted artifacts from the signals and replace them with de-noised EEG. A Fast Fourier Transform applied to each EEG signal and theta and beta band power is determined. The ratio of theta/beta power is compared to a ratio and if it exceeds the ratio then the person is diagnosed as exhibiting ADHD. Enhancements to the invention include using transformations of the EEG signal to emphasize the contribution of some EEG channels over others and to consider the contribution of spatial patterns.

ADHD—Therapy

In another possible implementation of the invention, a computer system may be provided for ameliorating attention deficit disorder ("ADD") or ADHD symptomology. For example, a user (adult or child) may see his/her level of alpha, beta or theta waves as recorded from a 1, 2, 3 or 4 electrode system, while he/she is performing an everyday task. The information can be displayed on a smartphone, tablet, computer or other device. The information can be presented visually in the form of a graph, table, pictorial or rating system. It could also be represented audibly. In one possible implementation the form of a sound (e.g. pitch or volume) may be changed by the system platform as measurements of brain state changes. These changes could also be represented through vibro-tactile feedback.

This information about his/her brain state could be used to understand the user's level of ADD or ADHD symptomology, and the user could use the system to be encouraged or rewarded to remain in the state of high beta wave or high alpha wave or upper alpha, and low theta wave. The system may also implement SCP and gamma effects.

Output of real-time measures related to the user's brain-state and or brain-wave phase may enable applications that can modulate the presentation of stimulus so that the system platform may either emphasize or deemphasize the effect of the stimulus on the user. For example, timing the switching of images may be altered by the system platform so that a user is more likely to be able to remember the images.

The system platform could stop advancement of an audio book or media player when the user is not paying attention. This can also be used to challenge a user to stay focused on sensory input, such as the attention paced audio book, or to give the user a workout when watching television. The system platform could be configured to change television signal characteristics such as improving contrast, changing presentation of advertising, changing the frequency response of the audio or visual channel, or perform beamforming to accentuate a particular spatial domain. Stimulus modulation can be used to help a user snap out of laxity, or self-narrative, through highlighting sensory input.

The rules engine of the system platform may provide for the system platform to determine what settings should be emphasized or de-emphasized on a per-user basis. The user could have a distraction knob, that uses adaptive filtering to be optimize based on user settings.

Hack Your Own Brain Real-Time Graphing Tools

In another possible implementation of the present invention, graphic tools may be provided to aid human assisted pattern recognition of brain states. This aspect of the invention may involve the presentation of the accumulation of two dimensional feature space data that is the result of real-time feature (spectral or other) extraction on a user's brainwave data. The user may monitor the user's own brain-state in an open meditation (mindfulness) style, and simultaneously observe the graphical representation to find correlations between the user's brain-state or brain-state dynamics with the two dimensional feature subspace presented. The graphic tools may include settings for time lag presentation so that observations of the user's internal state and observation of the feature space can be serialized. Tunable temporal band-pass filtering of the feature space may be provided, which a user may configure using settings, in order to aid an experimenter in comparing state dynamics.

Cognitive Training EEG System, Including ADHD Treatment

In another possible implementation, a user wears a soft-band brainwave headset that is connected to their computer or mobile phone via BLUETOOTH™ while the user executes cognitive training exercises that are modulated by target brain-states. The design may enhance in-domain problem solving through practice and facilitates crossover through target state association.

For example, in one particular implementation a math problems game may be provided that utilizes EEG for scoring and difficulty scaling. For scoring, target brain states may be rewarded using point scaling and a/v embellishment. Problems may be provided where EEG controls difficulty (to make easier when in target brain states) through increased information to aid solution (like making hints visible), through the selection of easier problems and modulating time constrains.

In order to enhance skill crossover, appropriate brain states may be linked to incentives or rewards. Selection of these states may be based on cognitive training research. These brain states may be incorporated into a game environment. Examples of target states may include: sustaining a beta brainwave during problem solving such as math or memory, seek and find, and matching tasks; and sustaining alpha brainwaves while performing mental rotation. In all tasks beta brainwaves may result in a change in the level of difficulty of the game, affect audio or affect displayed content on a display of the client computing device.

A Text Editor that Varies Font (Size, Shape, Colour) with Mood

A further example of an implementation of the present invention includes a text editor that automatically adjusts the font used when a user is typing, based on the user's brain state.

In-Flight Entertainment System

In another possible implementation of the present invention, an in-flight entertainment system may be provided that combines brainwave input, and audio/visual output on an airplane. Biofeedback may be provided to attempt to make travelling by air more pleasurable to passengers. The system may be configured to help a user of the system to relax, and control anxiety.

General

In accordance with aspects of the present invention, there is provided a system comprising: at least one client computing device; at least one bio-signal sensor at and in communication with the at least one client computing device; and at least one computer server in communication with the at least one computing device over a communications network; the at least one client computing device configured to: receive time-coded bio-signal data of a user from the at least one bio-signal sensor; transmit the time-coded bio-signal data and acquired time-coded feature event data to the at least one computer server; receive from the at least one computer server a user-response classification of at least part of the time-coded bio-signal data based on an identified pattern of correspondence between the at least part of the time-coded bio-signal data and at least part of the time-coded feature event data at least one respective time code; in accordance with a received input confirming the user-response classification, update a bio-signal interaction profile at the at least one client computing device with the user-response classification, the at least part of the time-coded bio-signal data, and the at least part of the time-coded feature event data at the at least one respective time code. By classifying the user's bio-signal data with a particular user-response classification, the system may provide for more accurate, or more responsive interpretation of user bio-signal data received at the at least one client computing device.

The at least one client computing device may be further configured to transmit a confirmation of the user-response classification to the at least one computer server. For example, the user may be asked to confirm the classification of the user's bio-signal data as a particular user-response. The at least one computer server may be configured to update a bio-signal interaction profile associated with the user at the at least one computer server with the user-response classification, the at least part of the time-coded bio-signal data, and the at least part of the time-coded feature event data at the at least one respective time code, based on the confirmation received from the user. The bio-signal interaction profile associated with the user may be anonymized such that any information stored in the profile used by the system platform to analyze bio-signal data of another user could not be used to identify a particular user.

The at least one computer server may be configured to identify a correspondence between the at least part of the time-coded feature event data stored in the bio-signal interaction profile stored at the at least one computer server with time-coded feature event data received from at least one second client computing device associated with a second user. The system may be configured to identify and determine where multiple users have experienced the same feature events. Where this has occurred, the at least one computer server may be configured to classify at least part of time-coded bio-signal data received from the at least one second client computing device corresponding to the time-coded feature event data received from the at least one second client computing in accordance with the user-response classification. Accordingly, the system platform may attempt to classify the second user's bio-signal data based on a user-response classification determined by the system platform for the prior user. The at least one computer server may be configured to then update a bio-signal interaction profile associated with the second user with the classification of the at least part of the time-coded bio-signal data received from the at least one second client computing device, the at least part of the time-coded bio-signal data received from the at least one second client computing device, and the at least part of the time-coded feature event data received from the at least one second client computing device, in accordance with a received confirmation of the user-response classification from the at least one second client computing device. An application where this may be useful is in comparing bio-signal responses of one user to another user when experiencing playback of media, such as music or video. The acquired time-coded feature event data may therefore comprise an identification of playback of a particular media, and the user-response classification may comprise a determination of the user having liked the particular media. The at least one computer server may be configured to transmit a recommendation of at least one other particular media to the at least one second client computing device whose user-response classification corresponded to the prior user's user-response classification.

The system platform may include at least one non-bio-signal sensor at and in communication with the at least one client computing device, the at least one client computing device configured to: receive time-coded non-bio-signal sensor data from the at least one non-bio-signal sensor; wherein the acquired time-coded feature event data is based at least partly on the received time-coded non-bio-signal sensor data.

The acquired time-coded feature event data may be based at least partly on calendar data stored on the at least one client computing device.

The acquired time-coded feature event data may be based at least partly on event data input from the user.

The at least one bio-signal sensor may comprise a head-mountable brainwave sensor, and the time-coded bio-signal sensor data comprises brainwave data of the user.

The at least one client computing device may be configured to transmit at least part of the bio-signal sensor data to at least one second client computing device for use as input by the at least one second client computing device.

The at least one client computing device may be configured to transmit the user-response classification to at least one second client computing device for use as input by the at least one second client computing device.

The at least one computer server may be configured to transmit at least part of the bio-signal sensor data to at least one second client computing device for use as input by the at least one second client computing device.

The at least one computer server may be configured to transmit the user-response classification to at least one second client computing device for use as input by the at least one second client computing device.

The at least one client computing device may be configured to update notification settings of the at least one client computing device in accordance with an identification of subsequently-received time-coded bio-signal data corresponding to the user-response classification.

The computer server may be configured to determine the user-response classification based at least partly on a type of the at least one bio-signal sensor.

The at least one client computing device may be configured to process at least part of the time-coded bio-signal data in accordance with the bio-signal interaction profile at the client computing device, and transmit the processed time-coded bio-signal data to the at least one computer server, wherein the user-response classification is based at least partly on the processed time-coded bio-signal data.

In accordance with an aspect of the present invention, there may be provided a computer network implemented system for improving the operation of one or more biofeedback computer systems is provided comprising: one or more server computers linked to the Internet, and enabling one or more computer implemented utilities providing: a brain computer interface for connecting to one or more applications for enabling one or more biofeedback computer systems, the brain computer interface linking to one or more sensors that include at least one brain wave sensor and optionally a non-bio-signal data sensor; an intelligent bio-signal processing system that is operable to: capture bio-signal data and in addition optionally non-bio-signal data; and analyze the bio-signal data and non-bio-signal data, if any, so as to: extract one or more features related to at least one individual interacting with the biofeedback computer system; classify the individual based on the features by establishing one or more brain wave interaction profiles for the individual for improving the interaction of the individual with the one or more biofeedback computer systems, and initiate the storage of the brain waive interaction profiles to a database; and access one or more machine learning components or processes for further improving the interaction of the individual with the one or more biofeedback computer systems by updating automatically the brain wave interaction profiles based on detecting one or more defined interactions between the individual and the one or more of the biofeedback computer systems.

It will be appreciated that any module or component exemplified herein that executes instructions may include or otherwise have access to computer readable media such as storage media, computer storage media, or data storage devices (removable and/or non-removable) such as, for example, magnetic disks, optical disks, tape, and other forms of computer readable media. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD), blue-ray disks, or other optical storage, magnetic cassettes, magnetic tape, magnetic disk storage or other magnetic storage devices, or any other medium which can be used to store the desired information and which can be accessed by an application, module, or both. Any such computer storage media may be part of the mobile device, tracking module, object tracking application, etc., or accessible or connectable thereto. Any application or module herein described may be implemented using computer readable/executable instructions that may be stored or otherwise held by such computer readable media.

Thus, alterations, modifications and variations can be effected to the particular embodiments by those of skill in the art without departing from the scope of this disclosure, which is defined solely by the claims appended hereto.

Figure 17:
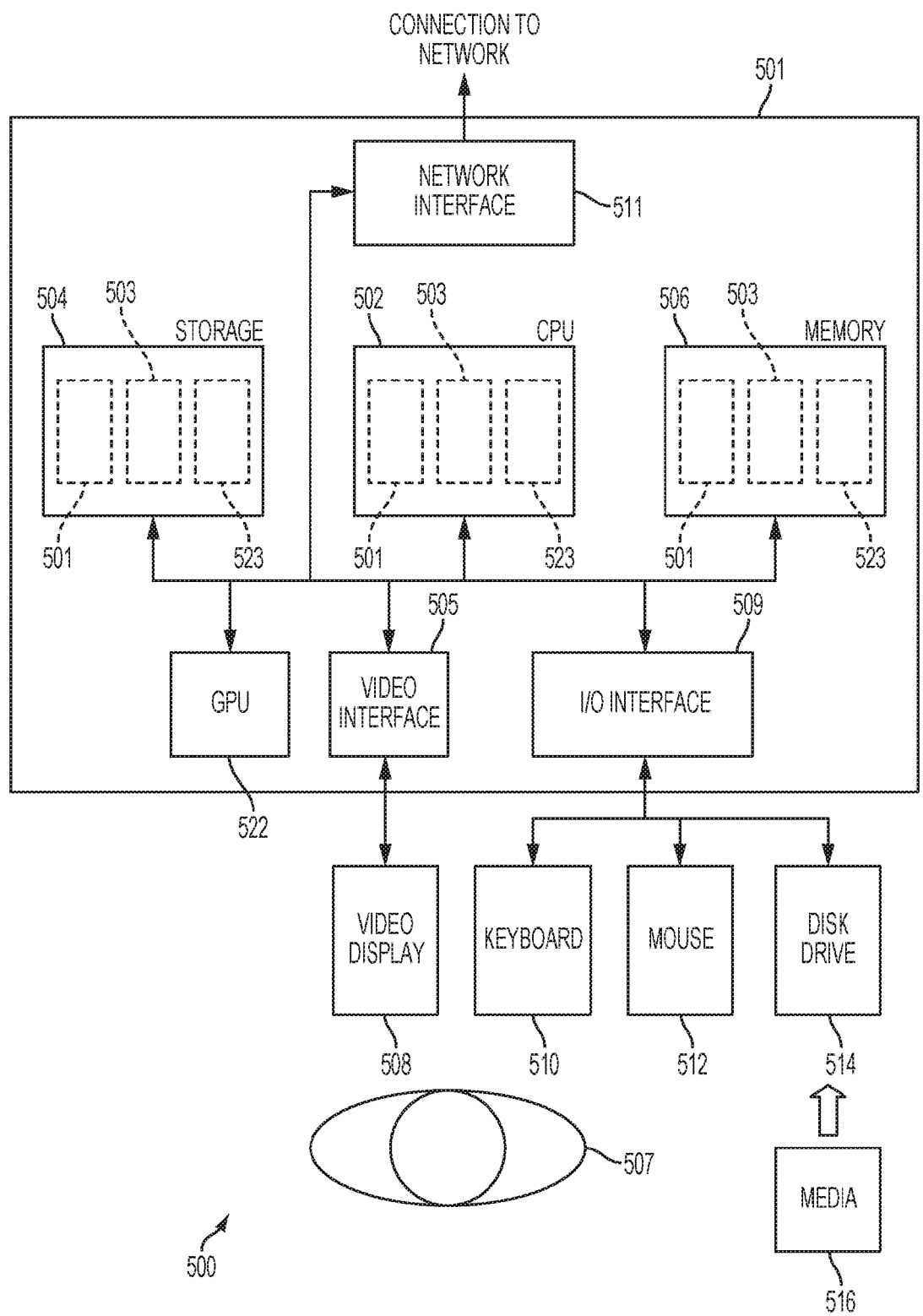
FIG. 17 illustrates a generic computer used to implement aspects of the present invention.

The present system and method may be practiced in various embodiments. A suitably configured computer device, and associated communications networks, devices, software and firmware may provide a platform for enabling one or more embodiments as described above. By way of example, FIG. 17 shows a generic computer device 500 that may include a central processing unit ("CPU") 502 connected to a storage unit 504 and to a random access memory 506. The CPU 502 may process an operating system 501, application program 503, and data 523. The operating system 501, application program 503, and data 523 may be stored in storage unit 504 and loaded into memory 506, as may be required. Computer device 500 may further include a graphics processing unit (GPU) 522 which is operatively connected to CPU 502 and to memory 506 to offload intensive image processing calculations from CPU 502 and run these calculations in parallel with CPU 502. An operator 507 may interact with the computer device 500 using a video display 508 connected by a video interface 505, and various input/output devices such as a keyboard 510, mouse 512, and disk drive or solid state drive 514 connected by an I/O interface 509. In known manner, the mouse 512 may be configured to control movement of a cursor in the video display 508, and to operate various graphical user interface (GUI) controls appearing in the video display 508 with a mouse button. The disk drive or solid state drive 514 may be configured to accept computer readable media 516. The computer device 500 may form part of a network via a network interface 511, allowing the computer device 500 to communicate with other suitably configured data processing systems (not shown).

In further aspects, the disclosure provides systems, devices, methods, and computer programming products, including non-transient machine-readable instruction sets, for use in implementing such methods and enabling the functionality described previously.

Although the disclosure has been described and illustrated in exemplary forms with a certain degree of particularity, it is noted that the description and illustrations have been made by way of example only. Numerous changes in the details of construction and combination and arrangement of parts and steps may be made. Accordingly, such changes are intended to be included in the invention, the scope of which is defined by the claims.

Except to the extent explicitly stated or inherent within the processes described, including any optional steps or components thereof, no required order, sequence, or combination is intended or implied. As will be will be understood by those skilled in the relevant arts, with respect to both processes and any systems, devices, etc., described herein, a wide range of variations is possible, and even advantageous, in various circumstances, without departing from the scope of the invention, which is to be limited only by the claims.

What is claimed is:

1. A brainwave monitoring system comprising:
   at least one client computing device storing or accessing a training application;
   at least one bio-signal sensor including at least one electroencephalography (EEG) bio-signal sensor at and in communication with the at least one client computing device;
   at least one user effector to provide a real-time biofeedback output for the training application; and at least one computer server in communication with the at least one computing device over a communications network;

the at least one client computing device configured to:
- acquire time-coded feature event data from user input, the at least one bio-signal sensor or data storage accessible by the client computing device;
- receive activation of a training session at the training application;
- generate a unique session identifier for the training session;
- receive time-coded EEG bio-signal data of a user from the at least one EEG bio-signal sensor;
- transmit the session identifier, the time-coded EEG bio-signal data and the acquired time-coded feature event data to the at least one computer server, the at least one computer server configured to:
  - generate a cloud pipeline instance to process the time-coded EEG bio-signal data and the time coded feature event data, the cloud pipeline instance defining pipeline parameters for a classification model;
  - extract, using the cloud pipeline instance, feature events from the time coded feature event data at feature event time codes, each feature event being a set of variables and corresponding values at least one feature event time code;
  - automatically search the feature events to identify patterns that are statistically significant, each pattern linked to a feature event time code of the at least one feature event time code, the pattern representing the user's response associated with the feature event data at the feature event time code;
  - using the feature event time codes linked to the patterns identified in the feature-events, label segments in the time-coded EEG bio-signal data having EEG bio-signal time-codes being same or similar to the feature event time codes linked to the patterns;
  - generate or update the classification model with the EEG bio-signal features extracted from labelled segments of the time-coded EEG bio-signal data, the classification model for predicting brain state based on the pipeline parameters;
  - determine and output a user-response classification of the segments of the time-coded EEG bio-signal data using the classification model and pipeline parameters, the user-response classification being an automatic prediction of a brain state of the user at the EEG bio-signal time codes and an automatic comparison to a target brain state for the training session;
- receive from the at least one computer server the user-response classification of at least part of the time-coded EEG bio-signal data and the classification model;
- indicate the user-response classification using the user effector as the biofeedback output for the training application;
- in accordance with a received input confirming the accuracy of the user-response classification, update the classification model using the confirmed user-response classification in a feedback loop;
- generate a client pipeline instance to process additional time-coded EEG bio-signal data;
- tune the client pipeline instance based on computational resources of the at least one client computing device;
- receive updated pipeline parameters for the classification model as part of a bio-signal interaction profile;
- update the client pipeline instance using the updated pipeline parameters for the classification model, the client pipeline instance to process additional time-coded EEG bio-signal data for the training session;
- receive the additional time-coded EEG bio-signal data of the user from the at least one EEG bio-signal sensor;
- automatically search the additional time-coded EEG bio-signal data and identify a pattern in a segment based on patterns of the labeled segments in the time-coded EEG bio-signal data of the feature event data using the client pipeline instance;
- generate an additional user-response classification of the segment of the additional time-coded EEG bio-signal data using the client pipeline instance;
- update the bio-signal interaction profile with the additional user-response classification;
- provide the real-time biofeedback output by actuating an output device of the at least one client computing device to generate alerts to users to indicate a user's compliance with the target brain state for the training session based at least on the identified pattern.

2. The system of claim 1 wherein the at least one client computing device is further configured to transmit a confirmation of the user-response classification to the at least one computer server.

3. The system of claim 2 wherein the at least one computer server is configured to update a bio-signal interaction profile associated with the user at the at least one computer server with the user-response classification, the at least part of the time-coded EEG bio-signal data, and the at least part of the time-coded feature event data at the at least one respective time code.

4. The system of claim 3 wherein the bio-signal interaction profile associated with the user is anonymized.

5. The system of claim 4 wherein the at least one computer server is configured to transmit at least part of the bio-signal sensor data to at least one second client computing device.

6. The system of claim 4 wherein the at least one computer server is configured to transmit the user-response classification to at least one second client computing device.

7. The system of claim 3 wherein the at least one computer server is configured to identify a correspondence between the at least part of the time-coded feature event data stored in the bio-signal interaction profile stored at the at least one computer server with time-coded feature event data received from at least one second client computing device associated with a second user, the correspondence based on the identified pattern of correspondence in the confirmed user-response classification used in the classification model associated with the user.

8. The system of claim 7 wherein the at least one computer server is configured to classify at least part of time-coded EEG bio-signal data received from the at least one second client computing device corresponding to the time-coded feature event data received from the at least one second client computing in accordance with the user-response classification.

9. The system of claim 8 wherein the at least one computer server is configured to update a bio-signal interaction profile associated with the second user with the classification of the at least part of the time-coded EEG bio-signal data received from the at least one second client computing device, the at least part of the time-coded EEG bio-signal data received from the at least one second client computing device, and the at least part of the time-coded feature event data received from the at least one second client computing device, in accordance with a received confirmation of the user-response classification from the at least one second client computing device.

10. The system of claim 9 wherein the acquired time-coded feature event data comprises an identification of playback of a particular media, the user-response classification comprises a determination of the user having liked the particular media; the at least one computer server configured to transmit a recommendation of at least one other particular media to the at least one second client computing device.

11. The system of claim 1 further comprising at least one non-bio-signal sensor at and in communication with the at least one client computing device, the at least one client computing device configured to:
receive time-coded non-bio-signal sensor data from the at least one non-bio-signal sensor;
wherein the acquired time-coded feature event data is based at least partly on the received time-coded non-bio-signal sensor data.

12. The system of claim 1 wherein the acquired time-coded feature event data is based at least partly on calendar data stored on the at least one client computing device.

13. The system of claim 1 wherein the acquired time-coded feature event data is based at least partly on event data input from the user.

14. The system of claim 1 wherein the at least one bio-signal sensor comprises a head-mountable brainwave sensor, and the time-coded bio-signal sensor data comprises brainwave data of the user.

15. The system of claim 1 wherein the at least one client computing device is configured to transmit at least part of the bio-signal sensor data to at least one second client computing device.

16. The system of claim 1 wherein the at least one client computing device is configured to transmit the user-response classification to at least one second client computing device.

17. The system of claim 1 wherein the at least one client computing device is configured to update notification settings of the at least one client computing device in accordance with an identification of subsequently-received time-coded EEG bio-signal data corresponding to the user-response classification.

18. The system of claim 1 wherein the computer server is configured to determine the user-response classification based at least partly on a type of the at least one bio-signal sensor.

19. The system of claim 1 comprising the at least one client computing device configured to process at least part of the time-coded EEG bio-signal data in accordance with the bio-signal interaction profile at the client computing device, and transmit the processed time-coded EEG bio-signal data to the at least one computer server, wherein the user-response classification is based at least partly on the processed time-coded EEG bio-signal data.

20. The system of claim 1 wherein the time-coded EEG bio-signal data is segmented and streamed into separate cloud pipelines, each cloud pipeline having different pipeline parameters,
the segmentation grouping portions of the time-coded EEG bio-signal data having a common feature or common features;
wherein each cloud pipeline is processed separately and only a selected cloud pipeline is utilized by the at least one server computer when probabilistically identifying the pattern;
wherein the selected cloud pipeline is selected based on relevance to a user-selected application; and
wherein the feedback loop, upon receiving the confirmed user-response classification further updates the pipeline parameters of the cloud pipeline to more closely match the portion of the time-coded EEG bio-signal data that is linked to the pattern of correspondence.

21. The system of claim 1, wherein the feature event is kth order feature-event comprising k primary feature-events, k being a positive integer, a primary feature event being a single feature variable and a corresponding discrete feature value.

22. The system of claim 1, the at least one client computing device configured to determine that the additional user response classification is outside of a desired mental state and trigger the user effector to provide feedback to the user that that the additional user response classification is outside of a desired mental to assist the user in achieving the desired mental state.

23. The system of claim 1 further wherein the biofeedback output includes modulation of presentation of stimulus including at least a timing of switching of images being rendered on a display interface of the at least one client computing device.

24. The system of claim 1 further wherein the biofeedback output includes modulation of presentation of stimulus including at least a modulation of audio signals output from a speaker of the at least one client computing device.

25. The system of claim 1 further wherein the biofeedback output includes modulation of presentation of stimulus including at least modulation of contrast of images being rendered on a display interface of the at least one client computing device.

26. A method for updating a classification model based on monitored brainwave data responsive to user confirmation, performed by at least one client computing device in communication with at least one electroencephalography (EEG) bio-signal sensor at the at least one client computing device, the at least one client computing device in communication with at least one computer server over a communications network, the at least one client computing device storing or accessing a training application, the method comprising:
receiving activation of a training session at the training application;
generating a unique session identifier for the training session;
receiving time-coded EEG bio-signal data of a user from the at least one electroencephalography (EEG) bio-signal sensor;
acquiring time-coded feature event data from user input, bio-signal sensors or data storage accessible by the client computing device;
transmitting the session identifier, the time-coded EEG bio-signal data and the acquired time-coded feature event data to the at least one computer server, the at least one computer server configured to:
generate a cloud pipeline instance to process the time-coded EEG bio-signal data, the cloud pipeline instance defining pipeline parameters for a classification model, the classification model for predicting brain state based on the pipeline parameters;
extract, using the cloud pipeline instance, feature events from the time coded feature event data at feature event time codes, each feature event being a set of variables and corresponding values at the at least one feature event time code;

automatically search the feature events to identify patterns that are statistically significant, each pattern linked to a feature event time code of the at least one feature event time code, the pattern representing the user's response associated with the feature event data at the feature event time code;

using the feature event time codes linked to the patterns identified in the feature-events, label segments in the time-coded EEG bio-signal data having EEG bio-signal time-codes being same or similar to the feature event time codes linked to the patterns;

generate or update the classification model with the EEG bio-signal features extracted from labelled segments of the time-coded EEG bio-signal data, the classification model for predicting brain state based on the pipeline parameters;

determine and output a user-response classification of the segments of the time-coded EEG bio-signal data using the classification model and pipeline parameters, the user-response classification being an automatic prediction of a brain state of the user at the EEG bio-signal time codes and an automatic comparison to a target brain state for the training session;

receiving from the at least one computer server the user-response classification and the classification model;

indicating the user-response classification using a user effector to provide a real-time biofeedback output for the training application;

in accordance with a received input confirming the accuracy of the user-response classification, updating the classification model using the confirmed user-response classification in a feedback loop generating client pipeline instance to process additional time-coded EEG bio-signal data;

tuning the client pipeline instance based on computational resources of the at least one client computing device;

receiving updated pipeline parameters for the classification model as part of a bio-signal interaction profile;

updating the client pipeline instance using the updated pipeline parameters for the classification model, the client pipeline instance to process additional time-coded EEG bio-signal data for the training session;

receiving the additional time-coded EEG bio-signal data of the user from the at least one EEG bio-signal sensor;

automatically search the additional time-coded EEG bio-signal data and identify a pattern in a segment based on patterns of the labeled segments in the time-coded EEG bio-signal data of the feature event data using the client pipeline instance;

generating an additional user-response classification of the segment of the additional time-coded EEG bio-signal data using the client pipeline instance;

updating the bio-signal interaction profile with the additional user-response classification; and providing the real-time biofeedback output by actuating an output device of the at least one client computing device to generate alerts to users to indicate a user's compliance with the target brain state for the training session based at least on the identified pattern.

27. The method of claim 26 comprising transmitting a confirmation of the user-response classification to the at least one computer server.

28. The method of claim 27 wherein the at least one computer server is configured to update a bio-signal interaction profile associated with the user at the at least one computer server with the user-response classification, the at least part of the time-coded EEG bio-signal data, and the at least part of the time-coded feature event data at the at least one respective time code.

29. The method of claim 28 wherein the bio-signal interaction profile associated with the user is anonymized.

30. The method of claim 29 wherein the at least one computer server is configured to transmit at least part of the bio-signal sensor data to at least one second client computing device.

31. The method of claim 29 wherein the at least one computer server is configured to transmit the user-response classification to at least one second client computing device.

32. The method of claim 28 wherein the at least one computer server is configured to identify a correspondence between the at least part of the time-coded feature event data stored in the bio-signal interaction profile stored at the at least one computer server with time-coded feature event data received from at least one second client computing device associated with a second user.

33. The method of claim 32 wherein the at least one computer server is configured to classify at least part of time-coded EEG bio-signal data received from the at least one second client computing device corresponding to the time-coded feature event data received from the at least one second client computing in accordance with the user-response classification.

34. The method of claim 33 wherein the at least one computer server is configured to update a bio-signal interaction profile associated with the second user with the classification of the at least part of the time-coded EEG bio-signal data received from the at least one second client computing device, the at least part of the time-coded EEG bio-signal data received from the at least one second client computing device, and the at least part of the time-coded feature event data received from the at least one second client computing device, in accordance with a received confirmation of the user-response classification from the at least one second client computing device.

35. The method of claim 34 wherein the acquired time-coded feature event data comprises an identification of playback of a particular media, the user-response classification comprises a determination of the user having liked the particular media; the at least one computer server configured to transmit a recommendation of at least one other particular media to the at least one second client computing device.

36. The method of claim 26 wherein at least one non-bio-signal sensor is located at and is in communication with the at least one client computing device, the method comprising:

receiving time-coded non-bio-signal sensor data from the at least one non-bio-signal sensor;

wherein the acquired time-coded feature event data is based at least partly on the received time-coded non-bio-signal sensor data.

37. The method of claim 26 wherein the acquired time-coded feature event data is based at least partly on calendar data stored on the at least one client computing device.

38. The method of claim 26 wherein the acquired time-coded feature event data is based at least partly on event data input from the user.

39. The method of claim 26 wherein the at least one bio-signal sensor comprises a head-mountable brainwave sensor, and the time-coded bio-signal sensor data comprises brainwave data of the user.

40. The method of claim 26 comprising transmitting at least part of the bio-signal sensor data to at least one second client computing device.

41. The method of claim 26 comprising transmitting the user-response classification to at least one second client computing device.

42. The method of claim 26 comprising updating notification settings of the at least one client computing device in accordance with an identification of subsequently-received time-coded EEG bio-signal data corresponding to the user-response classification.

43. The method of claim 26 wherein the computer server is configured to determine the user-response classification based at least partly on a type of the at least one bio-signal sensor.

44. The method of claim 26 comprising processing at least part of the time-coded EEG bio-signal data in accordance with the bio-signal interaction profile at the client computing device, and transmitting the processed time-coded EEG bio-signal data to the at least one computer server, wherein the user-response classification is based at least partly on the processed time-coded EEG bio-signal data.

* * * * *